United States Patent
Palmer et al.

(10) Patent No.: US 8,535,714 B2
(45) Date of Patent: *Sep. 17, 2013

(54) SMALL VOLUME ORAL TRANSMUCOSAL DOSAGE FORMS CONTAINING SUFENTANIL FOR TREATMENT OF PAIN

(75) Inventors: Pamela Palmer, San Francisco, CA (US); Thomas Schreck, Portola Valley, CA (US); Lawrence Hamel, Pacific Grove, CA (US); Stelio Tzannis, Petaluma, CA (US); Andrew Poutiatine, Mill Valley, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/276,165

(22) Filed: Oct. 18, 2011

(65) Prior Publication Data

US 2012/0035216 A1    Feb. 9, 2012

Related U.S. Application Data

(63) Continuation-in-part of application No. 11/985,162, filed on Nov. 14, 2007, which is a continuation-in-part of application No. 11/650,174, filed on Jan. 5, 2007, now Pat. No. 8,202,535, application No. 13/276,165, which is a continuation-in-part of application No. 11/825,251, filed on Jul. 3, 2007, now Pat. No. 8,252,329, which is a continuation-in-part of application No. 11/650,227, filed on Jan. 5, 2007, now Pat. No. 8,252,328.

(60) Provisional application No. 60/756,937, filed on Jan. 6, 2006, provisional application No. 60/860,569, filed on Nov. 22, 2006, provisional application No. 60/818,730, filed on Jul. 6, 2006, provisional application No. 60/756,937, filed on Jan. 6, 2006.

(51) Int. Cl.
*A61K 31/44*    (2006.01)

(52) U.S. Cl.
USPC .......................................... 424/464; 514/329

(58) Field of Classification Search
USPC .......................................... 424/464; 514/329
See application file for complete search history.

(56) References Cited

U.S. PATENT DOCUMENTS

| | | | |
|---|---|---|---|
| 2,621,655 A | 12/1952 | Olson et al. | |
| 3,444,858 A | 5/1969 | Russell | |
| 4,020,558 A | 5/1977 | Cournut et al. | |

(Continued)

FOREIGN PATENT DOCUMENTS

| | | |
|---|---|---|
| CN | 2776369 Y | 5/2006 |
| EP | 1243524 A2 | 9/2002 |

(Continued)

OTHER PUBLICATIONS

"FDA Guidance for Industry: Container Closure Systems for Packaging Human Drugs and Biologics," May 1999, pp. 1-E2.

(Continued)

*Primary Examiner* — Benjamin Packard
(74) *Attorney, Agent, or Firm* — Cooley LLP

(57) ABSTRACT

Compositions, systems and methods for administration of small volume sufentanil drug dosage forms via the oral transmucosal route of a subject for treatment of pain.

25 Claims, 23 Drawing Sheets

(56) References Cited

U.S. PATENT DOCUMENTS

| | | | |
|---|---|---|---|
| 4,226,848 | A | 10/1980 | Nagai et al. |
| 4,229,447 | A | 10/1980 | Porter et al. |
| 4,237,884 | A | 12/1980 | Erickson |
| 4,474,308 | A | 10/1984 | Bergeron |
| 4,582,835 | A | 4/1986 | Lewis et al. |
| 4,671,953 | A | 6/1987 | Stanley et al. |
| 4,764,378 | A | 8/1988 | Keith et al. |
| 4,785,969 | A | 11/1988 | McLaughlin |
| 4,863,737 | A | 9/1989 | Stanley et al. |
| 4,873,076 | A | 10/1989 | Fishman et al. |
| 4,880,634 | A | 11/1989 | Speiser et al. |
| 4,950,234 | A | 8/1990 | Fujioka et al. |
| 5,080,903 | A | 1/1992 | Ayache et al. |
| 5,112,616 | A | 5/1992 | McCarty et al. |
| 5,122,127 | A | 6/1992 | Stanley et al. |
| 5,132,114 | A | 7/1992 | Stanley et al. |
| 5,178,878 | A | 1/1993 | Wehling et al. |
| 5,223,264 | A | 6/1993 | Wehling et al. |
| 5,236,714 | A | 8/1993 | Lee et al. |
| 5,288,497 | A | 2/1994 | Stanley et al. |
| 5,288,498 | A | 2/1994 | Stanley et al. |
| 5,296,234 | A | 3/1994 | Hadaway et al. |
| 5,348,158 | A | 9/1994 | Honan et al. |
| 5,352,680 | A | 10/1994 | Portoghese et al. |
| 5,482,965 | A | 1/1996 | Rajadhyaksha et al. |
| 5,489,025 | A | 2/1996 | Romick |
| 5,489,689 | A | 2/1996 | Mathew |
| 5,507,277 | A | 4/1996 | Rubsamen et al. |
| 5,507,807 | A | 4/1996 | Shippert |
| 5,657,748 | A | 8/1997 | Braithwaite et al. |
| 5,660,273 | A | 8/1997 | Discko, Jr. |
| 5,694,919 | A | 12/1997 | Rubsamen et al. |
| 5,710,551 | A | 1/1998 | Ridgeway et al. |
| 5,724,957 | A | 3/1998 | Rubsamen et al. |
| 5,735,263 | A | 4/1998 | Rubsamen et al. |
| 5,752,620 | A | 5/1998 | Pearson |
| 5,785,989 | A | 7/1998 | Stanley et al. |
| 5,800,832 | A | 9/1998 | Tapolsky et al. |
| 5,827,525 | A | 10/1998 | Liao et al. |
| 5,850,937 | A | 12/1998 | Rauche et al. |
| 5,855,908 | A | 1/1999 | Stanley et al. |
| 5,945,651 | A | 8/1999 | Chorosinski et al. |
| 5,950,632 | A | 9/1999 | Reber et al. |
| 5,954,641 | A | 9/1999 | Kehr et al. |
| 5,968,547 | A | 10/1999 | Reder et al. |
| 5,981,552 | A | 11/1999 | Alam et al. |
| 5,995,938 | A | 11/1999 | Whaley et al. |
| 5,997,518 | A | 12/1999 | Laibovitz et al. |
| 6,024,981 | A | 2/2000 | Khankari et al. |
| 6,039,251 | A | 3/2000 | Holowko et al. |
| 6,116,414 | A | 9/2000 | Discko, Jr. |
| 6,171,294 | B1 | 1/2001 | Southam et al. |
| 6,190,326 | B1 | 2/2001 | McKinnon et al. |
| 6,200,604 | B1 | 3/2001 | Pather et al. |
| 6,210,699 | B1 | 4/2001 | Acharya et al. |
| 6,216,033 | B1 | 4/2001 | Southam et al. |
| 6,230,927 | B1 | 5/2001 | Schoonen et al. |
| 6,234,343 | B1 | 5/2001 | Papp et al. |
| 6,248,789 | B1 | 6/2001 | Weg et al. |
| 6,264,981 | B1 | 7/2001 | Zhang et al. |
| 6,284,512 | B1 | 9/2001 | Warkentin et al. |
| 6,294,999 | B1 | 9/2001 | Yarin et al. |
| 6,310,072 | B1 | 10/2001 | Smith et al. |
| 6,319,510 | B1 | 11/2001 | Yates et al. |
| 6,328,159 | B1 | 12/2001 | Discko, Jr. |
| 6,350,470 | B1 | 2/2002 | Pather et al. |
| 6,358,944 | B1 | 3/2002 | Lederman et al. |
| 6,391,335 | B1 | 5/2002 | Pather et al. |
| 6,417,184 | B1 | 7/2002 | Ockert et al. |
| 6,425,892 | B2 | 7/2002 | Southam et al. |
| 6,484,718 | B1 | 11/2002 | Schaeffer et al. |
| 6,488,953 | B2 | 12/2002 | Halliday et al. |
| 6,495,120 | B2 | 12/2002 | McCoy et al. |
| 6,500,456 | B1 | 12/2002 | Capella et al. |
| 6,509,036 | B2 | 1/2003 | Pather et al. |
| 6,541,021 | B1 | 4/2003 | Johnson et al. |
| 6,576,250 | B1 | 6/2003 | Pather et al. |
| 6,599,529 | B1 * | 7/2003 | Skinhøj et al. .............. 424/458 |
| 6,605,060 | B1 | 8/2003 | O'Neil et al. |
| 6,607,750 | B2 | 8/2003 | Upadhyay et al. |
| 6,641,838 | B2 | 11/2003 | Pather et al. |
| 6,642,258 | B1 | 11/2003 | Bourrie et al. |
| 6,645,528 | B1 | 11/2003 | Straub et al. |
| 6,651,651 | B1 | 11/2003 | Bonney et al. |
| 6,660,295 | B2 | 12/2003 | Watanabe et al. |
| 6,680,071 | B1 | 1/2004 | Johnson et al. |
| 6,682,716 | B2 | 1/2004 | Hodges et al. |
| 6,685,951 | B2 | 2/2004 | Cutler et al. |
| 6,689,373 | B2 | 2/2004 | Johnson et al. |
| 6,726,053 | B1 | 4/2004 | Harrold |
| 6,752,145 | B1 | 6/2004 | Bonney et al. |
| 6,759,059 | B1 | 7/2004 | Pettersson et al. |
| 6,761,910 | B1 | 7/2004 | Pettersson et al. |
| 6,762,684 | B1 | 7/2004 | Camhi et al. |
| 6,764,696 | B2 | 7/2004 | Pather et al. |
| 6,776,978 | B2 | 8/2004 | Rabinowitz et al. |
| 6,793,075 | B1 | 9/2004 | Jeter et al. |
| 6,796,429 | B2 | 9/2004 | Cameron et al. |
| 6,824,512 | B2 | 11/2004 | Warkentin et al. |
| 6,835,194 | B2 | 12/2004 | Johnson et al. |
| 6,855,310 | B2 | 2/2005 | Rabinowitz et al. |
| 6,881,208 | B1 | 4/2005 | Phipps et al. |
| 6,914,668 | B2 | 7/2005 | Brestel et al. |
| 6,916,485 | B2 | 7/2005 | Aiache et al. |
| 6,932,983 | B1 | 8/2005 | Straub et al. |
| 6,959,808 | B2 | 11/2005 | Discko et al. |
| 6,961,541 | B2 | 11/2005 | Overy et al. |
| 6,963,289 | B2 | 11/2005 | Aljadeff et al. |
| 6,969,508 | B2 | 11/2005 | Dugger et al. |
| 6,974,590 | B2 | 12/2005 | Pather et al. |
| 6,999,028 | B2 | 2/2006 | Egbert et al. |
| 7,018,370 | B2 | 3/2006 | Southam et al. |
| 7,018,619 | B2 | 3/2006 | Rabinowitz et al. |
| 7,044,125 | B2 | 5/2006 | Vedrine et al. |
| 7,044,302 | B2 | 5/2006 | Conley et al. |
| 7,070,762 | B2 | 7/2006 | Rabinowitz et al. |
| 7,070,764 | B2 | 7/2006 | Rabinowitz et al. |
| 7,070,765 | B2 | 7/2006 | Rabinowitz et al. |
| 7,072,738 | B2 | 7/2006 | Bonney et al. |
| 7,074,935 | B2 | 7/2006 | Mathew et al. |
| 7,078,018 | B2 | 7/2006 | Rabinowitz et al. |
| 7,078,019 | B2 | 7/2006 | Rabinowitz et al. |
| 7,090,830 | B2 | 8/2006 | Hale |
| 7,090,866 | B2 | 8/2006 | Johnson et al. |
| 7,119,690 | B2 | 10/2006 | Lerch et al. |
| 7,168,626 | B2 | 1/2007 | Lerch et al. |
| 7,169,378 | B2 | 1/2007 | Rabinowitz et al. |
| 7,198,172 | B2 | 4/2007 | Harvey et al. |
| 7,208,604 | B2 | 4/2007 | Mathew et al. |
| 7,215,295 | B2 | 5/2007 | Egbert et al. |
| 7,248,165 | B2 | 7/2007 | Collins et al. |
| 7,276,246 | B2 | 10/2007 | Zhang et al. |
| 7,295,890 | B2 | 11/2007 | Jean-Pierre et al. |
| 7,306,812 | B2 | 12/2007 | Zhang et al. |
| 7,458,374 | B2 | 12/2008 | Hale et al. |
| 7,468,179 | B2 | 12/2008 | Rabinowitz et al. |
| 7,484,642 | B2 | 2/2009 | Bonney et al. |
| 7,500,444 | B2 | 3/2009 | Bonney et al. |
| 7,552,728 | B2 | 6/2009 | Bonney et al. |
| 8,202,535 | B2 | 6/2012 | Palmer et al. |
| 2001/0020147 | A1 | 9/2001 | Staniforth et al. |
| 2002/0026330 | A1 | 2/2002 | Klein et al. |
| 2002/0037491 | A1 | 3/2002 | Halliday et al. |
| 2002/0071857 | A1 | 6/2002 | Kararli et al. |
| 2002/0110578 | A1 | 8/2002 | Pather et al. |
| 2002/0142050 | A1 | 10/2002 | Straub et al. |
| 2002/0160043 | A1 | 10/2002 | Coleman et al. |
| 2003/0008005 | A1 | 1/2003 | Cutler et al. |
| 2003/0015196 | A1 | 1/2003 | Hodges et al. |
| 2003/0015197 | A1 | 1/2003 | Hale et al. |
| 2003/0017175 | A1 | 1/2003 | Cutler |
| 2003/0017994 | A1 | 1/2003 | Cutler et al. |
| 2003/0022910 | A1 | 1/2003 | Cutler et al. |
| 2003/0035776 | A1 | 2/2003 | Hodges et al. |

| | | |
|---|---|---|
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0088236 A1 | 5/2003 | Johnson et al. |
| 2003/0091629 A1 | 5/2003 | Pather et al. |
| 2003/0099158 A1 | 5/2003 | De la Huerga |
| 2003/0124185 A1* | 7/2003 | Oshlack et al. ............. 424/465 |
| 2003/0130314 A1 | 7/2003 | Druzgala et al. |
| 2003/0132239 A1 | 7/2003 | Konig et al. |
| 2003/0171401 A1 | 9/2003 | Johnson et al. |
| 2003/0173408 A1 | 9/2003 | Mosher et al. |
| 2003/0181501 A1 | 9/2003 | Le et al. |
| 2003/0185872 A1 | 10/2003 | Kochinke et al. |
| 2003/0190290 A1 | 10/2003 | Ross et al. |
| 2003/0232080 A1 | 12/2003 | Pather et al. |
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson et al. |
| 2004/0080515 A1 | 4/2004 | Hagiwara et al. |
| 2004/0092531 A1 | 5/2004 | Chizh et al. |
| 2004/0094564 A1 | 5/2004 | Papp et al. |
| 2004/0096402 A1 | 5/2004 | Hodges et al. |
| 2004/0120896 A1 | 6/2004 | Dugger et al. |
| 2004/0133305 A1 | 7/2004 | Jean-Pierre |
| 2004/0157884 A1 | 8/2004 | Johnson et al. |
| 2004/0158349 A1 | 8/2004 | Bonney et al. |
| 2004/0170567 A1 | 9/2004 | Sackler et al. |
| 2004/0180080 A1 | 9/2004 | Furusawa et al. |
| 2004/0185003 A1 | 9/2004 | Rabinowitz et al. |
| 2004/0191178 A1 | 9/2004 | Cutler et al. |
| 2004/0202617 A1 | 10/2004 | Rabinowitz et al. |
| 2004/0213855 A1 | 10/2004 | Pettersson et al. |
| 2004/0248964 A1 | 12/2004 | Crooks et al. |
| 2004/0253307 A1 | 12/2004 | Hague et al. |
| 2005/0038062 A1 | 2/2005 | Burns et al. |
| 2005/0049464 A1 | 3/2005 | Lassers et al. |
| 2005/0054942 A1 | 3/2005 | Melker |
| 2005/0064030 A1 | 3/2005 | Pather et al. |
| 2005/0065175 A1 | 3/2005 | Gonzales et al. |
| 2005/0075273 A1 | 4/2005 | Rabinowitz et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0129737 A1 | 6/2005 | Johnson et al. |
| 2005/0131337 A1 | 6/2005 | Phipps et al. |
| 2005/0142197 A1 | 6/2005 | Moe et al. |
| 2005/0142198 A1 | 6/2005 | Moe et al. |
| 2005/0150488 A1 | 7/2005 | Dave et al. |
| 2005/0150489 A1 | 7/2005 | Dunfield et al. |
| 2005/0163838 A1 | 7/2005 | Moe et al. |
| 2005/0169989 A1 | 8/2005 | Moe et al. |
| 2005/0171464 A1 | 8/2005 | Phipps et al. |
| 2005/0176790 A1 | 8/2005 | Bartholomaus |
| 2005/0177275 A1 | 8/2005 | Harvey et al. |
| 2005/0192218 A1 | 9/2005 | Ellis et al. |
| 2005/0258066 A1 | 11/2005 | Conley et al. |
| 2006/0026035 A1 | 2/2006 | Younkes et al. |
| 2006/0031099 A1 | 2/2006 | Vitello et al. |
| 2006/0039959 A1 | 2/2006 | Wessling et al. |
| 2006/0045865 A1 | 3/2006 | Jacob et al. |
| 2006/0062812 A1 | 3/2006 | Ross et al. |
| 2006/0067978 A1 | 3/2006 | Heiler et al. |
| 2006/0069344 A1 | 3/2006 | Southam et al. |
| 2006/0089858 A1 | 4/2006 | Ling et al. |
| 2006/0134200 A1 | 6/2006 | Vandoni et al. |
| 2006/0210632 A1 | 9/2006 | Oury et al. |
| 2006/0216352 A1 | 9/2006 | Nystrom et al. |
| 2006/0229570 A1 | 10/2006 | Lovell et al. |
| 2006/0233718 A1 | 10/2006 | Rabinowitz et al. |
| 2006/0251587 A1 | 11/2006 | Rabinowitz et al. |
| 2006/0292219 A1 | 12/2006 | Pather et al. |
| 2007/0020186 A1 | 1/2007 | Stroppolo et al. |
| 2007/0031502 A1 | 2/2007 | Pettersson et al. |
| 2007/0036853 A1 | 2/2007 | Agarwal et al. |
| 2007/0071806 A1 | 3/2007 | McCarty et al. |
| 2007/0074722 A1 | 4/2007 | Giroux et al. |
| 2007/0104763 A1 | 5/2007 | Jobdevairakkam et al. |
| 2007/0178052 A1 | 8/2007 | Rabinowitz et al. |
| 2007/0184096 A1 | 8/2007 | Ameri et al. |
| 2007/0185084 A1 | 8/2007 | McKinney et al. |
| 2007/0186923 A1 | 8/2007 | Poutiatine et al. |
| 2007/0190130 A1 | 8/2007 | Mark et al. |
| 2007/0207207 A1 | 9/2007 | Tzannis et al. |
| 2007/0260491 A1 | 11/2007 | Palmer et al. |
| 2007/0286900 A1 | 12/2007 | Herry |
| 2007/0299687 A1 | 12/2007 | Palmer et al. |
| 2008/0147044 A1 | 6/2008 | Palmer et al. |
| 2008/0164275 A1 | 7/2008 | Poutiatine et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2010/0105735 A1 | 4/2010 | Palmer et al. |
| 2010/0130551 A1 | 5/2010 | Pushpala et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0288128 A1 | 11/2011 | Palmer et al. |

FOREIGN PATENT DOCUMENTS

| | | |
|---|---|---|
| EP | 2114383 B1 | 7/2010 |
| GB | 2309966 A | 8/1997 |
| JP | 2003-525081 A | 8/2003 |
| JP | 2004-511310 A | 4/2004 |
| JP | 2004-531806 A | 10/2004 |
| JP | 2005-199066 A | 7/2005 |
| WO | WO 00/16750 A1 | 3/2000 |
| WO | WO 00/57858 A1 | 10/2000 |
| WO | WO 01/30288 A1 | 5/2001 |
| WO | WO 01/64182 A2 | 9/2001 |
| WO | WO 01/97780 A2 | 12/2001 |
| WO | WO 02/32487 | 4/2002 |
| WO | WO 02/067903 A2 | 9/2002 |
| WO | WO 02/067916 A2 | 9/2002 |
| WO | WO 02/078594 A2 | 10/2002 |
| WO | WO 2004/069198 A2 | 8/2004 |
| WO | WO 2004/080515 A1 | 9/2004 |
| WO | WO 2006/097361 A1 | 9/2006 |
| WO | WO 2007/081949 A2 | 7/2007 |
| WO | WO 2008/085764 A1 | 7/2008 |
| WO | WO 2008/085765 A2 | 7/2008 |
| WO | WO 2009/021106 A1 | 2/2009 |

OTHER PUBLICATIONS

"Triazolam" Drug Facts and Comparisons (Fiftieth Edition). 1996. Wolters Kluwer. p. 1619.
Abrams R, et al., Anesth. Prog. 1993;40(3):63-6.
AcelRx Pharmaceuticals, Inc., "AcelRx Pharmaceuticals Reports Positive Results from a Clinical Trial of Sublingual Sufentanil/Triazolam NanoTab™ Combination (ARX-03) in Treating Procedural Pain and Anxiety," 2 pages, Press Release (Jan. 12, 2009).
ACTIQ fact sheet printed Mar. 2004.
Actiq package insert (Cephalon) (2004).
AHFS Drug Information, 28:08.08, 2157-2160, 2007.
Anlar S, et al., Pharm. Res., 11(2):231-6, 1994.
Bayrak F., et al., J. Opiod Management, 3(2):74-78, 2007.
Berthold, et al., (2007) Oral Surg Oral Med Oral Pathol Oral Radiol Endo, 84(2):119-24.
Bethune-Volters A, Anti-cancer drugs, vol. 17, No. 2, pp. 217-224, 2006.
Bovill GJ, et al., Anesthesiology 61:502-506, 1984.
Brendenberg, et al., 2003, Acta Universitatis Upsaliensis; Jan. 1983, Comprehensive Summaries of Uppsala Dissertation. from the Faculty of Pharmacy 287.
Brendenberg, et al., European Journal of Pharmaceutical Sciences; 20:327-334, 2003.
Brown et al., Amer. Fam. Pharm. 71(1) 85-90, 2005.
Brusset A, et al. Clin Drug Invest, 18(5):377-89, 1999.
Chauvin, Anesth Analg; 1989; 68(1): 1-4.
Coluzzi PH; "Breakthrough cancer pain: a randomized trial comparing oral transmucosal fentanyl citrate (OTFC) and morphine sulfate immediate release (MSIR)"; Pain; 2001; 91:123-30.

Coluzzi, et al., 1998, J Pain Symp Manage, 16(3):184-92.
Dale, et al., 2002, Acta Anaesth Scand, 46:759-770.
Darwish et al., 2007, J Clin Pharm 47: 56-63.
Darwish, et al., 2005, Clinical Pharmacokinetics, 44(12): 1279-86.
Darwish, et al., 2006, Clinical Pharmacokinetics, 45(8):843-50.
Darwish, et al., 2006, Clinical Therapies, 28(5):707-14.
Darwish, et al., 2006, Clinical Therapies, 28(5):715-24.
Darwish, et al., 2007, Expert Opin Pharmacother, 8(13):2011-6.
Darwish, et al., 2008, Clin Drug Invest, 28(1):1-7.
De Castro J, et al., Acta Anesth Belgica, 107-128, 1976.
de Vries M et al., Critical Reviews in Therapeutic Drug Carrier Systems, 8(3):271-303, 1991.
Demeules, et al., Eur J Anaesthesiol Suppl. 2003; 28:7-11.
Ikinci G, et al., Int. J. Pharm., 277(1-2):173-8, 2004.
International Preliminary Report on Patentability for International Application No. PCT/US2007/000527 (WO 2007/081947), dated Feb. 24, 2009.
International Preliminary Report on Patentability for International Application No. PCT/US2007/000529 (WO 2007/081949), dated Jul. 8, 2008.
International Preliminary Report on Patentability for International Application No. PCT/US2007/089016 (WO 2008/085763), dated Jul. 7, 2009.
International Preliminary Report on Patentability for International Application No. PCT/US2007/089017 (WO 2008/085764), dated Jul. 7, 2009.
International Search Report and Written Opinion dated Feb. 4, 2008 issued in PCT/2007/00528 (WO/2007/081948).
International Search Report and Written Opinion dated Dec. 17, 2007 issued in PCT/2007/00527 (WO/2007/081947).
International Search Report and Written Opinion for International Application No. PCT/US2007/089018 (WO 2008/085765), mailed Oct. 15, 2008.
International Search Report and Written Opinion for international Application No. PCT/US2010/027437 (WO 2010/107761), mailed Jun. 21, 2010.
International Search Report and Written Opinion for International Application No. PCT/US2009/064232 (WO 2010/059504), mailed Mar. 17, 2010.
International Search Report and Written Opinion for International Application No. PCT/US2007/089016 (WO 2008/085763), mailed Jun. 17, 2008.
ISR PCT/US08/072445, mailed Oct. 20, 2008.
ISR WO 2007/081947, mailed Dec. 17, 2007.
ISR WO 2007/081948, mailed Feb. 4, 2008.
ISR WO 2007/081949, mailed Sep. 11, 2007.
ISR WO 2007/133478, mailed Aug. 5, 2008.
ISR WO 2008/002358, mailed Aug. 21, 2008.
ISR WO 2008/085764, mailed Jun. 23, 2008.
ISR WO 2008/085765, mailed Oct. 15, 2008.
ISR WO 2010/059504, mailed Mar. 17, 2010.
ISR WO 2010/107761, mailed Jun. 21, 2010.
Jackson, et al., Journal of Pain and Sympt Management, 23(6):450-452, 2002.
Jackson, et al., 2006, Journal Clinical Psychopharmacology, 26(1):4-8.
James, et al., 2005, Clinical Radiology, 60:394-396.
Jeannet, et al., 1999, Eur J Paediatric Neurology, 3:73-77.
Joshi, et al., 1993, Indian Pediatr, 30(1):84-5.
Kaplan, et al., 1998, J Clin Pharmacol, 38(1): 14-21.
Karl, et al., 1992, Anesthesiology, 76:209-215.
Karl, et al., 1993, Anesthesiology, 78(5):885-91.
Karl, et al., 1997, Journal of Clinical Psychopharmacology, 17(3):169-172.
KGH Drug Information Bulletin, vol. 37(4) 2, 2004.
Khalil, et al., 1998, Paediatric Anaesthesia, (8):461-465.
Kling, "International Search Report," 4 pages, International Patent Appl. No. PCT/US2010/052655, European Patent Office (mailed Apr. 4, 2011).
Kling, "Written Opinion of the International Searching Authority," 4 pages, International Patent Appl. No. PCT/US2010/052655, European Patent Office (mailed Apr. 4, 2011).
Kogan, et al., 2002, Paediatric Anaesthesia, 12:685-689.
Kontinen, et al., 1993, Canadian Journal of Anesthesia, vol. 40, 829-834.
Kraus et al., "Procedural sedation and analgesia in children," Lancet 367:766-780 (2006).
Kress et al. "Sedation and Analgesia in the Intensive Care Unit". Am J Respir Crit Care Med. 166; 2002:1024-1028.
Kress, Clin. Therap., 31(6) 1177-1191, 2009.
Kroboth, et al., 1995, J Clin Psychopharmacol, 15(4):259-62.
Kunz, et al., 1993, Journal of Pain and Sympt Management, 8(4):189-190.
Lehmann K. A., et al., Acta Anaesthesiol. Scand., 35:221-226, 1991.
Lehmann K. A., et al., Acta Anaesthesiol. Scand., 37:176-180, 1993.
Lennernas, et al., Br. J. Clin. Pharmacol., 59(2):249-253, 2004.
Lichtor, et al., Anesth. Anal., 89(3):732-738, 1999.
Lim, et al., Can. J. Anaesth., 44(7):723-726, 1997.
Lipworth, et al., Eur. J. Clin. Pharmacol., 37:567-571, 1989.
Loeffler, J. Oral Maxillofacial. Surg., 50(9) 989-997, 1992.
Mather, Clin. Pharmacokinetics, 8:422-446, 1983.
Mathieu, et al., Can. J. Anaesth., 53:60-66, 2006.
McCann, et al., 2001, Anesthesia & Analgesia, 93:98-105.
Mendelson J, et al.; J Clin Pharmacol; 1997; 37:31-7.
Molander L and Lunell E, Eur J Clin Pharmacol, 56(11):813-819, 2001.
Monk, et al., Drugs, 36:286-313, 1988.
Motwani JG, Lipworth BJ; Clin Pharmacokinet; 1991; 21 (2):83-94.
Mystakidou K, et al.; Drug Deliv. 2006; 13(4):269-76.
Naguib, et al., 2000, Anesth Analg, 91 :473-9.
Nath RP, et al., J. Clin. Pharmacol. 39:619-623, 1999.
Odou, et al., 1998, Eur J Drug Metab Pharmacokinet, 23(2):87-91.
Odou, et al., 1999, Eur J Drug Metab Pharmacokinet, 24(1): 1-7.
Okayama, et al., Eur. J. Clin. Pharamcol., 26:151-155, 1984.
Onsolis Package Insert Jul. 2009.
Pavlin, et al., Anesthesiology. Jan. 1996; 84(1):23-37.
Portenoy RK, et al., Pain, 22(9):805-811, 2006.
Portenoy RK, et al., Pain, 79:303-312, 1999.
Puig, et al., Int. J. Clin. Pharmaco. Ther. Toxicol., 27(5):229-234, 1989.
Raza, et al., Can J Anaesth. Nov. 1989; 36(6):617-23.
Reisfield G, Wilson G; Journal of Palliative Medicine; 2007; 10(2):465-475.
Reynolds, et al., 2004, Pain, 110:182-188.
Rosow, Pharmacotherapy, 4:11-19, 1984.
Roy and Flynn, Pharm Res. 7:842-847, 1990.
Roy and Flynn, Pharm Res. 6(2):147-151, 1989.
Savoia, et al., Minerva Anesth, 67(9 Suppl 1):206-216, 2001.
Scavone, et al., 1986, J Clin Pharmacol, 26:208-10.
Scavone, et al., 1987, J Clin Psychpharmacol, 7(5):332-4.
Scavone, et al., 1992, Eur J Clin Pharmacol, 42(4):439-43.
Scholz J, et al.; Clin Pharmacokin ; 1996; 31:275-292.
Schreiber, et al., 2006, The American Journal of Emergency Medicine, 24:397-401.
Schwagmeier, et al., 1998, Br J Clin Pharmacol, 46:203-69.
Siepmann et al., Int. J. Pharm., 201(2):151-64, 2000.
Sinatra, et al., J. Clin. Anesth., 8:123-129, 1996.
Smith, et al., J. Clin. Pharmacol., 26(2):120-124, 1986.
Stopperich, et al., 1993, Anesth Prog, 40(4):117-21.
Streisand JB, et al.; Anesthesiology; 1991; 75:223-9.
Streisand JB, et al.; Anesthesiology; 1998; 88:305-9.
Sufenta Package Insert, 2006.
Supplementary European Search Report for European Application No. EP 08797363.2 dated Sep. 15, 2010.
Supplementary European Search Report for European Application No. EP 07716450.7 dated Apr. 6, 2011.
Tweedy, et al., 2001, J Clin Psychopharmacol, 21(3):268-72.
Van de Walle, et al., Acta Anaesth. Belg., 27(3):129-138, 2009.
Van Vlymen et al., Anesthesiology 90:740-747, 1999.
Vercauteren, et al., Anaesthesia, 43:270-273, 1988.
Viitanen, et al., 1999, Can J Anesth, 46(8):766-771.
Walder, et al., Swiss Med Wkly. Jun. 12, 2004; 134(23-24):333-46.
Weinberg, et al., Clin. Pharmacol. Ther., 44(3):335-342, 1988.
Wheeler, et al., Paediatric Anesthesia, 12:594-599, 2002.
Willens and Myslinski, Heart and Lung, 22:239-251, 1993.
Yager, et al., 1988, Am J Dis Child, 142:931-2.

Yeomans, et al., 2001, Vancouver Hospital and Health Science Center Drug and Therapeutics Newsletter, vol. 8(1) 2.
Young, "Written Opinion of the International Searching Authority," 5 pages, International Patent Appl. No. PCT/US08/72445, (Oct. 8, 2008).
Zedie, et al., 1996, Clin Pharmacal Ther, 59:341-8.
Zhang, et al., Clin. Pharmacokin. 41(9):661-680, 2002.
Ahmad, S. et al., "Fentanyl HCI iontophoretic transdermal system versus intravenous morphine pump after gynecologic surgery," Arch. Gynecol. Obstet. 276:251-258 (2007).
Albert, J. M. et al., "Patient-Controlled Analgesia vs. Conventional Intramuscular Analgesia Following Colon Surgery," Diseases of the Colon & Rectum, 31(2):83-86 (1988).
Chen et al., "Studies on Formulations of Fenntanyl-Containing Oral Adhesive Tablets," Chin. J. Pharm. 28(3):129-131 (1997).
Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-3245 (1998).
Coda, B.A. et al., "Comparative efficacy of patient-controlled administration of morphine, hydromorphone, or sufentanil for the treatment of oral mucositis pain following bone marrow transplantation," Pain, 72:333-346 (1997).
Collins, L. M. C. et al., "The Surface Area of the Adult Human Mouth and Thickness of the Salivary Film Covering the Teeth and Oral Mucosa," J. Dent. Res. 66(8):1300-1302 (1987).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
Fisher, D.M. et al., "Pharmacokinetics of an Implanted Osmotic Pump Delivering Sufentanil for the Treatment of Chronic Pain," Anesthesiology, 99(4):929-937 (Oct. 2003).
Grass, J., "Patient-Controlled Analgesia," Anesth. Analg., 101:S44-S61 (2005).
Hicks, R. et al., "USP Medication Safety Forum: Medication Errors Involving Patient-Controlled Analgesia," Joint Commission on Quality and Patient Safety, 34(12):734-742 (2008).
International Preliminary Report on Patentability for International Application No. PCT/US2007/000528, dated Jul. 8, 2008.
International Preliminary Report on Patentability for International Application No. PCT/US2007/089018, dated Jul. 7, 2009.
International Preliminary Report on Patentability for International Application No. PCT/US2010/052655, dated Apr. 17, 2012.
International Preliminary Report on Patentability for International Application No. PCT/US2009/064232, dated May 24, 2011.
International Preliminary Report on Patentability for International Application No. PCT/US2008/072445, dated Feb. 9, 2010.
Jia et al., p. 10, in Novel controlled-release dosage forms for drugs, Chemical Industry Press (CIP), China (2005).
Paix, A. et al., "Subcutaneous fentanyl and sufentanil infusion substitution for morphine intolerance in cancer pain management," Pain, 63:263-269 (1995).
Striebel, H. W. et al., "Patient-controlled intranasal analgesia (PCINA) for the management of postoperative pain: a pilot study," J Clin Anesth, 8:4-8 (1996).
Striebel, H. W. et al., "Patient-controlled intranasal analgesia: a method for noninvasive postoperative pain management," Anesth Analg, 83:548-551 (1996).
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-Controlled Transdermal Fentanyl Hydrochloride vs Intravenous Morphine Pump for Postoperative Pain: A randomized controlled trial," JAMA, 291(11):1333-1341 (2004).
Written Opinion for International Application No. PCT/US2007/000529, mailed Sep. 11, 2007.
Written Opinion for International Application No. PCT/US2007/089017, mailed Jun. 23, 2008.
Durfee, et al., 2006, American Journal Drug Delivery, 4(1):1-5(5).
Economou, "International Search Report," 4 pages, International Patent Appl. No. PCT/US2011/037401, European Patent Office (mailed Aug. 19, 2011).
Economou, "Written Opinion of the International Searching Authority," 6 pages, International Patent Appl. No. PCT/US2011/037401, European Patent Office (mailed Aug. 19, 2011).
Egan, et al., 2000, Anesthesiology, 92:665-73.
Ellmauer S, Anesth, 43(3):143-158, 1994.
Enting H.R, et al., J. Pain and Symptom Management, 29(2):213-217, 2005.
Farnsworth, et al., 1998, Anesth Analg, 86:138-40.
Fentora Package Insert, 100-800mcg dose of fentanyl; buccal absorption with approximately 50% absorbed transmucosally remainder swallowed/absorbed via GI tract. (p. 4 of package insert), 2007.
Friedman et al., Br. J. Clin. Pharmacol., 22:639-642, 1986.
Gardner-Nix, et al., 2001, J Pain Symptom Manage, 22:627-630.
Geldner, et al., 1997, Paediatric Anaesthesia, 7:103-109.
Gerak, et al., 1998, Psychopharmacology, 137(2):164-74.
Good P, et al., Pallial Med., 23(1):54-58, 2009.
Goodwin et al., Annals Emerg. Med. 45(2) 177-196, 2005.
Gordon, et al., Oncol. Nurs. Forum, 33(2):257-64, 2006.
Gram-Hansen, et al., 1988, Int J Clin Pharmacol Ther Toxicol, 26(6):323-4.
Guay et al., Can. J. Anaesth, 39(1): 14-20, 1992.
Halcion Package Insert, 2008.
Halliburton Jr, Anesthesiology, 56(3):229-233, 1988.
Halliburton Jr, Anesthesiology, 61(5):502-506, 1984.
Haynes, et al., Can. J. Anaesth, 40(3):286-288, 1993.
Hazardous Substances Data Bank (HSDB); (http://toxnet.nlm.nih.gov) Apr. 9, 2007; Name: SUFENTANIL; RN: 56030-54-7.
Helmers et al., Eur J Anesth, 11(3):181-5, 1994.
Helmers et al., Can. J. Anaesth., 36(5):494-497, 1989.
Henderson, et al., 1988, Anesthesiology, 68:671-675.
Heshmati et al., Iran. J. Pharmacol. Ther., 5:131-133, 2006.
Hicks, JA, J. Royal Soc. Med., 81: 517-519, 1988.

* cited by examiner

SMALL VOLUME ORAL TRANSMUCOSAL DOSAGE FORMS CONTAINING SUFENTANIL FOR TREATMENT OF PAIN

CROSS-REFERENCE TO RELATED APPLICATIONS

This application is a Continuation-In-Part of U.S. patent application Ser. No. 11/985,162, filed Nov. 14, 2007, which is a Continuation-In-Part of U.S. patent application Ser. No. 11/650,174, filed Jan. 5, 2007, which claims priority benefit of U.S. Provisional Application Ser. No. 60/756,937, filed Jan. 6, 2006; and is a Continuation-In-Part of U.S. patent application Ser. No. 11/825,251, filed Jul. 3, 2007, which is a Continuation-In-Part of U.S. patent application Ser. No. 11/650,227 filed Jan. 5, 2007, which claims priority benefit of U.S. Provisional Ser. Nos. 60/860,569, 60/818,730, and 60/756,937, respectively filed Nov. 22, 2006, Jul. 6, 2006, and Jan. 6, 2006; the disclosures of all of which are incorporated herein by reference in their entirety.

BACKGROUND OF THE INVENTION

Oral dosage forms account for approximately eighty percent of all the drug dosage forms on the market. They are non-invasive, easily administered and have high patient compliance. Orally administered therapeutic agents, however, must be transported to the stomach and small intestine for absorption across the gastrointestinal (GI) mucosal membranes into the blood. The efficiency of absorption of a drug following oral administration can be low because of metabolism within the GI tract and first-pass metabolism within the liver, resulting in relatively lengthy onset times or erratic absorption characteristics that are not well-suited to control acute disorders. The majority of oral dosage forms on the market are designed for GI delivery. Relatively few oral dosage forms are designed for delivery through the oral mucosa.

Oral transmucosal delivery offers a number of advantages in that it can provide a shorter onset time to maximal plasma concentration ($C_{max}$) than oral delivery, in particular for lipophilic drugs. This is because the drug rapidly passes directly and efficiently through the epithelium of the highly vascularized mucosal tissue to the plasma, thus rapidly reaching the circulation while avoiding slower, often inefficient and variable GI uptake. It is therefore advantageous for a drug to be delivered through the mucous membranes of the oral cavity, (e.g., via the sublingual route), when rapid onset, consistent $T_{max}$ and $C_{max}$ are advantageous.

In the process of oral transmucosal drug delivery, the drug is absorbed through the epithelial membranes of the oral cavity. However, frequently the key risk associated with oral transmucosal delivery is the enhanced potential for swallowing the medication owing to the continuous generation, backward flow and swallowing of the saliva. This becomes a particular risk when the dosage forms employed are large enough to produce a significant saliva response, which, in turn, leads to swallowing of drug and/or loss of adherence of the dosage form to the oral mucosa.

Various solid dosage forms, such as sublingual tablets, troches, lozenges, lozenges-on-a-stick, chewing gums, and buccal patches have been used to deliver drugs via the oral mucosal tissue. Solid dosage forms such as lozenges and tablets have been used for oral transmucosal delivery of drugs such as nitroglycerin sublingual tablets.

Reproducible and effective drug delivery technology represents an area of active research, in particular, as it applies to controlled substances such as opioids like sufentanil.

The relevant art does not describe a solid drug dosage form for delivery of sufentanil to the oral mucosa, such as the sublingual space.

This is particularly relevant to the treatment of pain, more specifically, acute (e.g. post-operative), intermittent and breakthrough pain.

Therefore, a need exists for improved drug dosage forms, methods and systems for administration of an opioid, such as sufentanil (e.g., by patient-controlled administration), for treatment of pain.

The present invention addresses these needs.

BRIEF SUMMARY OF THE INVENTION

Disclosed herein are dosage forms for oral transmucosal administration of sufentanil to a subject wherein the dosage forms comprise from about 5 to about 100 micrograms (mcg) of sufentanil, and a bioadhesive material, wherein the bioadhesive material provides for adherence to the oral mucosa of the subject. In a specific embodiment, the adherence may be to the sublingual mucosa of the subject One embodiment of the invention may include a dosage form in the form of a tablet. In a specific embodiment, the dosage form may adhere to the oral mucosa of a patient. In another embodiment, the tablet may include one or inure pharmaceutically acceptable excipients.

In another specific embodiment of the present, the tablet may comprise about 5 µg to about 200 µg sufentanil or pharmaceutically acceptable salts thereof (expressed as the free base of sufentanil), 60-9.5 wt % of one or more bulking agents, 1-5 wt % of one or more hydrogel forming excipients, and 1-10 wt % of one or more lubricants, wherein: the tablet has a volume less than about 30 µL, and when said tablet is adhered to the oral mucosa of a patient during the period of drug delivery: a) at least 55% of drug in the tablet is delivered via the oral transmucosal route; b) at least 90% of drug delivered, as measured by plasma concentration is delivered via the oral transmucosal route; c) the tablet provides a mean $T_{max}$ of about 15 minutes to about 80 minutes; d) the tablet provides a mean $T_{max}$ with a coefficient of variation of less than 40%; and e) the tablet provides a dose-normalized mean $C_{max}$ of about 1.59-2.75 µg/mL, per mcg dosed.

In another specific embodiment, the tablet has a volume of about 10 µL. In another embodiment, the one or more bulking agents are selected from the group consisting of mannitol, di-calcium phosphate, and combinations thereof. In another embodiment, the one or more hydrogel forming excipients is hydroxypropylmethylcellulose. In another embodiment, the lubricant is selected from the group consisting of stearic acid, magnesium stearate, and combinations thereof. In another specific embodiment, the tablet may comprise one or more bulking agents selected from the group consisting of mannitol, di-calcium phosphate, and combinations thereof, hydroxypropylmethylcellulose as hydrogel forming excipient, one or more lubricants selected from the group consisting of stearic acid, magnesium stearate, and combinations thereof in another embodiment of the present invention, the tablets may include an amount of sufentanil or pharmaceutically acceptable salts thereof comprising about 5 µg, 10 µg, 15 µg, 20 µg, 30 µg, 40 µg, 50 µg, 60 µg, 70 µg, 80 µg, 100 µg or 120 µg (expressed as the free base of sufentanil). In a specific embodiment, the amount of sufentanil or pharmaceutically acceptable salts thereof may be about 15 µg (expressed as the free base of sufentanil). In another specific embodiment, the amount of sufentanil or pharmaceutically acceptable salts thereof may be about 20 µg (expressed as the free base of sufentanil). In another specific embodiment, the amount of sufentanil or pharmaceutically acceptable salts thereof may be about 30 μg (expressed as the free base of sufentanil)

In another embodiment; after the administration of the tablet to the subject, the tablet may provide a mean $T_{max}$ range of from about 30 minutes to about 70 minutes. In another embodiment, after the administration of the tablet to the subject, the tablet may provide a mean $T_{max}$ range of from about 35 minutes to about 60 minutes. In another embodiment, after the administration of the tablet to the subject, the tablet may provide a mean $T_{max}$ range of from about 40 minutes to about 55 minutes. In another embodiment, after the administration of the tablet to the subject, the tablet may provide an area under the curve (AUC) with a coefficient of variation of less than about 30%. In another embodiment; after the administration of the tablet to the subject, the tablet may additionally provide a mean $T_{max}$, with a coefficient of variation of less than 30%. In another embodiment, after the administration of the tablet to the subject, at least 60% of the total amount of drug in the tablet may be absorbed via the oral transmucosal route, in another embodiment, after the administration of the tablet to the subject, at least 70% of the total amount of drug in the tablet may be absorbed via the oral transmucosal route. In another embodiment, after the administration of the tablet to the subject, at least 95% of the total amount of drug in the tablet may be absorbed via the oral transmucosal route.

In another embodiment, the oral transmucosal route may be through the sublingual membrane.

The present invention may include methods of administering the tablets above. In a specific embodiment, the methods may be for the treatment of pain in a patient in need thereof. In another specific embodiment, the tablet may be administered to a patient using a device.

BRIEF DESCRIPTION OF THE DRAWINGS

FIG. 22 shows the pharmacokinetic profile over a period of 6 hours. Treatment A was an IV infusion Sufenta® (5 mcg) and single dose triazolam (125 mcg) administered by the oral route; Treatment B was a single tablet containing 15 mcg sufentanil and 200 mcg triazolam administered by the sublingual route; Treatment C was a single tablet containing 15 mcg sufentanil administered by the sublingual route; Treatment D was a single tablet containing 15 mcg sufentanil administered by the buccal route; and Treatment E was three 15 mcg sufentanil tablets administered by the oral route (swallowed). The total 45 mcg dose administered in Treatment E is shown normalized to 15 mcg (mean/3).

DETAILED DESCRIPTION OF THE INVENTION

I. Introduction

Figure 1:
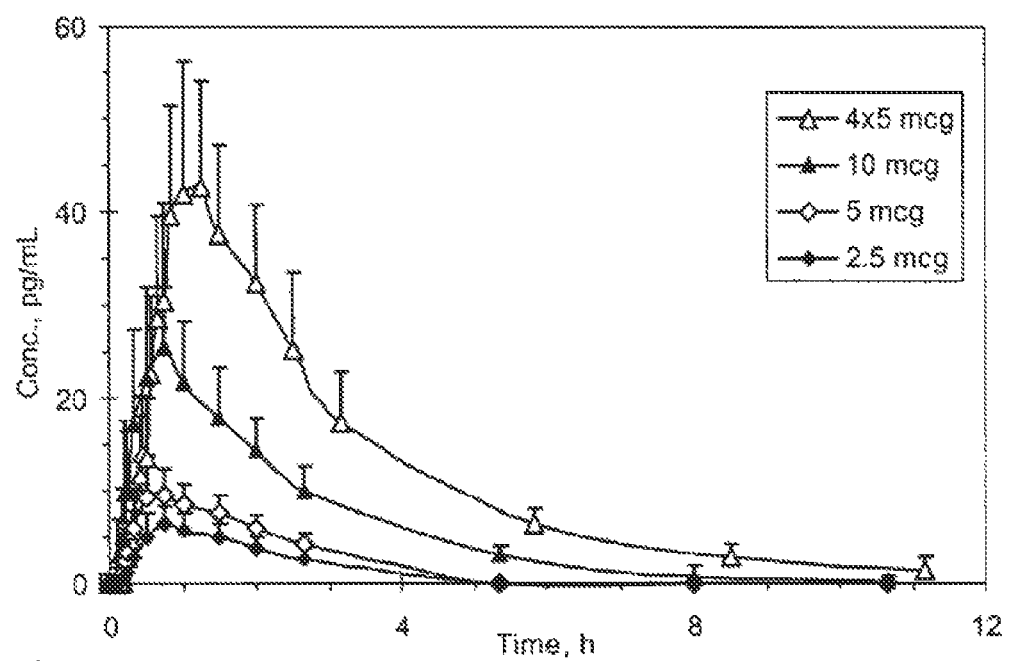
FIG. 1 is a graphic depiction of sufentanil plasma concentration mean±standard deviation (SD) versus time, following sublingual administration of 2.5, 5, 10 and 20 mcg (5 mcg every 10 minutes×4 doses) sufentanil dosage forms (slow-eroding) in healthy human volunteers.

Provided herein are compositions, methods, systems and kits for oral transmucosal administration of sufentanil-containing small volume dosage forms using a device. Oral transmucosal administration, such as sublingual administration of the small volume dosage forms disclosed herein, minimizes the saliva response and therefore minimizes delivery of the drug to the tract, such that the majority of drug is delivered across the oral mucosa. The small volume dosage forms have bioadhesive properties which facilitate adherence to the oral mucosa, thus minimizing the risk of ingestion and inefficient delivery due to swallowing.

The claimed small volume sufentanil-containing dosage forms offer a number of advantages in terms of both safety and efficacy as compared to currently available pain treatments.

The following disclosure provides a description of the dosage forms, devices, methods, systems and kits which constitute the invention. The invention is not limited to the specific dosage forms, devices, methodology, systems, kits or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug dosage forms and devices for containment, storage and delivery of such dosage forms.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

II. Definitions

The term "active agent" or "active" may be used interchangeably herein with the term "drug" and is meant to refer to any therapeutically active agent.

The term "adhere" is used herein with reference to a drug dosage form or formulation that is in contact with a surface such as a mucosal surface and is retained on the surface without the application of an external force. The term "adhere" is not meant to imply any particular degree of sticking or bonding, nor is it meant to imply any degree of permanency.

The term "analgesic drug" as used herein includes sufentanil or a sufentanil congener, such as alfentanil, fentanyl, lofentanil, carfentanil, remifentanil, trefentanil, or mirfentanil, as well as formulations comprising one or more therapeutic compounds. Use of the phrase "sufentanil or a congener" is not meant to be limiting to use of, or formulations comprising, only one of these selected opioid compounds. Furthermore, reference to sufentanil alone or to a selected sufentanil congener alone, e.g., reference to "alfentanil", is understood to be only exemplary of the drugs suitable for delivery according to the methods of the invention, and is not meant to be limiting in any way.

The term "AUC" as used herein means "area under the curve", and is also referred to as "$AUC_{inf}$" in a plot of concentration of drug in plasma versus time, AUC is typically given for the time interval zero to infinity, however, clearly plasma drug concentrations cannot be measured 'to infinity' for a patient so a mathematical equation is used to estimate the AUC from a limited number of concentration measurements.

$$AUC_{inf} = AUC_t + C_{last}/\lambda_Z, \text{ where } C_{last} \text{ was the last plasma concentration.}$$

In a practical sense, $AUC_{inf}$ represents the total amount of drug absorbed by the body, irrespective of the rate of absorption. This is useful when trying to determine whether two formulations of the same dose release the same dose of drug to the body. The $AUC_{inf}$ of a transmucosal dosage form compared to that of the same dosage administered intravenously serves as the basis for a measurement of bioavailability.

The term "bioadhesion" as used herein refers to adhesion to a biological surface mucosal membranes.

The term "bioavailability" or "F" as used herein means "percent bioavailability" and represents the fraction of drug absorbed from a test article as compared to the same drug when administered intravenously. It is calculated from the $AUC_{inf}$ of the test article following delivery via the intended route versus the $AUC_{inf}$ for the same drug after intravenous administration. The absolute bioavailability of sublingual administration was determined by the following formula:

$$F(\%) = \frac{AUC_{inf}^{sublingual}}{AUC_{inf}^{IV}} \times \frac{Dose_{IV}}{Dose_{sublingual}}$$

The term "breakthrough pain" as used herein, is a transitory flare of pain of moderate to severe intensity occurring on a background of otherwise controlled pain. "Breakthrough pain" can be intense for short periods of time, as short as 1 or 2 minutes or as long as 30 minutes or more.

The term "$C_{max}$" as used herein means the maximum observed plasma concentration following administration of a drug.

The term "congener" as used herein refers to one of many variants or configurations of a common chemical structure.

"Controlled drug delivery" refers to release or administration of a drug from a given dosage form in a controlled fashion in order to achieve the desired pharmacokinetic profile in viva. An aspect of "controlled" drug delivery is the ability to manipulate the formulation and/or dosage form in order to establish the desired kinetics of drug release.

"Sustained drug delivery" refers to release or administration of a drug from a given dosage form in a sustained fashion in order to achieve the desired pharmacokinetic profile in vivo.

The term "disintegration" is used interchangeably herein with "erosion" and means the physical process by which a dosage form breaks down and pertains to the physical integrity of the dosage form alone. This can occur in a number of different ways including breaking into smaller pieces and ultimately, fine and large particulates or, alternatively, eroding from the outside in, until the dosage form has disappeared.

The term "dissolution" as used herein means the process by which the active ingredient is dissolved from the tablet in the presence of a solvent, in vitro, or physiological fluids in vivo, e.g., saliva, irrespective of the mechanism of release, diffusion, erosion or combined erosion and diffusion.

The terms "d Y" "medication", "pharmacologically active agent" and the like are used interchangeably herein and generally refer to any substance that alters the physiology of an animal. A dosage from comprising a formulation of the invention may be used to deliver any drug that may be administered by the oral transmucosal route. The term "drug" as used herein with reference to a formulation of the invention means any "drug", "active agent", "active", "medication" or "therapeutically active agent" that can be effectively administered by the oral transmucosal route.

The term "drug" as applied to analgesia includes sufentanil or a sufentanil congener, such as alfentanil, fentanyl, lofentanil, carfentanil, remifentanil, trefentanil, or mirfentanil, as well as formulations comprising one or more therapeutic compounds. Use of "drug" or the phrase "sufentanil or a congener" is not meant to be limiting to use of, or formulations comprising, only one of these selected opioid compounds. Furthermore, reference to sufentanil alone or to a selected sufentanil congener alone, e.g., reference to "fentanyl", is understood to be only exemplary of the drugs suitable for delivery according to the methods of the invention, and is not meant to be limiting in any way.

The term "drug" may be used interchangeably herein with the term "therapeutic agent" or "medication". It will be understood that a "drug" formulation of the invention may include more than one therapeutic agent, wherein exemplary combinations of therapeutic agents include a combination of two or more opioid analogues, such as sufentanil plus an opioid such as fentanyl, alfentanil, lofentanil, carfentanil, remifentanil, trefentanil; or mirfentanil, or any other drug that might be administered in combination.

Reference to a specific drug herein means the free base of that drug, as well as pharmaceutically acceptable salts thereof. Thus, for example, "sufentanil" means the free base form of sufentanil, as well as salts of sufentanil, such as sufentanil citrate. Reference to a particular dose of a specific drug means that amount of the free base, or the molar equivalent amount of any salt form. Thus, for example, 5 mcg of sufentanil means 5 mcg of sufentanil free base, or equivalently 7.5 mcg of sufentanil citrate. Similarly, 5 mcg sufentanil "expressed as the free base of sufentanil" means 0.5 mcg of sufentanil free base, 7.5 mcg of sufentanil citrate, etc.

The term "erosion time" means the time required for a solid dosage form to break down until the dosage form has disappeared.

The term "formulation" or "drug formulation" or "dosage form" as used herein refers to a composition containing at least one therapeutic agent or medication for delivery to a subject. The dosage form comprises a given "formulation" or "drug formulation" and may be administered to a patient in the form of a lozenge, pill, tablet, capsule, membrane, strip, liquid, patch, film, gel, spray or other form.

As used herein, the term "hydrogel-forming preparation", means a solid formula ion largely devoid of water which upon contact with bodily fluids, and in particular those in the oral mucosa, is capable of absorbing water in such a way that it forms a hydrated gel in situ. The formation of the gel follows unique disintegration (or erosion) kinetics with sustained release of the drug over time, which occurs primarily by diffusion. Additionally, the term "hydrogel-forming preparation" describes a solid formulation largely devoid of water which upon contact with bodily fluids, and in particular those in the oral cavity, transforms into a film that releases the drug. Such films increase the surface area available for drug release and absorption thus enabling faster absorption of the drug.

The term "LogP" as used herein means logarithm of the ratio of equilibrium concentrations of un-ionized compound between octanol and water. P is also called the "octanol-water partition coefficient" and serves as a means to quantify the hydrophobicity or lipophilicity of, a chemical characteristic of a given drug.

The term "mucoadhesion" is used herein in to refer to the adhesion to mucosal membranes which are covered by mucus, such as those in the oral cavity and may be used interchangeably herein with the term "bioadhesion" which refers to adhesion to any biological surface.

The term "mucosal membrane" refers generally to any of the mucus-coated biological membranes in the body. Absorption through the mucosal membranes of the oral cavity is of particular interest. Thus, oral mucosal absorption, i.e., buccal, sublingual, gingival and palatal absorption is specifically contemplated.

The term "mucosal-depot" is used herein in its broadest sense to refer to a reservoir or deposit of a pharmaceutically active substance within or just beneath the mucosal membrane.

The term "non-ordered particulate mixture" or "non-ordered mixture" is used herein with reference to a formulation where the mixture is not ordered with respect to the pharmaceutically active agent and the bioadhesive material or bioadhesion promoting agent, or other formulation components. In addition, it is used herein with reference to any formulation prepared by a process that involves dry mixing wherein drug particles are not uniformly distributed over the surface of larger carrier particles. Such 'non-ordered' mixing may involve dry mixing of particles in a non-ordered fashion, where there is no requirement with respect to the order of addition/mixing of specific excipients with the drug, bioadhesive material or bioadhesion promoting agent and/or disintegrants. Further in the non-ordered mixing process, there is no limitation on the size of the drug particles. The drug particles may be larger than 25 μm. In addition, a "non-ordered mixture" includes any mixing processes in which the primary carrier particles do not incorporate a disintegrant within. Finally the "non-ordered mixture" may be prepared by any 'wet mixing' processes, i.e. processes in which a solvent or non-solvent is added during the mixing process or any mixing process in which the drug is added in a solution or suspension form.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "opioid naïve patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation) with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

The terms "oral transmucosal dosage form" and "dissolvable dosage form" may be used interchangeably herein and refer to a dosage form for use in practicing the present invention, which comprises a drug formulation as described herein. The oral transmucosal dosage form is typically a "sublingual dosage form", but in some cases other oral transmucosal routes may be employed. The invention relies upon such oral transmucosal dosage forms to provide sustained delivery of drugs across the oral mucosa; by controlling the formulation design immediate, intermediate and sustained release of drugs can be achieved, as described below. The dosage form is a substantially homogeneous composition which comprises active ingredients and one or more of mucoadhesives (also referred to herein as "bioadhesives") that provide for adherence to the mucosa of the mouth of a patient, binders for binding the excipients in a single tablet, one or more hydrogel-forming excipients, one or more bulking agents, one or more lubricants, as well as other excipients and factors that affect dissolution time or drug stability. The dissolvable drug formulations of the invention are neither effervescent nor do they comprise an essentially water-free, ordered mixture of microparticles of drug adhered to the surface of carrier particles, where the carrier particles are substantially larger than the microparticles of drug. In one aspect, the present invention provides small-volume oral transmucosal drug delivery dosage forms.

The terms "oral transmucosal drug delivery" and "oral transmucosal administration" as used herein refer to drug delivery that occurs substantially via the transmucosal route and not via swallowing followed by GI absorption. Maximal delivery occurs via the oral mucosa, typically by placement of the dosage form within the sublingual cavity.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "systems that include a drug dosage form and a dispensing device" as used herein refers to a drug dispensing system for delivery and/or monitoring of drug administration. The system may be used to monitor and deliver a pharmaceutically active substance, e.g., an opioid such as sufentanil, wherein the amount of drug delivered, corresponding efficacy and safety are enhanced over currently available systems. The system may have one or more features that provide for improved safety and ease of use over currently available systems including a security feature that prevents unauthorized access to the stored drugs, a dosing lock-out feature, a means for identifying an individual patient for controlled drug access, a dose counting feature, a memory means for retaining information about dose delivery, and an interface for bidirectional exchange of information with a user, a drug cartridge, or another device such as a computer.

The term "small volume drug dosage form" or "small volume dosage form" is used herein with reference to a small volume dosage form that has a volume of less than 100 μL, and a mass of less than 100 mg. More specifically, the dosage form has a mass of less than 100 mg, 90 mg, 80 mg, 70 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 μL, 90 μL, 80 μL, 70 μL, 60 μL, 50 μL, 40 μL, 30 μL, 29 μL, 28 μL, 27 μL, 26 μL, 25 μL, 24 μL, 23 μL, 22 μL, 21 μL, 20 μL, 19 μL, 18 μL, 17 μL, 16 μL, 15 μL, 14 μL, 13 μL, 12 μL, 11 μL, 10 μL, 9 μL, 8 μL, 7 μL, 6 μL or 5 μL. The "dosage form" may or may not have bioadhesive characteristics and may form a hydrogel upon contact with an aqueous solution.

The "dosage form" may be used to deliver any drug that can be administered by the oral transmucosal route in an amount amenable to administration via the small size of the dosage form, i.e. 0.25 μg to 99.9 mg, 1 μg to 50 mg or 1 μg to 10 mg.

The term "small volume sufentanil-containing drug dosage form" is used herein with reference to a small volume dosage form that contains a dose of sufentanil selected from about 2 micrograms (meg or mg) to about 200 mcg of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

The term "solid dosage form" or "solid drug dosage form" is used herein with reference to a small volume dosage form that is a solid, e.g., a lozenge, a pill, a tablet, a membrane or a strip.

The term "sublingual", means literally "under the tongue" and refers to administering a drug dosage form via the mouth in such a way that the pharmaceutically active substance is rapidly absorbed via the blood vessels under the tongue rather than via the digestive tract. Absorption occurs via the highly vascularized sublingual mucosa and allows the pharmaceutically active substance more direct access to the blood circulation, providing for direct systemic administration independent of (31 influences.

The term "terminal half-life" or "t/1;2, [h]" as defined herein is calculated as $\ln(2)/\lambda_z$ (defined as the first order terminal rate constant estimated by linear regression of the time versus log concentration curve) and also determined after the final dosing in repeated dose studies.

The term "$T_{max}$" as used herein means the time point of maximum observed plasma concentration.

The term "$T_{onset}$" as used herein means the observed "time of onset" and represents the time required for the plasma drug concentration to reach 50% of the maximum observed plasma concentration, $C_{max}$.

The term "therapeutically effective amount" means an amount of a therapeutic agent or a rate of delivery of a therapeutic agent (e.g., amount over time), effective to facilitate a desired therapeutic effect, such as pain relief. The precise desired therapeutic effect (e.g., degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

The term "Therapeutic Time Ratio" or "TTR" represents the average time that the drug is present at therapeutic levels, defined as time within which the drug plasma concentration is maintained above 50% of $C_{max}$, normalized by the drug's elimination half-life and it is calculated by the formula: TTR= (Time above 50% of $C_{max}$)/(Terminal intravenous elimination half-life of the drug). The last term is obtained from literature data for the drug of interest in the appropriate species.

The term "transmucosal" delivery of a drug and the like is meant to encompass all forms of delivery across or through a mucosal membrane. In particular, "oral transmucosal" delivery of a drug includes delivery across any tissue of the mouth, pharynx, larynx, trachea, or upper gastrointestinal tract, particularly including the sublingual, gingival and palatal mucosal tissues.

III. Formulations of the Invention

A formulation of the invention is a substantially homogeneous composition which comprises 0.01-99% weight/weight (w/w), 0.05% to 99%, 0.01% to 50% and 0.1% to 10% w/w of the active ingredient(s) (drug, medication, etc.) and one or more of mucoadhesives (also referred to herein as "bioadhesives") that provide for adhesion of the dosage forms of the present invention to the mucosa of the mouth of a patient. The formulations of the invention optionally further comprise one or more of the following: one or more binders that provide binding of the excipients in a single tablet; one or more hydrogel-forming excipients; one or more bulking agents; one or more lubricants; one or more glidants; one or more solubilizers; one or more surfactants; one or more flavors; one or more disintegrants; one or more buffering excipients; one or more coatings; one or more sustained release modifiers; and one or more other excipients and factors that modify and control the drug's dissolution or disintegration time and kinetics or protect the active drug from degradation.

A pharmaceutical dosage form of the invention for oral transmucosal delivery may be solid or non-solid. In one preferred embodiment, the dosage from is a solid that transforms into a hydrogel following contact with saliva. In another preferred embodiment, the dosage form is a solid that transforms into a bioadhesive film upon contact with saliva.

Excipients include substances added to the formulations of the invention which are required to produce a quality product, include, but are not limited to: bulking agents, binders, surfactants, bioadhesives, lubricants, disintegrants, stabilizers, solubilizers, glidants, and additives or factors that affect dissolution or disintegration time.

Excipients are not limited to those above. Other suitable nontoxic pharmaceutically acceptable carriers for use in oral formulations can be found in Remington's Pharmaceutical Sciences, 17th Edition, 1985.

The formulations of the invention for oral transmucosal drug delivery include at least one bioadhesive (mucoadhesive) agent or a mixture of bioadhesives to promote adhesion to the oral mucosa during drug delivery. In addition, the bioadhesive agents may also be effective in controlling the dosage form erosion time and/or, the drug dissolution kinetics over time when the dosage form is wetted by saliva. In addition, some of the mucoadhesives named in this invention may also serve as binders in the formulation to provide necessary bonding to the dosage form.

Exemplary mucoadhesive or bioadhesive materials are selected from the group consisting of natural, synthetic or biological polymers, lipids, phospholipids, and the like. Examples of natural and/or synthetic polymers include cellulosic derivatives (such as methylcellulose, carboxymethyl cellulose, hydroxyethyl cellulose, hydroxyethylmethyl cellulose, microcrystalline cellulose, etc), natural gums (such as guar gum, xanthan gum, locust bean gum, karaya gum, veegum etc), polyacrylates (such as Carbopol, polycarbophil, etc), alginates, thiol-containing polymers, polyoxyethylenes, polyethylene glycols (PEG) of all molecular weights (preferably between 1000 and 40,000 Da, of any chemistry, linear or branched), dextrans of all molecular weights (preferably between 1000 and 40,000 Da of any source), block copolymers, such as those prepared by combinations of lactic & glycolic acid (PLA, PGA, PLA of various viscosities, molecular weights and lactic-to-glycolic acid ratios) polyethylene glycol-polypropylene glycol block copolymers of any number and combination of repeating units (such as Pluronics, Tektronix or Genapol block copolymers), combination of the above copolymers either physically or chemically linked units (for example PEG-PLA or PEG-PLGA copolymers) mixtures. Preferably the bioadhesive material is selected from the group of polyethylene glycols, polyoxyethylenes, polyacrylic acid polymers, such as Carbopols (such as Carbopol 71G, 934P, 971P 974P) and polycarbophils (such as Noveon AA-1, Noveon CA-1, Noveon CA-2), cellulose and its derivatives and most preferably it is polyethylene glycol, Carbopol, and/or a cellulosic derivative or a combination thereof.

The mucoadhesive/bioadhesive excipient is typically present at 1-50% w/w, preferably 1-40% w/w or most preferably between 2-30% w/w. A formulation of the invention may contain one or more different bioadhesives in any combination.

The formulations of the invention for oral transmucosal drug delivery also include a binder or mixture of two or more binders which facilitate binding of the excipients into a single dosage form. Exemplary binders are selected from the group consisting of cellulosic derivatives (such as methylcellulose, carboxymethyl cellulose, hydroxyethyl cellulose, hydroxyethylmethyl cellulose, etc), polyacrylates (such as Carbopol, polycarbophil, etc), Povidone (all grades), Polyox of any molecular weight or grade, irradiated or not, starch, polyvinylpyrrolidone (PVP), Avicel, and the like.

The binder is typically present at 0.5-60% w/w, preferably 1-30% w/w and most preferably 1.5-15% w/w.

In one embodiment, the formulations of the invention for oral transmucosal drug delivery also include at least one hydrogel-forming excipient. Exemplary hydrogel-forming excipients are selected from the group consisting of polyethylene glycols and other polymers having an ethylene glycol backbone, whether homopolymers or cross-linked heteropolymers, block copolymers of ethylene glycol units, such as polyethylene oxide homopolymers (such as Polyox N10/MW=100,0001 Polyox-80/MW-200,000; Polyox 1105/MW-900,000; Polyox-301/MW=4,000,000; Polyox-303/MW=7, 000,000, Polyox WSR-N-60K, all of which are trade names of Union Carbide), hydroxypropylmethylcellulose (HPMC) of all molecular weights and grades, Poloxamers (such as Lutrol F-68, Lutrol F-127, F-105 etc, all trade names of BASF Chemicals), Genapol, polyethylene glycols (PEG, such as PEG-1500, PEG-3500, PEG-4000, PEG-6000, PEG-8000, PEG-12000, PEG-20,000, etc.), natural gums (Xanthan gum, Locust bean gum, etc) and cellulose derivatives (HC, HMC, HMPC, HPC, CP, CMC), polyacrylic acid-based polymers either as free or cross-linked and combinations thereof, biodegradable polymers such as poly lactic acids, polyglycolic acids and any combination thereof, whether a physical blend or cross-linked. In an embodiment, the hydrogel components may be cross-linked. The hydrogel-forming excipient(s) are typically present at 0.1-70% w/w, for example 1-50% w/w, 1-30% w/w, or 1.0-5.0% w/w.

The formulations of the invention for oral transmucosal drug delivery may also include at least one sustained release modifier which is a substance that upon hydration of the dosage form will preferentially interact with the drug in a physical or molecular level and thus reduce the rate of its diffusion from the transmucosal dosage form. Such excipients may also reduce the rate of water uptake by the formulation and thus enable a more prolonged drug dissolution and release from the tablet. In one embodiment, such sustained release modifiers are capable of binding molecularly to the active via physical (and therefore reversible) interactions, thus increasing the effective molecular weight of the active and thus further modifying their permeation (diffusion) characteristics through the epithelial and basal membranes of the sublingual mucosa. Such binding is reversible in nature and does not involve any chemical modifications of the active, thus it does not affect in any way its pharmacological action. In another preferred embodiment, such sustained release modifiers upon hydration may form discrete structures that may spontaneously entrap the drug and thus further prolong its action. Exemplary sustained release modifiers are selected from the group consisting of lipids, phospholipids, sterols, surfactants, polymers and salts. In general, the selected excipients) are lipophilic and capable of naturally form complexes with hydrophobic or lipophilic drugs. The degree of association of the release modifier(s) and the drug can be varied by altering the modifier-to-drug ratio in the formulation. In addition, such interaction may be appropriately enhanced by the appropriate combination of the release modifier with the active drug in the manufacturing process. Alternatively, the sustained release modifier may be a charged polymer either synthetic or biopolymer bearing a net charge, either positive or negative, and which is capable of binding to the active via electrostatic interactions thus modifying both its diffusion through the tablet and/or the kinetics of its permeation through the mucosal surface. Similarly to the other compounds mentioned above, such interaction is reversible and does not involve permanent chemical bonds with the active.

A sustained release modifier may typically be present at 0-80% w/w for example 1-20% w/w, or 1-10% w/w.

Such sustained release modifiers may further create pockets or microdomains dispersed throughout the swollen network of the hydrogel. These pockets can serve as reservoirs for drug compounds, as they will tend to decrease the driving force for diffusion by reducing the concentration of the drug solute in the bulk of the hydrogel. The hydrogel matrix along with the sustained release modifiers may be selected and designed such that drug release from the microdomains occurs slowly enough to enable the sustained dissolution of the drug from the dosage form.

The formulations of the invention for oral transmucosal drug delivery also include at least one filler (bulking agent). Exemplary bulking agents are selected from the group consisting of lactose USP, Starch 1500, mannitol, sorbitol, maltodextrin, malitol or other non-reducing sugars; microcrystalline cellulose (e.g., Avicel), dibasic calcium phosphate (anhydrous or dihydrate), sucrose, etc. and mixtures thereof. The filler/bulking agent is typically present at 20-95% w/w, for example 40-80% w/w, or 60-95%.

The formulations of the invention for oral transmucosal drug delivery may also include at least one solubilizing agent(s). Such agents are beneficial to improve the solubility of the active drug and enhance its absorption characteristics, but also facilitate handling and manufacturing. Appropriate solubilizers may include cyclodextrins, pH adjusters, salts and buffers, surfactants, fatty acids, phospholipids, metals of fatty acids etc. Exemplary surfactants are selected from the group consisting of ionic (sodium lauryl sulfate, etc), non-ionic such as polysorbates (Tweet) and Span surfactant series, Poloxamers, etc.), bile salts (such as sodium taurocholate, sodium taurodeoxycholate, sodium starch glycolate, sodium glycodeoxycholate, sodium glycocholate, etc), various alkyl glycosides, fatty acids, phosphatidylcholines, triglycerides, sphingolipids, glycosylated lipids, PEGylated lipids and mixtures thereof and may be present at 0.01-5% w/w. Exemplary metal salts and buffers may include at least of either organic (acetate, citrate, tartrate, etc) or inorganic (phosphate, carbonate, bicarbonate, borate, sulfate, sulfite, bisulfite, metabisulfite, chloride, etc.) salts of metals such as sodium, potassium, calcium, magnesium, etc), Further, combinations of one or more of such salts may be used to ensure adequate stabilization of the drug in the dosage form and may be present in the formulation at 0.1-20% w/w, preferably between 1-10% w/w. Exemplary pH adjusters include hydrochloric acid, acetic acid, phosphoric acid, sodium hydroxide, ammonium hydroxide and the like and may be present in the formulation between 0.1-5% w/w.

The formulations of the invention for oral transmucosal drug delivery also include at least one lubricant. Lubricants have several functions including preventing the adhesion of the tablets to the compression equipment and in some cases improving the flow of the granulation prior to compression or encapsulation. Lubricants are in most cases hydrophobic materials. Exemplary lubricants are selected from the group consisting of stearic acid and divalent cations of, such as magnesium stearate, calcium stearate, etc., talc, glycerol monostearate and the like. The lubricant is typically present at 0.01-10% w/w, for example between 0.1-3% w/w, or 1.0-10%.

The formulations of the invention for oral transmucosal drug delivery may also include at least one glidant. Glidants are substances that improve the flow characteristics of the blended or granulated material from the hopper into the feeding mechanism and ultimately, in the tablet die. Exemplary glidants are selected from the group comprising colloidal silicon dioxide, precipitated silicon dioxide, fumed silica (CAB-O-SIL M-5P, trademark of Cabot Corporation), stearowet and sterotex, silicas (such as SILOID and SILOX silicas—trademarks of Grace Davison Products, Aerosil—trademark of Degussa Pharma), higher fatty acids, the metal salts thereof, hydrogenated vegetable oils and the like. The glidant is typically present at 0.01-20% w/w, preferably between 0.1-5% w/w.

The formulation may also contain flavors or sweeteners and colorants such as aspartame, mannitol, lactose, sucrose, other artificial sweeteners; ferric oxides and FD&C lakes.

The formulation may also contain additives to help stabilize the drug substance from chemical of physical degradation. Such degradation reactions may include oxidation, hydrolysis, aggregation, deamidation, etc. Appropriate excipients that can stabilize the drug substance may include anti-oxidants, anti-hydrolytic agents, aggregation-blockers etc. Anti-oxidants may include BHT, BHA, vitamins, citric acid, EDTA, sodium bisulfate, sodium metabisulfate, thiourea, amino acids such as methionine, etc. Aggregation blockers may include surfactants, amino-acids, such as arginine, glycine, histidine, methionine etc. Additional excipients that may help protect the active against degradation are salts, pH adjusters, chelating agents and buffers in the dry or solution form. A number of salts may include all those known in the art and may be found in Remington's Pharmaceutical Sciences, 17th Edition, 1985. Exemplary pH adjusters include hydrochloric acid, acetic acid, phosphoric acid, sodium hydroxide, ammonium hydroxide and the like. Examples of such chelating agents include polylysine of different molecular weights, disodium edetate, sodium citrate, condensed sodium phosphate and the like. Examples of salts and buffers may include at least of either organic (acetate, citrate, tartrate, etc) or inorganic (phosphate, carbonate, bicarbonate, borate, sulfate, sulfite, bisulfite, metabisulfite, chloride, etc.) salts of metals such as sodium, potassium, calcium, magnesium, etc), Further, combinations of one or more of such salts may be used to ensure adequate stabilization of the drug in the dosage form. Stabilizing excipients may be present at 0.01-15% w/w in the formulation, for example between 0.1-5% w/w.

The formulation may also contain surfactants to increase wetting of the tablet, especially if faster release kinetics are desired, which can result in faster initiation of mucoadhesion. Such surfactants are generally present from 0.01 to 3% weight percent of the composition. Exemplary surfactants are selected from the group consisting of ionic (sodium lauryl sulfate, etc), non-ionic such as polysorbates (Tween and Span surfactant series), bile salts (such as sodium taurocholate, sodium taurodeoxycholate, sodium glycodeoxycholate, sodium glycocholate, etc), various alkyl glycosides, fatty acids, phosphatidylcholines, triglycerides, sphingolipids, glycosylated lipids, PEGylated lipids and mixtures thereof.

A dosage form of the invention may additionally comprise one or more excipients that may affect both tablet disintegration kinetics and drug release from the tablet, and thus pharmacokinetics. Such disintegrants are known to those skilled in the art and may be selected from a group consisting of starch, carboxy-methycellulose type or crosslinked Polyvinyl Pyrrolidone (such as cross-povidone, PVP-XL), alginates, cellulose-based disintegrants (such as purified cellulose, methylcellulose, crosslinked sodium carboxy ethylcellulose (Ac-Di-Sol) and carboxy methyl cellulose), low substituted hydroxypropyl ethers of cellulose, microcrystalline cellulose (such as Avicel), ion exchange resins (such as Ambrelite IPR 88), gums (such as agar, locust bean, karaya, Pectin and tragacanth), guar gums, gum Karaya, chitin and chitosan, Smecta, gellan gum, Isapghula Husk, Polacrillin Potassium (Tulsion[339]), gas-evolving disintegrants (such as citric acid and tartaric acid along with the sodium bicarbonate, sodium carbonate, potassium bicarbonate or calcium carbonate), sodium starch glycolate (such as Explotab and Primogel), starch DC and the likes. Addition of such additives facilitates the fast disintegration (or erosion) of the tablet into smaller pieces that erode more rapidly. An additional benefit of inclusion of such disintegrants in the formulations of the present invention is that the smaller, drug-containing particles formed upon disintegration have, by virtue of the highly increased surface area of contact with the oral mucosa, superior bioadhesive properties. In addition, the increased surface area may further facilitate the fast release of the active substance and thus further accelerate drug absorption and attainment of the required therapeutic levels systemically. However, as described above, such disintegrants are used at a low % w/w level in the solid dosage form, typically 1-30% w/w relative to the total weight of the dosage unit, preferably 5-25% w/w.

In one aspect of the invention, the dosage forms may comprise one or more biodegradable polymers of any type useful for sustained drug release. Exemplary polymer compositions include polyanhydrides and co-polymers of lactic acid and glycolic acid, poly(dl-lactide-co-glycolide) (PLGA), poly-lactic acid) (PLA), poly(alycolic acid) (PGA), polyorthoesters, proteins, and polysaccharides.

One method of making a formulation of the invention includes the steps of weighing the drug and one or more of bioadhesives, binders, hydrogel forming excipients, bulking agents, lubricants or glidants and factors that affect dissolution time, possibly powder grinding, dry powder mixing and tableting via direct compression. Alternatively, a wet granulation process may be used. Such a method (such as high shear granulation process) involves mixing the active drug and possibly some excipients in a mixer. The binder may be added in the mix dry or dissolved in the fluid used for granulation. The granulating solution or suspension is added to the dry powders in the mixer and mixed until the desired characteristics are achieved. This usually produces granules of suitable characteristics for producing dosage forms with adequate dissolution time, content uniformity, and other physical characteristics. After the wet granulation step, the product is most often dried and/or then milled after drying to get a major percentage of the product within a desired size range. Sometimes, the product is dried after being wet-sized using a suitable device, such as an oscillating granulator or a mill. The dry granulation mix may then be processed to get an acceptable size range by first screening with a sieving device, and then milling the oversized particles. In some instances, an appropriate glidant is added to improve the flow properties of the granules; suitable glidants, as described above.

A formulation of the invention may be manufactured by alternative granulation processes, all known to those skilled in the art, such as spray fluid bed granulation, extrusion and spheronization or fluid bed rotor granulation.

A bioadhesive tablet may be made using a formulation of the invention by coating a primary tablet with suitable coatings known in the art. Such coatings are meant to protect the active cores against damage (abrasion, breakage, dust formation) against influences to which the cores are exposed during transport and storage (atmospheric humidity, temperature fluctuations), and naturally these film coatings can also be colored. The sealing effect of film coats against water vapor is expressed by the water vapor permeability. Coating may be performed by one of the well known processes such as Würster coating, dry coating, film coating, fluid bed coating, pan coating, etc. Typical coating materials include polyvinyl pyrrolidone (PVT), polyvinyl pyrrolidone vinyl acetate copolymer (PVPVA), polyvinyl alcohol (PVA), polyvinyl alcohol/polyethylene glycol copolymer (PVA/PEG), gellan gum, maltodextrin, methyl cellulose, hydroxylpropyl methyl cellulose (HPMC of all grades and molecular weights), carrageenan and the like.

In one embodiment, the tablet core of the present invention may be coated with a bioadhesive material, such as those defined above, to improve bioadhesion of the tablet in the sublingual cavity. In such design, an eroding or hydrogel core is designed and coated with the appropriate bioadhesive material. To further facilitate the process, appropriate disintegrants may be included in the core, as described above.

In another embodiment, the tablet core of the present invention may be coated with a moisture-resistant coating, such as hydrophobic polymers, including celluloses, etc., to create a barrier for moisture ingress in the tablet core and thus further protect moisture-sensitive drugs. In addition, such water-resistant coat may improve the tablet behavior during manufacture by reducing its growth upon exposure to high % RH (relative humidity) environments, etc. A number of coating materials can be used to improve the moisture resistance of the tablet such as EUDRAGIT® E PO, Opadry® AMB, starch acetate and the like. Of particular interest in this application are coating materials that have very limited water uptake in <85% RH, yet rapidly absorb water at >85% RH. Such a function would facilitate wetting of the dosage form in the sublingual environment yet protect the dosage form under typical storage and moderate % RH conditions.

It will be understood that the formulation will be converted into a dosage form for delivery to a subject using procedures routinely employed by those of skill in the art. The process for preparation of the dosage form is optimized in order to achieve high dose content uniformity, which is particularly important for the potent compounds, which are generally present in mass ratios of 0.01-10% w/w.

Many methods of making dosage forms for use in the invention are known in the art and may be employed in practicing the present invention, such as direct compression, wet granulation, etc. In preparing a small tablet, such as a NanoTab®, it has been shown that erosion time and adhesion are independent of tableting force between 2-500K psi.

The dosage forms of the invention are adapted to adhere to the oral mucosa during the period of drug delivery, and until most or all of the drug has been delivered from the dosage form via the oral mucosa.

The dosage form of the current invention is further designed to enable sustained disintegration of the dosage over a time period after application in an oral mucosal cavity in vivo. The dosage forms of this invention may be designed to erode within 30 seconds—8 hours after administration. Further, they are designed to provide a range of disintegration rates, from linear to biphasic over the entire duration of the process.

In addition, the oral transmucosal dosage forms of this invention are designed to sustain and control the release (dissolution) of the drug from the dosage form after application to the oral mucosa in vivo or in vitro. The drug dissolution from these sustained-release transmucosal dosage forms can follow first or second order dissolution kinetics which can be manipulated to achieve the optimal in vivo pharmacokinetic profile and pharmacological action.

In certain embodiments of the invention, the drug dosage form is adapted to deliver 30% or more of the total amount of drug contained in a single drug dosage form to an individual via the oral mucosa. In other embodiments the percentage of the total amount of drug contained in a single drug dosage delivered transmucosally may be greater than 30-40%, 40-50%, 60-70%, 70-80%, 80-90% and preferably greater than 95%. In exemplary embodiments, at least 35%, 40%, 45%, 50%, 55%, 60%, 65%, 70%, 75%, 80%, 85%, 90%, 95%, 98% or 99%, of the total amount of drug contained in a single drug dosage form is delivered via the oral mucosa.

In certain embodiments of the invention, the drug dosage form is adapted to deliver no more than 60% of the total amount of drug contained in a single drug dosage form to an individual via the GI tract. In other embodiments the percentage delivered via the GI tract maybe lower, such that not more than 50%, 40%, 30%, 20%, 10%, 5% or 1% of the total amount of drug contained in the drug dosage form is delivered to the individual via the GI tract.

The delivery of a greater percentage (and amount) of drug via the oral mucosa and the corresponding lack of delivery via the GI tract provides a significant improvement over prior methods of drug delivery.

One preferred site for drug delivery is the sublingual area, although in certain embodiments it may be advantageous for the dosage form to be placed inside the cheek, or to adhere to the roof of the mouth or the gum.

Minimizing the saliva response produces a delivery profile that is consistent and predictable from patient to patient, which is not the case with oral lozenge formulations that produce a significant saliva response. A reduced saliva response is particularly important for drugs with poor bioavailability through the GI tract.

Sublingual delivery is preferred as the sublingual mucosa is more readily permeable to medications than other mucosal areas, such as the buccal mucosa, resulting in more rapid uptake (Shojaei A H, et al. Buccal mucosa as a route for systemic drug delivery: a review. Journal of Pharmacy and Pharmaceutical Sciences. 1:15-30, 1998).

The formulations of the invention also provide improved dissolution profiles over previous oral or oral transmucosal formulations, efficacious delivery of drug via the oral mucosa, and a consistent plasma level within the therapeutic window.

The decreased swallowing of drug and more consistent uptake of oral transmucosal dosage forms made using the formulations of the present invention result in peak plasma levels that are more consistent between individual dosages as compared to those using commercially available formulations.

Dosage forms comprising a formulation of the present invention are designed to work effectively in the unique environment of the oral cavity such that a limited amount of fluid, the relatively short period of time for drug delivery, and the pH levels within the oral cavity do not adversely affect absorption of the drug. The formulations are also designed to improve dissolution, solubility, and stability of the drug dosage form. The advantages of the present invention contribute to the ability of the drug formulation to provide higher levels of drug absorption via the oral transmucosal route and consistent dose-to-effect times, making the present formulation a significant improvement for the treatment of acute or breakthrough pain.

The formulations of the present invention are designed to avoid the high peak plasma levels of IV formulations by controlling both tablet disintegration (or erosion) and drug dissolution and release from the tablet to enable more consistent delivery. The formulations of the present invention may be used to provide single or individual, repetitive doses that include a defined amount of the active agent, thereby allowing the patient to accurately titrate the amount of drug delivered and to adjust the amount as appropriate in a safe and effective manner.

The advantage of the sustained-release oral transmucosal formulations described in this invention is that they can maintain the plasma drug concentration within a targeted therapeutic window for a longer duration than either IV or immediate-release oral formulations, whether solid dosage forms or liquid-based dosage forms. The high peak plasma levels typically observed for such conventional immediate release formulations are blunted by the sustained release of the drug. In addition, a rapid decline in plasma levels is avoided since the drug will continually cross through the oral cavity into the systemic circulation during the entire process of tablet dissolution, thus providing plasma pharmacokinetics with a more stable plateau. In addition, the dosage forms described in this invention may improve treatment safety by minimizing the potentially deleterious side effects due to the reduction of the peaks and troughs in the plasma drug pharmacokinetics, which compromise treatment safety and efficacy.

The oral transmucosal bioadhesive formulations of the present invention are typically designed to disintegrate (or totally erode) from within 30 seconds up to 1 minute, 2 minutes, 3 minutes, 4 minutes, 5 minutes, 10 minutes, 15 minutes, 30 minutes, 1 hour, 2 hours, 4 hours, 8 hours or longer dependent upon the patient and circumstances of drug administration as well as the intrinsic drug pharmacokinetics. It will be understood that the composition of the oral transmucosal formulations of the present invention may be adjusted to provide both a range of doses and a range of dissolution times to fit particular clinical situations.

Dissolution times for sublingual administration of the formulations of the invention will vary from 30 seconds up to 1 minute, 2 minutes, 3 minutes. 4 minutes, 5 minutes, 10 minutes, 15 minutes, 30 minutes, 1 hour, 2 hours, 4 hours, 8 hours or longer.

The oral transmucosal dosage forms of invention are designed to fit comfortably under the tongue such that the drug form disintegrates sufficiently slowly to avoid the immediate peak plasma levels followed by significant, drop off seen in prior art formulations such as described in U.S. Pat. No. 6,759,059, wherein fentanyl was administered via tablets containing 400 µg of fentanyl which resulted in a peak plasma level of 2.5 ng/ml at 5 minutes post-administration, followed by an immediate drop in plasma level.

The formulations of the present invention will be provided in a number of dosage forms that vary according to the nature and amount of active ingredients while maintaining the features of the formulations of the invention for dissolution in the oral cavity such that a greater percentage of drug absorption takes place via the oral mucosal route and not the GI route.

In one aspect of the invention, when a homogeneous dosage form comprising a formulation according to the present invention is placed in the sublingual cavity, for example under the tongue on either side of the frenulum linguae, it adheres upon contact. While not wishing to be bound by theory, it appears that when a dosage form comprising a formulation of the invention is exposed to the moisture of the sublingual space the dosage form absorbs water, resulting in the formation of a hydrogel network. In a preferred embodiment, the hydrogel formulation is designed to form a film which is visible in the sublingual space following tablet disintegration. Upon placement on the oral mucosa, the dosage form absorbs water such that upon full hydration, it spreads across the mucosal surface, thus transforming into a bioadhesive film containing the active drug. This transformation results in a significant increase of the surface area available for drug release, thus accelerating drug diffusion and release from the dosage form.

Hydrogel formation in the dosage forms of the invention takes place in the presence of certain hydrogel-enabling excipients that have the capacity to absorb water and form gels. Such excipients include Polyox of all grades, polyethylene glycols (of all grades), PEG-based copolymers, whether homopolymers or heteropolytners (such as Poloxamer, etc), Dextran, HPMC, starch, etc, as detailed above. In addition, any combination of such excipients may favor hydrogel formation upon contact with bodily fluids. In a certain embodiment of the present invention, combinations of such hydrogel forming excipients with excipients that do not favor gel formation (i.e., don't have such a capacity to swell), e.g., certain celluloses and the like also result in formation of hydrogel structures, albeit with a lower gelling capacity.

In another aspect of the invention, dosage forms referred to herein as "eroding-type" dosage forms are provided. Such "eroding-type" dosage forms, although they may absorb significant amounts of water (depending on their composition) they do not have the same capacity of swelling and do not form gels as described for the hydrogel type formulations defined above. These "eroding-type" formulations adhere to the sublingual cavity upon contact, similar to the hydrogel formulations. However, in contrast to hydrogels, they follow a surface-erosion mechanism without prior formation of a hydrated gel. As an "eroding-type" dosage form is exposed to the moisture of the sublingual space, the surface of the tablet hydrates and erodes thereby exposing the underlying layers; as the subsequent layers become hydrated they subsequently erode and so on, thus resulting in a continuous reduction in the size of the tablet.

In a preferred embodiment, such eroding formulations are designed to form a film which is visible in the sublingual space following tablet disintegration. Upon placement on the oral mucosa, the dosage form absorbs water such that upon full hydration, it spreads across the mucosal surface, thus transforming into a bioadhesive film containing the active drug. This transformation results in a significant increase of the surface area available for drug release, thus accelerating drug diffusion and release from the dosage form. Owing to the higher contact surface area, drug absorption occurs fast, resulting in fast onset of action.

Such eroding-type dosage forms are typically characterized by a lack of inclusion of hydrogel-forming excipients and in particular Polyox (of all grades) PEG-based copolymers, whether homopolymers or heteropolymers (such as Poloxamer, etc), HPMC, etc. However, it will be understood that the percentage w/w composition of the various components of the dosage form will impact the mechanism of erosion. For example, small amounts of particular hydrogel-enabling excipients may not induce formation of a hydrogel and as such, some hydrogel-enabling excipients may be included in eroding formulations without changing their erosion-based disintegration mechanism. It is both the combination of excipients and their percent weight composition that gives a hydrogel its capacity to maintain a structural matrix upon contact with an aqueous solution. Therefore, inclusion of a hydrogel-forming excipient in a given formulation will not necessarily induce "swelling" as with the typical hydrogel formulations. Both hydrogel-forming and eroding-type formulations of the invention provide control of the drug dissolution and/or in vivo absorption kinetics to enable enhanced bioavailability and improved efficacy.

The formulations of the invention find particular utility in pediatric applications, since the comfortable and secure nature of the dosage form will allow children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a inure rapid onset is required.

Similarly, the formulations of the invention find particular utility in geriatric applications, since the comfortable and secure nature of the dosage form will allow elderly patients to readily accept this mode of therapy and will reliably deliver drug transmucosally. Specific examples include, but are not limited to, treatment of nausea when a elderly patient can't swallow a pill, acute pain when IV access is not available or inconvenient, pre-procedural sedation when a patient is NPO (no oral intake allowed) or a more rapid onset is required, etc. The formulations of the invention find further utility in veterinary applications. Specific examples include, but are not limited to, any treatment of an acute condition for Which IV administration is not readily available or inconvenient, such as pain relief, anxiety/stress relief, pre-procedural sedation, etc.

IV. Drug Dosage Forms

The present invention provides oral transmucosal drug delivery dosage forms that produce a reduced saliva response when compared with other oral transmucosal dosage forms, thus providing high absorption and sustained absorption rates of the pharmaceutically active substance across the oral mucosa, and reduced delivery to the gastrointestinal tract in addition to offering a more reproducible means of delivery.

The oral transmucosal dosage form is typically a "sublingual dosage form", but in some cases other oral transmucosal routes may be employed. The oral transmucosal dosage form may also be a small volume dosage form. The small volume oral transmucosal drug dosage forms produce a reduced saliva response as compared with conventional, larger dosage forms that are intended to deliver a drug in the oral cavity.

The preferred site for oral transmucosal drug delivery is the sublingual area, although in certain embodiments it may be advantageous for the dosage form to be placed inside the cheek, or to adhere to the roof of the mouth or the gum.

Sublingual delivery is preferred as the sublingual mucosa is more readily permeable to medications than other mucosal areas, such as the buccal mucosa, resulting in more rapid uptake.

The dosage forms provide for the delivery of a greater percentage and amount) of the drug via the oral mucosa and a corresponding decrease in delivery via the gastrointestinal (GI) tract as compared to traditional oral dosage forms and other oral transmucosal dosage forms.

Typically, the dosage forms are adapted to adhere to the oral mucosa (i.e. are bioadhesive) during the period of drug delivery, and until most or all of the drug has been delivered from the dosage form to the oral mucosa.

More specifically, the dosage forms have a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or less than 5 mg; or a volume of less than 100 µL, 90 µL, 80 µL, 70 µL, 60 µL, 50 µL, 40 µL, 30 µL, 29 µL, 28 µL, 27 µL, 26 µL, 25 µL, 24 µL, 23 µL, 22 µL, 21 µL, 20 µL, 19 µL, 18 µL, 17 µL, 16 µL, 15 µL, 14 µL, 13 µL, 12 µL, 11 µL, 10 µL, 9µL, 8 µL, 7 µL, 6 µL or less than 5 µL.

In a preferred embodiment, the claimed dosage forms have a mass of less than 30 mg and a volume of less than 30 µL.

The dosage forms typically have bioadhesive characteristics and may form a hydrogel upon contact with an aqueous solution.

The dosage forms of the invention are adapted for oral transmucosal (for example sublingual) delivery of a drug and typically have an erosion time of from 5 seconds up to a time selected from 1 minute, 2 minutes, 3 minutes, 4 minutes, 5 minutes, 10 minutes, 15 minutes, 30 minutes, 1 hour, 2 hours, 4 hours and 8 hours or longer.

In embodiments, the dosage forms have an erosion time of from about 6 minutes or up to 25 minutes, however the erosion time may vary. More specifically, the dosage forms typically have an erosion time of about 5 minutes, 6 minutes, 7 minutes, 8 minutes, 9 minutes, 10 minutes, 11 minutes, 12 minutes, 13 minutes, 14 minutes, 15 minutes, 16 minutes, 18 minutes, 19 minutes, 20 minutes, 21 minutes, 22 minutes, 23 minutes, 24 minutes or 25 minutes.

The dosage forms may have essentially any shape, examples of which include a round disc with a flat, concave, or convex face, an ellipsoid shape, a spherical shape, a polygon with three or more edges and flat, concave, or convex faces. The dosage forms may be symmetrical or asymmetrical, and may have features or geometries that allow for controlled, convenient, and easy storage, handling, packaging or dosing.

Oral transmucosal drug delivery is simple, non-invasive, and can be accomplished by a caregiver or patient with minimal discomfort. A dosage form for oral transmucosal delivery may be solid or non-solid. In one preferred embodiment, the dosage from is a solid that turns into a hydrogel following contact with saliva. In another preferred embodiment, the dosage from is a solid that erodes without forming a hydrogel following contact with saliva.

Generally, oral transmucosal delivery of pharmaceutically active substances is achieved using solid dosage forms such as lozenges or tablets; however, liquids, sprays, gels, gums, powders, and films and the like may also be used.

For certain drugs, such as those with poor bioavailability via the GI tract, e.g., lipophilic opioids such as sufentanil, oral transmucosal delivery is a more effective delivery route than GI delivery. For such lipophilic drugs, oral transmucosal delivery has a shorter onset time (i.e., the time from administration to therapeutic effect) than does oral GI delivery and provides better bioavailability and more consistent pharmacokinetics.

The small size of the claimed drug dosage forms is designed to reduce the saliva response, thus reducing the amount of drug swallowed, and thereby delivering a substantial amount of drug to a subject via the oral mucosa. The claimed drug dosage forms provide for efficacious delivery of sufentanil via the oral mucosa and a consistent plasma level within the therapeutic window.

Formulations for preparation of the claimed dosage forms and methods of making them are described in U.S. application Ser. Nos. 11/825,251 and 11/650,227, expressly incorporated by reference herein. An exemplary formulation is bioadhesive and comprises from about 0.0004% to about 0.04% sufentanil, e.g., 0.0005%, 0.001%, 0.002%, 0.003%, 0.004%, 0.006%, 0.008%, 0.01%. 0.012%, 0.014% or 0.016% sufentanil. In general, the formulation comprises (a) a non-ordered mixture of a pharmaceutically active amount of a drug; (b) a bioadhesive material which provides for adherence to the oral mucosa of the subject; and (c) stearic acid, wherein dissolution of a dosage form comprising the formulation is independent of pH, e.g., over a pH range of about 4 to 8.

Numerous suitable nontoxic pharmaceutically acceptable carriers for use in oral dosage forms can be found in Remington's Pharmaceutical Sciences, 17th Edition, 1985.

It will be understood that the formulation is converted into a dosage form for delivery to a subject using procedures routinely employed by those of skill in the art, such as direct compression, wet granulation, etc. The process for preparation of the dosage form is optimized for each formulation in order to achieve high dose content uniformity.

While not wishing to be bound by theory, when a claimed dosage form is placed in the sublingual cavity, preferably under the tongue on either side of the frenulum linguae, it adheres upon contact. As the dosage form is exposed to the moisture of the sublingual space the dosage form absorbs water, resulting in erosion of the dosage form and release of the drug to the circulation of the subject.

IV. Pharmaceutically Active Agents for Use in Drug Dosage Forms of the Inventions In one embodiment of the invention, a formulation of the invention finds utility in delivery of any drug which can be formulated in a dosage form comprising a bioadhesive material and a predetermined amount of a pharmaceutically active agent in an amount selected from the group consisting of 10 mcg, 15 mcg, 25 mcg, 50 mcg, 100 mcg, 500 mcg, 1 mg, 2 mg, 3 mg, 4 mg, 5 mg, 6 mg, 7 mg, 8 mg, 9 mg and 10 mg.

The pharmaceutically active agent in a formulation of the invention need not be micronized.

In another embodiment of the invention, a formulation of the invention finds utility in delivery of any drug which can be formulated in a dosage form having an erosion time of from 5 seconds up to a time selected from the group consisting of 1 minute, 2 minutes, 3 minutes, 4 minutes, 5 minutes, 10 minutes, 15 minutes, 30 minutes, 1 hour, 2 hours, 4 hours and 8 hours or longer.

In still another embodiment of the invention, a formulation of the invention finds utility in delivery of any drug which can be formulated in a dosage form wherein a single or repeated oral transmucosal administration to a subject results in a bioavailability of greater than about 70%, 75%, 80%, 85%, 86%, 87%, 88%, 89%, 90%, 91%, 92%, 93%, 94%, 65%, 96%, 97%, 98% or 99%.

In yet another embodiment of the invention, a formulation of the invention finds utility in delivery of any drug which can be formulated in a dosage form wherein a single or repeated oral transmucosal administration to a subject results in a bioavailability with a coefficient of variation of less than 30%, less than 35% or less than 40%.

In yet another embodiment of the invention, a formulation of the invention finds utility in delivery of any drug which can be formulated in a dosage form wherein a single or repeated oral transmucosal administration to a subject results in a $C_{max}$ with a coefficient of variation of less than 30%, less than 35% or less than 40%.

In yet another embodiment of the invention, a formulation of the invention finds utility in delivery of any drug which can be formulated in a dosage form wherein a single or repeated oral transmucosal administration to a subject results in a $T_{max}$ of from about 5 minutes to about 2 hours.

In yet another embodiment of the invention, a formulation of the invention finds utility in delivery of any drug which can be formulated in a dosage form wherein a single or repeated oral transmucosal administration to a subject results in a plasma level that reaches 50% of $C_{max}$ in a time selected from about 3 minutes to 2 hours, from about 3 minutes to 30 minutes, from about 3 minutes to 20 minutes and from about 3 minutes to 10 minutes.

In yet another embodiment of the invention, a formulation of the invention finds utility in delivery of any drug which can be formulated in a dosage form wherein a single or repeated oral transmucosal administration to a subject results in a plasma half-life of from about 5 minutes and about 6 hours.

In yet another embodiment of the invention, a formulation of the invention finds utility in delivery of any drug which can be formulated in a dosage form wherein a single or repeated oral transmucosal administration to a subject results in a therapeutic time ratio of greater than 0.07 or from about 0.5 to about 2.0.

In yet another embodiment of the invention, a formulation of the invention is characterized by in vitro drug dissolution that is independent of the medium pH between pH 4.5-pH 8.0.

In yet another embodiment of the invention, a formulation of the invention can be delivered by appropriate single or multiple dose applicators or a device. Such applicators are capable of enabling accurate placement of the dosage forms of the present invention in the oral transmucosal cavity, and preferably the sublingual area.

Pharmaceutically active agents for use in a formulation of the invention are characterized by logarithm of the octanol-water partition coefficient (LogP) between 0.006 and 3.382.

Formulations of the Invention for the Suppression or Mitigation of Pain,

In one exemplary application, the formulations of the invention find utility in treating a subject suffering from pain that may be associated with any of a variety of identifiable or unidentifiable etiologies. The formulations of the invention find utility in suppression or mitigation of pain. The term "treatment" or "management" of pain is used here to generally describe regression, suppression, or mitigation of pain so as to make the subject more comfortable, as determined for example by pain score.

The term "acute pain" is used herein with reference to pain that is typically present for less than one month, however, in some cases pain that is present for as long as three months may also be considered to be "acute".

The term "chronic pain" is used herein with reference to pain that is typically present for longer than one month.

In one exemplary aspect, the invention relates to oral transmucosal delivery of a formulation for pain-relief comprising a drug such as an opioid or opioid agonist, for the treatment of acute or break-through pain.

In certain embodiments, a dosage form comprising a formulation of the invention contains at least 0.001% percent by weight of the active ingredient. Preferably, the dosage form comprises from about at least 0.005% to as much as 99.9% by weight, 0.05% to 99%, 0.01% to 50%, 0.1% to 10% of the active ingredient. In certain other embodiments, a dosage form comprising a formulation of the invention contains as much as 10 μg, 15 μg, 25 μg, 50 μg, 100 μg, 500 μg, 1 mg, 2 mg, 3 mg, 4 mg, 5 mg, 6 mg, 7 mg, 8 mg, 9 mg or 10 mg of the active ingredient or drug.

The percentage of active ingredient(s) will vary dependent upon the size of the dosage form and nature of the active ingredient(s), optimized to obtain maximal delivery via the oral mucosal route. In some aspects of the invention more than one active ingredient may be included in a single dosage form V. Sufentanil Opioids are widely used for the treatment of pain, and are generally delivered intravenously, orally, epidurally, transdermally, rectally and intramuscularly. Morphine and its analogues are commonly delivered intravenously and are effective against severe, chronic and acute pain. However, they can also have severe respiratory depressive effects if not used appropriately and also suffer from a high abuse potential. The predominant cause of morbidity and mortality from pure opioid overdoses is due to respiratory complications.

Sufentanil (N-[4-(Methoxymethyl-1-(2-(2-thienyl)ethyl)-4-piperidinyl)]-N-phenylpropanamide), is used as a primary anesthetic, to produce balanced general anesthesia in cardiac surgery, for epidural administration during labor and delivery and has been administered experimentally in both intranasal and liquid oral formulations. A commercial form of sufentanil used for IV delivery is the SUFENTA FORTE® formulation. This liquid formulation contains 0.075 mg/ml sufentanil citrate (equivalent to 0.05 mg of sufentanil base) and 9.0 mg/ml sodium chloride in water. It has a plasma elimination half-life of 148 minutes, and 80% of the administered dose is excreted in 24 hours.

The use of sufentanil clinically has predominantly been limited to IV administration in operating rooms or intensive care units. There have been a few studies on the use of liquid sufentanil preparations for low-dose intranasal administration (Helmers et al., 1989; Jackson K, et al., J Pain Symptom Management 2002: 23(6): 450-452) and case reports of sublingual delivery of a liquid sufentanil preparation (Gardner-Nix J., J Pain Symptom Management. 2001 August; 22(2): 627-30; Kunz K M, Theisen J A, Schroeder M E, Journal of Pain and Symptom Management, 8:189-190, 1993). In most of these studies, the smallest dosing of sufentanil in adults was 5 mcg in opioid naïve patients. Liquid administered to the oral or nasal mucosa suffers from lower bioavailability and possibly a shorter duration of action as demonstrated by the animal studies (sublingual liquid) described herein, as well as the literature (nasal liquid drops—Helmers et al., 1989). Gardner-Nix provides analgesic data (not pharmacokinetic data) produced by liquid sublingual sufentanil and describes the analgesic onset of liquid sublingual sufentanil occurring within 6 minutes but the duration of pain relief lasted only approximately 30 minutes. A number of opioid dosage forms many of which contain fentanyl are currently available for treatment of pain.

At the time of the present invention, two oral transmucosal fentanyl products had been approved for human use: fentanyl buccal tablet (Fentora) and Actiq® which is an oral transmucosal fentanyl lozenge. According to their respective package inserts, approximately 25% of the total dose of Actiq® and approximately 48% of the total dose of Fentora® is rapidly absorbed via the oral transmucosal route through the buccal mucosa; the remaining 75% of the total dose of Actiq®, and 50% of the total dose of Fentora® is swallowed with the saliva and slowly absorbed from the gastrointestinal (GI) tract.

A study further evaluated the bioavailability of Fentora® and Actiq® following both GI administration and transmucosal administration. Darwish et al., J. Clin. Pharmacol, ((47) 343-350, 2007). The observed GI bioavailability is 31% for a swallowed Fentora® tablet; the observed absolute bioavailability for oral transmucosal Fentora® is 65%. Dalwish at p. 347. The observed absolute bioavailability for oral transmucosal Actiq® is 47%. Darwish at p. 347.

The observed GI bioavailability for a swallowed sufentanil solid dosage form, however, is much lower. Indeed, Table 19 indicates that the (31 bioavailability of a swallowed sufentanil solid dosage in beagles is 12.2±16.3%. In another example, FIG. 22 indicates that GI bioavailability for a swallowed sufentanil solid dosage form in humans is 7%. Accordingly, the GI bioavailability of a swallowed sufentanil dosage form, such as a bioadhesive tablet, is significantly lower than the GI bioavailability of fentanyl. The opiod analgesics fentanyl and sufentanil have similar chemical structures, chemical properties, route of metabolism and mechanism of action. Thus, the much lower GI bioavailability of sufentanil was unexpected.

Fentora® and Actiq® also have wide $T_{max}$ ranges. Following transbuccal administration of fentanyl using a lozenge (e.g., Actiq®), the $T_{max}$ for the 200 mcg dosage of Actiq® ranges from 20-120 minutes resulting from erratic GI uptake due to the fact that 75% of the fentanyl is swallowed (Actiq® package insert). More recent publications on the $T_{max}$ of Actiq® indicate that these original times were skewed towards more rapid onset (Fentora® package insert indicates a range of $T_{max}$ for Actiq® for 35 up to 240 minutes). Fentora® (a fentanyl buccal tablet), also has a wide $T_{max}$ range; the Fentora® package insert indicates a range of $T_{max}$ of 20-240 minutes. In contrast to the claimed dosage forms, both Actiq® and Fentora® suffer from the disadvantage that substantial amounts of lozenge-administered fentanyl are swallowed by the patient.

As a result, the present inventors have found that unlike fentanyl-containing transbuccal dosage forms, and because swallowed sufentanil has such comparatively poor bioavailability in the gastrointestinal tract, it is important that sufentanil-containing transbuccal dosage forms be formulated to maximize transbuccal absorption and minimize swallowed sufentanil (e.g., as described herein by providing a very small dosage form which minimizes the saliva response, and which is bioadhesive to maximize contact with buccal tissues, thereby minimizing the amount of swallowed sufentanil, and maximizing transbuccal absorption).

Indeed, the present invention provides a small volume tablet and bioadhesive characteristics that generate a minimal saliva response, and thus minimizes the swallowing of sufentanil. In one embodiment, the tablet form adheres to the oral mucosa of a patient. In another embodiment of the present invention, most of sufentanil contained in the tablet may be absorbed via the oral transmucosal route. In one embodiment, the percentage of the total amount of sufentanil contained in a tablet delivered transmucosally may be greater than 30-40%, 40-50%, 60-70%, 70-80%, 80-90% and preferably greater than 95%. In exemplary embodiments, at least 35%, 40%, 45%, 50%, 55%, 60%, 65%, 70%, 75%, 80%, 85%, 90%, 95%, 98% or 99%, of the total amount of sufentanil contained in a tablet form is delivered via the oral transmucosal route. In a specific embodiment, at least 55% of the total amount of sufentanil contained in a tablet form is delivered via the oral transmucosal route.

In view of the surprisingly low GI bioavailability of sufentanil when swallowed (about 7%), the present invention also provides for an unexpectedly narrow $T_{max}$ range and low mean $T_{max}$, variability ($T_{max}$ coefficient of variation). Again, the small volume tablet and bioadhesive characteristics of the present invention allows for a consistent minimal saliva response, thus minimizing the amount of sufentanil swallowed and lost due to its extremely low GI bioavailability. The present invention thus provides a mean $T_{max}$ range that is significantly narrower than that of Actiq® (a range of $T_{max}$ of 35 up to 240 minutes) and Fentora® (a range of $T_{max}$ of 20-240 minutes). Indeed, the human studies provided below demonstrate that the administration of the tablets of the present invention with a 2.5 mcg dose of sufentanil provides a mean $T_{max}$ 43.8 minutes±7.8 minutes; a mean $T_{max}$ for a 5 mcg dose of sufentanil of 46.2 minutes±17.4 minutes; and a mean $T_{max}$ for a 10 mcg dose of sufentanil of 40.8 minutes±13.2 minutes (See Table 2). The human studies of sufentanil, when administered in another dosage form of the present invention (See Example 2B) also provide narrow $T_{max}$ ranges, wherein the mean $T_{max}$ for a 10 mcg dose of sufentanil is 50.4 minutes±21 minutes; and the mean $T_{max}$ for an 80 mcg dose of sufentanil is 53.4 minutes±21 minutes (See Table 4). Accordingly, the mean $T_{max}$ range of the present invention may be from, for example, about 15 minutes to about 80 minutes. In another specific embodiment of the present invention, the mean $T_{max}$ range may be from about 30 to about 70 minutes. In another embodiment, the mean $T_{max}$ range may be from about 40 to about 55 minutes. In another embodiment, the mean $T_{max}$ is about 25 minutes, about 30 minutes, about 35 minutes, about 40 minutes, about 50 minutes, about 55 minutes, about 60 minutes, about 65 minutes, or about 70 minutes, including all ranges and subranges therebetween. In a specific embodiment of the present invention, the coefficient of variation of the mean $T_{max}$ may be less than 40%. In another embodiment, the coefficient of variation of the mean $T_{max}$ may be less than 35%. In another embodiment, the coefficient of variation of the mean $T_{max}$ may be less than 30%. In another embodiment, the coefficient of variation of the mean $T_{max}$ may be less than 25%.

The observed low variability $T_{max}$ of the present invention provides significant and critical advantages. For example, a more variable $T_{max}$ may result in a dangerous phenomenon known as dose-stacking, which occurs when a repeat dose is administered before the peak effect of a previous dose. Such dose-stacking may lead to unintended and unwanted side effects. Thus, the dosage forms of the present invention provide a much more predictable $T_{max}$ that may significantly reduce the harmful consequences of dose stacking.

Figure 22:
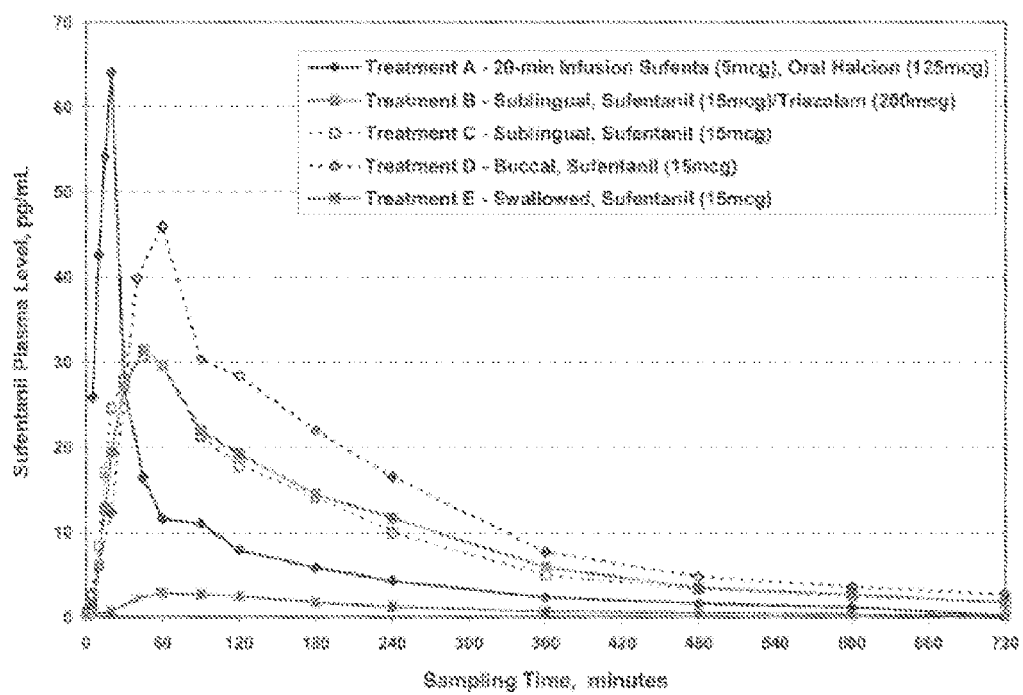
FIG. 22 is a graphic depiction of observed sufentanil plasma concentration (mean; pg/ml)) versus time, following administration to healthy human volunteers using various dosages forms and routes of administration. Specifically.

The low bioavailability of sufentanil from the GI route (about 7% as shown in FIG. 22) provides for majority of the drug delivered; as measured by plasma concentration, to be delivered via the oral transmucosal route. This amount is further increased when a majority of the total amount of sufentanil from the tablet is absorbed via the oral mucosal route. Accordingly, for example, when about 55% of the total amount of sufentanil from the tablet of the present invention is absorbed via the transmucosal route, at least about 95% of sufentanil delivered, as measured by plasma concentration, is delivered via the oral transmucosal route. In one embodiment, at least about 75% of sufentanil delivered; as measured by plasma concentration, is delivered via the oral transmucosal route, In another embodiment, at least about 80% of sufentanil delivered, as measured by plasma concentration, is delivered via the oral transmucosal route. In another embodiment, at least about 85% of sufentanil delivered, as measured by plasma concentration, is delivered via the oral transmucosal route. In another embodiment, at least about 90% of sufentanil delivered, as measured by plasma concentration, is delivered via the oral transmucosal route. In another embodiment, at least about 95% of sufentanil delivered, as measured by plasma concentration, is delivered via the oral transmucosal route. In another embodiment, at least about 96% of sufentanil delivered, as measured by plasma concentration, is delivered via the oral transmucosal route. In another embodiment, at least about 97% of sufentanil delivered, as measured by plasma concentration, is delivered via the oral transmucosal route. In another embodiment, at least about 98% of sufentanil delivered, as measured by plasma concentration, is delivered via the oral transmucosal route. In another embodiment, at least about 99% of sufentanil delivered, as measured by plasma concentration, is delivered via the oral transmucosal route.

Furthermore, since fentanyl has a 30% bioavailability from the GI route, swallowed drug can contribute to the $C_{max}$ plasma levels to a significant degree and results in the erratic $C_{max}$ and $T_{max}$ observed with these products. In contrast, the bioavailability of sufentanil from the GI route is about 7% (FIG. 22), and therefore swallowed drug will also not contribute to the $C_{max}$ plasma levels to a significant degree. As demonstrated below, the human studies provide a narrow mean $C_{max}$ range per mcg dosed of sufentanil. Table 2 demonstrates that the mean $C_{max}$, of a 2.5 mcg sufentanil formulation is 2.72 μg/mL per mcg dosed; the mean $C_{max}$ of a 5 mcg sufentanil formulation is 2.18 pg/mL per mcg dosed; and the mean $C_{max}$ of a 10 mcg sufentanil formulation is 2.75 μg/mL per mcg dosed. In another fast eroding formulation, Table 4 demonstrates that the mean $C_{max}$ of a 10 mcg sufentanil formulation is 1.65 μg/mL per mcg dosed; and the mean $C_{max}$ of an 80 mcg sufentanil formulation is 1.59 μg/mL per mcg dosed. Accordingly, in one embodiment of the present invention, the mean $C_{max}$ range may be about 1.5 μg/mL, per mcg dosed to about 3 μg/mL per mcg dosed. In another embodiment, the mean $C_{max}$ range may be about 2.0 μg/mL per mcg dosed to about 2.8 μg/mL per mcg dosed. In another embodiment, the mean $C_{max}$ range may be about 1.59 pg/ml per mcg dosed to about 2.75 pg/mL per mcg dosed.

Further, the lipid solubility (octanol-water partition coefficient) of sufentanil (1778:1) is greater than fentanyl (816:1) (van den Hoogen and Colpaert, Anesthes. 66:186-194, 1987). Sufentanil also displays increased protein binding (91-93%) compared with fentanyl (80-85%) (SUFENTA and Actiq® package inserts, respectively). Sufentanil has a pKa of 8.01, whereas the pKa of fentanyl is 8.43 (Paradis et al., Therapeutic Drug Monitoring, 24:768-74, 2002). These differences can affect various pharmacokinetic parameters, for example, sufentanil has been shown to have a faster onset of action and faster recovery time than fentanyl (Sanford et al., Anesthesia and Analgesia, 65:259-66, 1986). As compared to fentanyl, use of sufentanil can result in more rapid pain relief with the ability to titrate the effect and avoid overdosing.

Importantly, sufentanil has been shown to produce endocytosis of the mu-opioid receptor 80,000 times more potently than fentanyl (Koch et al., Molecular Pharmacology, 67:280-87, 2005). The result of this receptor internalization is that neurons continue to respond to sufentanil more robustly over time than with fentanyl, suggesting that clinically less tolerance would develop to sufentanil compared to fentanyl with repeated dosing.

Prior to the work of the current inventors, no pharmacokinetic data had been published on sublingual sufentanil in any form. Pharmacokinetic data for ocular and intranasal transmucosal delivery of sufentanil has been published based on studies in dogs and humans. Farnsworth et al. (Anesth Analg, 1998, 86:138-140) describe ocular transmucosal absorption and toxicity of sufentanil in dogs, where 50 mcg of sufentanil was administered over a period of 2.5 minutes to the conjunctiva of five anesthetized dogs. The $T_{max}$ occurred at 5 min with a $C_{max}$ of 0.81 ng/mL, and a $t_{1/2}$ of approximately 18 minutes. A study report of intranasal and intravenous administration of 15 mcg of sufentanil in 16 humans provides a comparison of pharmacokinetic profiles, where intranasal sufentanil was delivered via 3 drops in each nostril with 2.5 mcg/drop. Intranasal sufentanil had a 78% bioavailability based on the AUC from 0-120 minutes compared with intravenous delivery. Intranasal delivery resulted in a $T_{max}$ of 10 minutes with a $C_{max}$ of 0.08 ng/mL. The $t_{1/2}$ was approximately 80 minutes. See, Heimers et al., Can J. Anaesth. 6:494-497, 1989. A third study in pediatric patients describes preoperative intranasal dosing of 15 children with 2 mcg/kg sufentanil via nasal drops and with plasma levels of sufentanil measured starting at 15 minutes, which was too late to capture the $T_{max}$. Based on extrapolation of the data, the $C_{max}$ was approximately 0.3 ng/mL and the $t_{1/2}$ was approximately 75 minutes (Haynes et al., Can J. Anaesth. 40(3):286, 1993).

Sufentanil Dosage Forms

The active agent in the claimed dosage forms is sufentanil, alone or in combination with a sufentanil congener such as alfentanil, fentanyl, lofentanil, carfentanil, remifentanil, trefentanil, or mirfentanil. In a preferred embodiment, sufentanil alone is the active agent. Sufentanil may be provided in the claimed dosage forms in any of a number of formulations. Sufentanil may be provided as sufentanil citrate, sufentanil base, or a combination thereof. In various embodiments, the formulation of the present invention generally provides appropriate pain relief in all types of patients including children, and adults of all ages who are opioid tolerant or naïve. The invention finds utility in both the in-patient and out-patient setting.

The clinical use of sufentanil has predominantly been limited to IV administration in operating rooms or intensive care units. As further described herein, there have been a few studies on the use of liquid sufentanil preparations for low-dose intranasal administration and a case report of sublingual delivery of a liquid sufentanil preparation. In most of these studies, the smallest dosing of sufentanil in adults was 5 μg in opioid naïve patients. Intranasal bioavailability was approximately 75% of that obtained by IV, however no pharmacokinetic data has been published on the sublingual use of sufentanil.

The bioadhesive transmucosal formulations of the invention contain from about 0.25 to about 200 μg of sufentanil per dosage form for oral transmucosal delivery. As will be understood by those of skill in the art, the dose will be on the low end of the range for children and the high end of the range for adults dependent upon body mass, in particular when administered long-term to opioid-tolerant adults. Small-volume oral transmucosal drug delivery dosage forms of sufentanil have not been described.

Exemplary formulations of the invention for administration to children (pediatric patients) contain from about 0.25 to about 120 mcg of sufentanil per dosage form. For example, a formulation of the invention for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.1 mcg/kg.

Exemplary formulations of the invention for administration to adults contain from about 2.5 to about 200 μg of sufentanil per dosage form. For example, a formulation of the invention for administration to adults may contain about 2.5, 3, 5, 7.5, 10, 15, 20, 40, 60, 80, 100, 120, 140, 180 or 200 mcg or more of sufentanil for oral transmucosal delivery. Preferably, a sufentanil-containing dosage form comprises from about 5 to about 200 micrograms (mcg) of sufentanil, 5 mcg, 10 mcg, 15 mcg, 20 mcg, 30 mcg, 40 mcg, 50 mcg, 60 mcg, 70 mcg, 80 mcg, 100 mcg, 120 mcg, 140 mcg, 160 mcg, 180 mcg and 200 mcg of sufentanil. As will be understood by those of skill in the art, the dose will be on the low end of the range for children and the high end of the range for adults dependent upon body mass, in particular when administered long term to opioid-tolerant adults. Prior to the work of the current inventors, small-volume sufentanil-containing dosage forms for oral transmucosal drug delivery had not been described.

In various embodiments, the claimed dosage forms provide effective pain relief in all types of patients including children, adults of all ages who are opioid tolerant or naïve and non-human mammals. The invention finds utility in both the inpatient and outpatient setting and in the field.

Congeners of Sufentanil

Congeners of sufentanil find use in the compositions, methods and systems described herein, examples of which include alfentanil lofentanil, carfentanil, remifentanil, trefentanil or mirfentanil.

In certain embodiments, the dosage form comprises at least 0.005% to as much as 99.9% by weight of alfentanil, lofentanil, carfentanil, remifentanil, trefentanil or mirfentanil. The percentage of active ingredient(s) will vary dependent upon the size of the dosage form and nature of the active ingredient(s), optimized to obtain maximal delivery via the oral mucosal route. In some aspects of the invention, more than one active ingredient may be included in a single dosage form.

VI. Treatment of Pain

Using current treatment methods, pain control is attempted using a number of interventions, which generally include: patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer (i.e., breakthrough pain), etc. Post-operatively, for example, patients suffer from severe pain for the first few days followed by days of mild to moderate levels of pain.

The most common analgesic used to treat moderate to severe post-operative pain is TV morphine. This is either delivered on an "as needed" basis to the patient by a nurse using IV injection or commonly a morphine syringe is placed in a PCA pump and the patient self-administers the opioid by pressing a button which has a lock-out feature. Other opioids, such as hydromorphone and fentanyl may also be administered in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in un-sterile situations, where needles used for TV or IM administration can result in unintended needle sticks, risk of infection, etc. Oral opioid tablets often take 60 minutes to provide relief which is too long for someone in severe pain.

In a number of clinical settings, there is clearly a need for improved means to administer a drug that produces effective pain relief in a manner that is titratable, safe and convenient, and non-invasive that provides relief from acute, severe breakthrough or intermittent pain over an appropriate period of time.

The claimed compositions, methods and systems rely on administration of dosage forms comprising a pharmaceutically active substance such as sufentanil which is effective for the treatment of acute pain (i.e. post-operative pain), intermittent pain or breakthrough pain, using a dispensing device that includes features such as lock-out, a means for patient identification prior to drug administration and a means to protect the dosage forms stored in the dispensing device. The claimed methods and systems thereby provide significant advantages over currently available treatment modalities in terms of both safety and efficacy.

VII. In Vivo Human Studies

Provided herein is pharmacokinetic data obtained in humans based on studies where sufentanil was administered via the sublingual route using the claimed small volume dosage forms.

Two human clinical studies were performed using healthy human volunteers. The first study which is detailed in Example 1 was performed with 12 subjects (6 men and 6 women) using slow-eroding sublingual sufentanil dosage forms containing either 205 mcg, 5 mcg or 10 mcg of sufentanil base corresponding to 3.7 mcg, 7.5 mcg or 15 mcg of sufentanil citrate, respectively in comparison to a 10-minute IV infusion of 5 mcg sufentanil or 4 repeated doses of a slow-eroding sublingual sufentanil dosage form containing 5 mcg sufentanil administered at 10-minute intervals (Table 2). The second study which is detailed in Example 2 was performed with 11 subjects using faster-eroding sublingual sufentanil dosage forms containing either 10 mcg or 80 mcg of sufentanil base corresponding to 15 mcg or 120 mcg of sufentanil citrate, respectively, in comparison to a 10-minute IV infusion of 10 mcg sufentanil or a 20-minute IV infusion of 50 mcg sufentanil, a sublingual dose of 5 mcg of sufentanil solution or 4 repeated administrations of fast-eroding sublingual sufentanil dosage forms containing 10 mcg of sufentanil administered at 20-minute intervals (Table 3). All excipients were "pharmaceutically acceptable" (inactive) and have GRAS or "generally recognized as safe" status.

Sufentanil dosage forms designed for sublingual use were compared to IV sufentanil, administered through an IV catheter as a continuous infusion. Plasma samples were drawn from a different IV catheter at a remote location. The assay demonstrated good inter-day precision and accuracy at the high, medium and low quality control sample concentrations.

The dosage forms for the first study eroded over a period of 15-25 minutes in all subjects and are designated herein as "slow-eroding". The dosage forms for the second study eroded over a period of 6-12 minutes in all subjects and are designated herein as "faster-eroding". After placement of each sufentanil dosage form in the sublingual cavity of the healthy volunteers, a remarkably consistent pharmacokinetic profile was obtained. The bioavailability of sufentanil administered using small volume sublingual dosage forms as compared to IV administration for single and multiple administrations was high and ranged from 60.9°/0 (10 mcg dose; faster-eroding) to 97.2% (4×5 mcg dose (slow-eroding). The bioavailability of sufentanil administered using small volume sublingual dosage forms is greater than that of the fentanyl products, Actiq® and Fentora® (47% and 65%, respectively—Fentora® package insert). Importantly, the bioavailability is linked to the consistency of total drug delivered to the patient. For example, the total plasma drug area under the curve (AUC 0-infinity) for sufentanil dosage forms 10 mcg was 0.0705±0.0194 hr*ng/ml (mean±standard deviation (SD)). This SD is only 27.5% of the total AUC. Coefficient of variation (CV) is a term to describe the percent SD of the mean. The coefficient of variation for the fentanyl products, Fentora® (AUC is 45%) and Actiq® (AUC is 41%; Fentora® package insert), while the coefficient of variation around the bioavailability of sufentanil administered using small volume sublingual dosage forms is less than 40%. Therefore, the total dose delivered to the subject is not only more bioavailable for the sufentanil dosage forms but it is more consistent.

Although this high bioavailability could be due to a number of factors including but not limited to erosion time, it is likely that the lack of saliva produced by the small size of the dosage forms limits the swallowing of the drug and avoids the low bioavailability typical of drug absorption via the GI route. Both Fentora® and Actiq®) package inserts claim at least 50% and 75% of the drug dose, respectively, is swallowed via the saliva, and both exhibit lower bioavailability than the claimed dosage forms.

The dosage forms used in the clinical trials had a volume of approximately 5 microliters (mass of 5.5-5.85 mg), a small fraction of the size of Actiq® or Fentora® lozenges. Therefore, less than 25% of the drug is swallowed, which is a much lower percentage than is swallowed with Fentora® or Actiq®.

The sufentanil sublingual dosage forms are also superior in terms of consistent plasma levels early after administration. The $C_{max}$ obtained with the 10 mcg sufentanil dosage form was 27.5±7.7 pg/ml. The coefficient of variation of the $C_{max}$ is therefore only 28%. The $C_{max}$ for Fentora® and Actiq® suffer from variability of GI uptake of drug. Fentora® reports a $C_{max}$ of 1.02±0.42 ng/ml, therefore the coefficient of variation of the $C_{max}$ is 41%. The range of coefficients of variation for the various doses of Fentora® is from 41% to 56% (package insert). The Actiq® coefficient of variation of $C_{max}$ is reported as 33% (Fentora® package insert).

In addition to superior bioavailability and consistency in plasma concentrations, the $T_{max}$ for 10 mcg sufentanil dosage forms was 40.8±1-13.2 minutes (range 19.8-60 minutes). The reported average $T_{max}$ for Fentora® is 46.8 with a range of 20-240 minutes. The $T_{max}$ for Actiq® is 90.8 minutes, range 35-240 minutes (Fentora® package insert). Therefore, the consistency in onset of analgesia for sufentanil dosage forms is markedly better than that of Fentora® and Actiq®.

In addition, the $T_{max}$ values obtained following repeated sublingual administration of the claimed sufentanil dosage forms were significantly shorter than those observed following administration of a single sublingual sufentanil dosage form. Most notably, the $T_{max}$ obtained with repeat dosing of 10 µg (4×10 µg) sufentanil dosage forms (fast-eroding) occurred 24.6 minutes after the previous (fourth) dose. The coefficient of variation around $T_{max}$ was only 18%, indicating a very consistent and predictable $T_{max}$ with repeated sublingual administration of the claimed sufentanil dosage forms.

The linearity of sufentanil plasma levels following sublingual administration of the claimed sufentanil dosage forms doses was consistent from the 2.5 mcg dose up through 80 mcg dose.

Although still in development, published data allows comparison of the sufentanil pharmacokinetic data provided herein to that of Rapinyl®, a fentanyl sublingual fast-dissolve lozenge. The coefficient of variation around the AUC for all three doses of sufentanil exemplified herein (2, 5, and 10 mcg) averaged 28.6%, demonstrating that the observed low coefficient of variation is not dependent on dose. In contrast, the published bioavailability for a sublingual fentanyl product, Rapinyl®, is approximately 70% (Bredenberg, New Concepts in Administration of Drugs in Tablet Form, Acta Universitatis Upsaliensis, Uppsala, 2033). The coefficient of variation of the AUC (0-infinity) for Rapinyl® ranges from 25-42% and is dose-dependent.

In addition, the coefficient of variation of the $C_{max}$ for Rapinyl® varies from 34-58% depending on dose. As shown by the data presented herein, administration of the 10 mcg sufentanil dosage form resulted in a $C_{max}$ variation of only 28%, and the average coefficient of variation of $C_{max}$ for the 2, 5, and 10 mcg doses was 29.4%, indicating minimal variability depending on dose. Similarly, the coefficient of variation for $T_{max}$ with Rapinyl® ranges from 43-54% depending on dose, whereas for our sufentanil dosage forms, this coefficient of variation for $T_{max}$ averages only 29% over all three dosage strengths. This consistent onset of action achieved with sublingual sufentanil dosage forms allows a safer redosing window when compared to any of the three comparator drugs, since rising plasma levels are contained to a shorter period.

Additionally, as with Fentora® and Actiq®, Rapinyl® demonstrates a longer plasma elimination half-life (5.4-6.3 hours, depending on dose) than the claimed sufentanil dosage forms. The plasma elimination half-life of sufentanil in small sublingual dosage forms ranged from 1.5-2 hours following a single oral transmucosal administration in humans (Table 3), which allows for more titratability and avoids overdosing. As will be understood by those of skill in the art, the half-life described herein for the exemplified dosage forms may be adjusted by modification of the component and relative amounts of the excipients in the formulation used to make a given dosage form. The ability to titrate to higher plasma levels by administering repetitive doses of the sublingual sufentanil dosage forms was also tested in this human study.

The methods and systems described herein are designed to work effectively in the unique environment of the oral cavity, providing for higher levels of drug absorption and pain relief than currently available systems. The claimed methods and systems are designed to avoid the high peak plasma levels of intravenous administration by entry into the circulation via the sublingual mucosa.

The claimed methods and systems further provide for independent control of bioadhesion, dosage form disintegration (erosion) and drug release over time, together with administration using a device to provide a safe delivery profile. The device-administered sublingual dosage forms provide individual, repetitive doses that include a defined amount of the active agent (e.g., sufentanil), thereby allowing the patient or care giver to accurately titrate the amount of drug delivered and to adjust the amount as appropriate in a safe and effective manner. Further, treatment with the claimed compositions, methods and systems provides for improved safety by minimizing the potentially deleterious side effects of the peaks and troughs in the plasma drug pharmacokinetics, which are typical of currently available medications or systems for treatment of pain.

Advantages of the claimed sublingual dosage forms over various liquid forms for either sublingual or intranasal administration include local release of drug from the dosage form over time with minimal swallowing of liquid drug via either the nasal or oral/GI route.

Due to the small size of the oral transmucosal dosage forms, repeated placement in the sublingual cavity over time is possible. Minimal saliva production and minimal physical discomfort occurs due to the small size, which allows for repetitive dosing over days to weeks to months. Given the lipid profile of the sublingual cavity, the sublingual route, also allows for slower release into the plasma for certain drugs, such as sufentanil, which may be due to utilization of a "depot" effect that further stabilizes plasma levels compared to buccal delivery.

The oral transmucosal dosage forms are designed to fit comfortably under the tongue such that the drug form erodes sufficiently slowly to avoid the immediate peak plasma levels followed by significant drop off seen in prior art formulations such as described in U.S. Pat. No. 6,759,059 (Rapinyl®), wherein fentanyl was administered via tablets containing 400 mcg of fentanyl which resulted in a peak plasma level of 2.5 ng/ml followed by an immediate drop in plasma level. Fentora® (fentanyl buccal tablet) also suffers from a lack of a plateau phase but rather has a steep incline up to the $C_{max}$ followed by a significant drop-off in plasma levels (Fentor® a package insert).

VIII. Utility of Small-Volume Oral Transmocosal Dosage Forms.

The claimed dosage forms, methods and systems find utility in delivery of sufentanil via the oral mucosal route (such as sublingual) for treatment of pain. For example, the small volume of sublingual dosage forms provide for high bioavailability, low variability in $T_{max}$, low variability in $C_{max}$ and low variability in AUC. The dosage forms also provide for prolonged plasma levels within the therapeutic window.

More specifically, the claimed dosage forms, methods and systems provide the following advantages:

(a) there is a linear relationship between sufentanil plasma levels in a subject following administration of the claimed sufentanil dosage forms and the amount of sufentanil in the dosage form;

(b) a single sublingual administration of the claimed sufentanil dosage forms to a subject results in an $AUC_{inf}$ with a coefficient of variation of less than 40%;

(c) a single or repeated sublingual administration of the claimed sufentanil dosage forms to a subject results in a $T_{max}$ with a coefficient of variation of less than 40%;

(d) repeated sublingual administration of the claimed sufentanil dosage forms to a subject results in a bioavailability that is greater than the bioavailability following a single sublingual administration to said subject;

(e) the difference between the $T_{max}$ following repeated sublingual administration of the claimed sufentanil dosage forms and the time of the previous sublingual administration is shorter than the $T_{max}$ following a single sublingual administration to the subject;

(f) there is a linear relationship between $C_{max}$ and the amount of sufentanil in the dosage form; and (g) there is a linear relationship between $AUC_{inf}$ and the amount of sufentanil in the dosage form.

In one exemplary embodiment described in detail herein, the dosage forms find utility in treating a subject suffering from pain that may be associated with any of a variety of identifiable or unidentifiable etiologies. In this embodiment, the dosage forms find utility in suppression or mitigation of pain. The term "treatment" or "management" of pain is used here to generally describe regression, suppression, or mitigation of pain so as to make the subject more comfortable, as determined for example by pain score.

The invention finds utility in the treatment of both opioid naïve patients and opioid tolerant patients.

The dosage forms find particular utility in the treatment of acute pain, such as post-operative pain, as well as other pain, such as "in the field", i.e., under highly sub-optimal conditions.

The dosage forms find further utility in veterinary applications. Specific examples include, but are not limited to, any treatment of an acute condition for which IV administration is not readily available or inconvenient, such as pain relief, anxiety/stress relief, pre-procedural sedation, etc.

IX. Use of Formulations of the Invention—Pharmacokinetics (PK) and Formulation Attributes Oral transmucosal drug delivery is simple, non-invasive, and can be administered by the caregiver or the patient with minimal discomfort. Generally, oral transmucosal delivery of pharmaceuticals is achieved using solid dosage forms such as lozenges or tablets; however, liquids, sprays, gels, gums, powders, and films may also be used.

For certain drugs, such as those with poor bioavailability via the GI tract, such as many lipophilic opioids, oral transmucosal (OT) delivery may provide a better delivery route than GI delivery. For drugs such as opioids, oral transmucosal delivery has shorter onset time (i.e., the time from administration to therapeutic effect) than does oral GI delivery and provides significantly improved bioavailability.

The uptake of medications from the bioadhesive transmucosal formulations of the present invention results in a more consistent delivery between individual dosages and individual patients as compared to that of currently available oral transmucosal dosage forms for which a large fraction of drug uptake occurs via the GI route.

Figure 19:
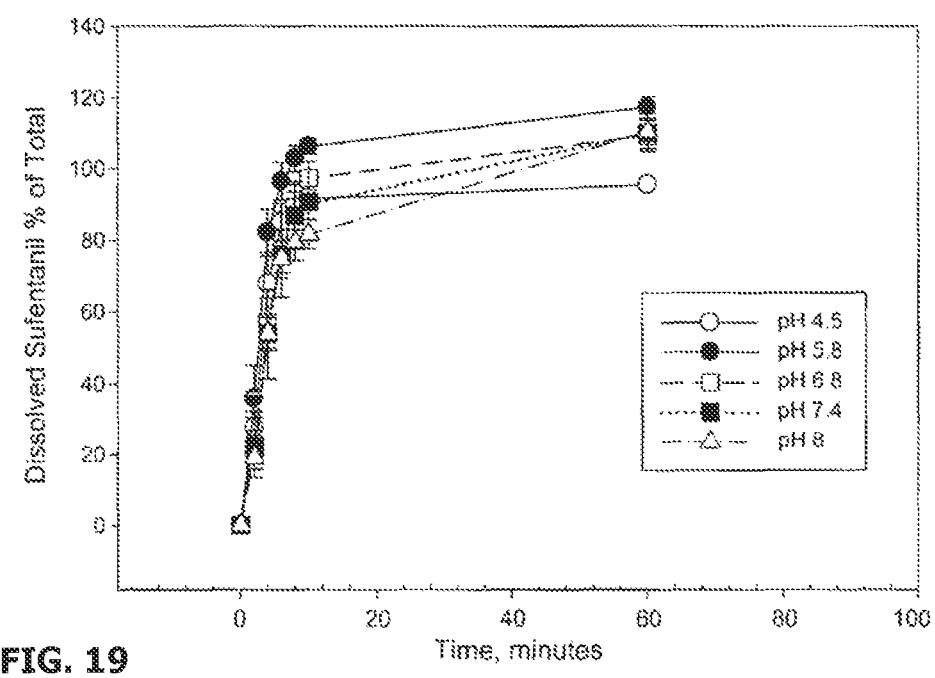
FIG. 19 is a graphic depiction of the effect of pH on dissolution kinetics of sufentanil from exemplary oral transmucosal formulations of the present invention (Formulation #A34).
Figure 20:
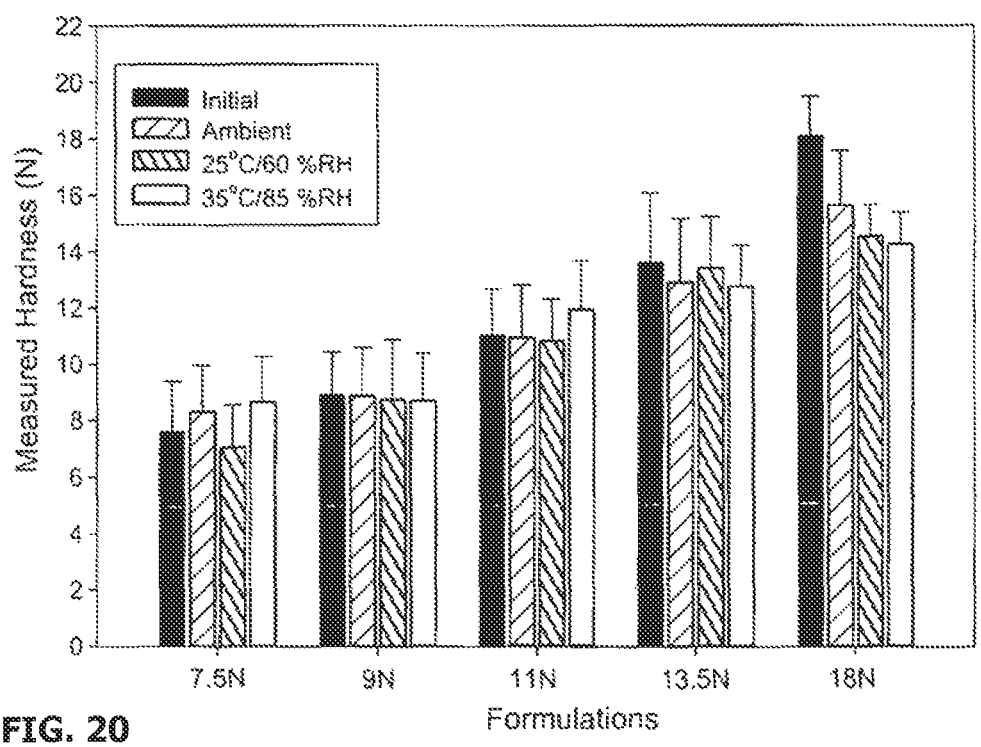
FIG. 20 is a graphic depiction of measured hardness (Newtons; "N") for formulations designated "7.5 N", "9 N", "11 N", "13.5 N" and "18 N" at an initial time point, at ambient temperature, at 25° C. and 60% relative humidity (RH) or 35° C. and 85% relative humidity.
Figure 21:
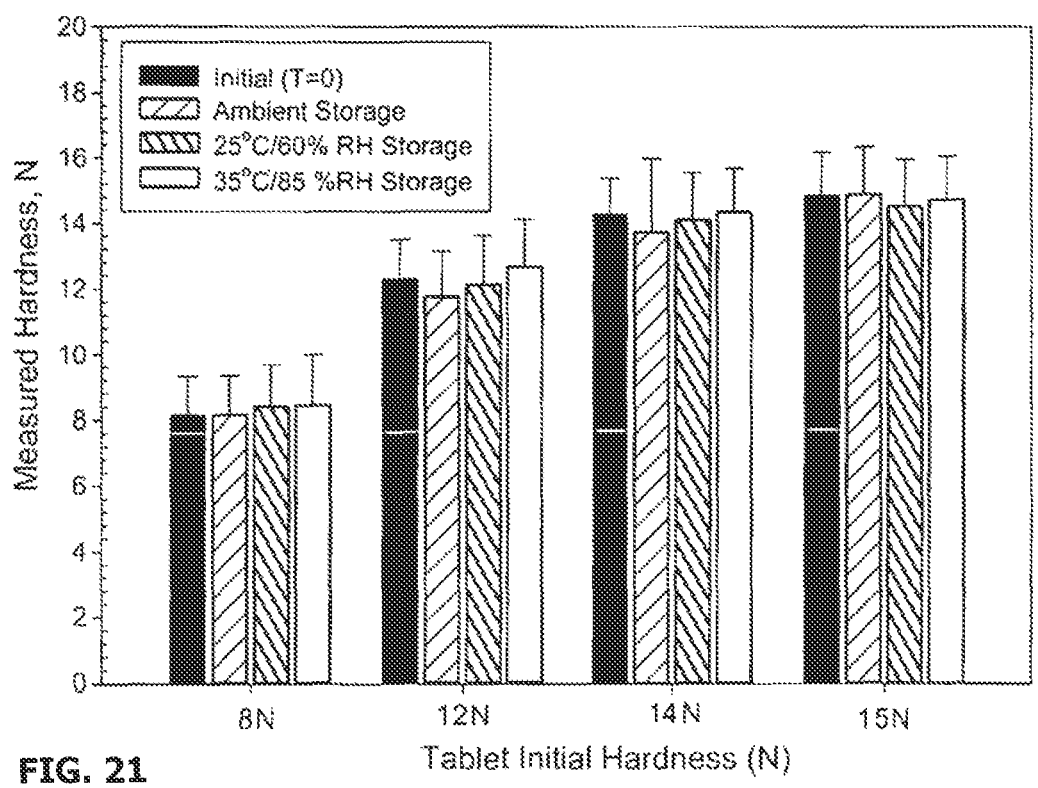
FIG. 21 is a graphic depiction of the effect of measured hardness (Newtons; "N") for formulations designated "8 N", "12 N", "14 N" and "15 N" at an initial time point, at ambient temperature, at 25° C. and 60% relative humidity (RH) or 35° C. and 85% relative humidity.

The bioadhesive transmucosal formulations of the present invention are designed work effectively in the unique environment of the oral cavity such that a limited amount of fluid, a relatively short period of time for drug dissolution, and pH levels within the oral cavity do not adversely affect absorption of the drug (FIG. 19). The dosage forms are also designed to improve dissolution, solubility, and stability of the drug. The advantages of the present invention include the ability to provide higher levels of drug absorption via oral transmucosal delivery, and consistent dose-to-effect times, making the present formulation a significant improvement for the treatment of acute or break-through pain.

The oral transmucosal formulations of the present invention are designed to avoid the high peak plasma levels of intravenous dosage forms by utilizing the oral mucosa and by controlling both tablet disintegration (or erosion) and drug dissolution and release from the tablet over time to provide a safer delivery profile. The oral transmucosal formulations of the present invention provide individual, repetitive doses that include a defined amount of the active agent, thereby allowing the patient to accurately titrate the amount of drug delivered and to adjust the amount as appropriate in a safe and effective manner.

An advantage of the bioadhesive oral transmucosal formulations described in this invention is that they exhibit consistent bioavailability and can maintain the plasma drug concentration within a targeted therapeutic window with significantly lower variability for a longer duration than currently available solid dosage forms. The high peak plasma levels typically observed for IV dosage forms are blunted following administration of a formulation of the invention, which are characterized by sustained release of the drug. In addition, a rapid decline in plasma levels is avoided since the drug is continually crossing from the oral cavity into the bloodstream during the length of time of dissolution of the tablet or longer, thus providing plasma pharmacokinetics with an extended plateau phase as compared to the IV route of administration. Further, the dosage forms of this invention may improve treatment safety by minimizing the potentially deleterious side effects due to the relative reduction of the peaks and troughs in the plasma drug pharmacokinetics, which compromise treatment safety and is typical of currently available dosage forms.

Advantages of solid sublingual formulations of the present invention over various liquid forms for either sublingual or intranasal administration of opioids include the sustained local release of the solid dosage form and the avoidance of swallowing of drug from administration of liquid dosage forms either via the nasal or the oral route. Published pharmacokinetic data on intranasal sufentanil liquid administration (15 µg) in humans demonstrates a bioavailability of 78% (Helmers et al. Comparison of intravenous and intranasal sufentanil absorption and sedation. Canadian Journal of Anaesthesia 36:494-497, 1989). Sublingual liquid sufentanil administration (5 µg) in Beagle dogs (Example 10) resulted in a bioavailability of 40%. Both these bioavailabilities are less than the 91% average that was obtained in human volunteers using sufentanil administered sublingually in the form of a NanoTab® formulation of the invention or greater than the 75% bioavailability obtained in the animal studies (Examples 9-14 below).

The oral transmucosal dosage forms of the invention are designed to fit comfortably under the tongue such that the drug-loaded dosage form disintegrates sufficiently slowly to avoid the immediate peak plasma levels followed by significant drop-off seen in prior art formulations such as described in U.S. Pat. No. 6,759,059 (Rapinyl®), wherein fentanyl was administered via tablets containing 400 µg of fentanyl which resulted in a peak plasma level of 2.5 ng/mL followed by an immediate drop in plasma levels. Fentora® (fentanyl buccal tablets) also suffers from a lack of a plateau phase but rather has a steep incline up to the $C_{max}$ followed by a significant drop-off in plasma levels (Fentora® package insert).

The bioadhesive transmucosal formulations described in this invention are designed to form two specific kinds of delivery vehicles: hydrogels and eroding tablets. These follow two distinct disintegration and drug release mechanisms based on (i) diffusion from a hydrogel and (ii) erosion with diffusion from the eroding-type tablets. Using these fundamental designs formulations of the invention can be designed to be fast-, intermediate- or slow-disintegrating. These system architectures are vastly different from effervescent-type tablets which are designed to break down rapidly by use of carbonate-type (or other) excipients. In addition, they are fundamentally different from dosage forms that are designed to disintegrate into large carrier particles that 'carry' the smaller (typically micron-sized) drug particles following 'ordered' mixing. The architecture of the transmucosal formulations of the present invention does not pose any requirements for specific particle sizes of drug or excipient particles, nor does require disintegration to the 'drug-coated' carrier particles to achieve the desired performance.

The bioadhesive transmucosal formulations of the present invention can be designed to manipulate and control the pharmacokinetic profile of the active drug. As such, the formulations can be adjusted to achieve fast disintegration and fast drug release and thus enable fast pharmacokinetic profiles that provide fast onset of action, while maintaining the other performance attributes of the tablet such as bioadhesion, reproducibility of action, blunted $C_{max}$, etc. Such fast-disintegrating tablets may be engineered to disintegrate from within 30 seconds up to 20 minutes and enable pharmacokinetic profiles that can vary accordingly with duration of action that can vary from 10 minutes to 1-2 hours. Alternatively, the formulations of the present invention can be adjusted to achieve 'intermediate' erosion times and drug release and thus enable 'intermediate' pharmacokinetic profiles that provide a more sustained action. Although such formulations may still provide a fast onset of action, they are mostly designed to enable the longer sustained effect while maintaining the other performance attributes of the tablet such as bioadhesion, reproducibility of action, blunted $C_{max}$, etc. Such 'intermediate'-disintegrating tablets may be engineered to disintegrate from within 30 seconds up to 30 minutes and enable pharmacokinetic profiles that can vary accordingly. Finally, the formulations of the present invention can be adjusted to achieve 'slow' disintegration times (and erosion kinetic profiles) and slow drug release and thus enable very prolonged PK that provides sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$ etc. Such slowly-disintegrating tablets may be engineered to disintegrate from within 15 minutes to up to 1 hours and enable pharmacokinetic profiles that can vary accordingly.

Further, the bioadhesive transmucosal dosage formulations of this invention can exhibit the aforementioned performance with a number of active drugs that may span a wide range of physicochemical properties, such as water solubility, partition coefficient, etc, as further described herein.

In addition, an important advantage exhibited by the oral transmucosal formulations of the present invention is the pH-independent nature of drug dissolution for drugs over the range of pH 4.5 and 8.0. pH-independence of drug dissolution minimizes the effect of environmental conditions on drug dissolution and absorption and provides consistently high bioavailability as described above. Further, normal physiologic or disease state saliva pH is typically between 4.5-8.0. Thus, the pH-independence of drug dissolution over a pH range of 4.5-8.0 exhibited by formulations of the invention provides advantages over prior art formulations.

Finally, the performance and attributes of the bioadhesive transmucosal formulations of this invention are independent of the manufacturing process. A number of conventional, well-established and known in the art processes can be used to manufacture the formulations of the present invention (such as wet and dry granulation, direct compression, etc), without impacting the dosage form physicochemical properties or in vivo performance.

Pharmacokinetics—Animal Studies

Selected dosage forms comprising formulations of the invention were tested in a suitable animal model to evaluate the pharmacokinetics following sublingual administration and thus elucidate the properties of the formulations of the present invention. Comparisons of oral transmucosal drug delivery using formulations of the invention relative to liquid sublingual administration as well as swallowed NanoTabs® were made to evaluate their performance. The results support our claim that the bioadhesive formulations of the invention are well tolerated sublingually in dogs, result in higher bioavailability and more consistent pharmacokinetic profiles than other oral transmucosal dosage forms, including instilled liquids. Further, they demonstrate the ability of the transmucosal formulations of this invention to blunt the $C_{max}$ and modify the drug absorption profile to achieve fast, intermediate or prolonged absorption.

In order to demonstrate the broad applicability of the bioadhesive transmucosal dosage forms of this invention, formulations were prepared with three different opioids: sufentanil citrate, fentanyl citrate and alfentanil hydrochloride. These molecules, albeit members of the same opioid family of analgesics, span a wide range of log values (between 0.006 and 3.382), as shown in Table 1A. The ability of the formulations of the current invention to similarly manipulate the in vivo pharmacokinetics of these distinct molecules in vivo demonstrates the broad applicability of the formulations of the present invention to a wide range of molecules with distinct physicochemical characteristics.

TABLE 1A

Physicochemical Properties of Selected Opioids.

| Property | Molecule | | |
| --- | --- | --- | --- |
| | Sufentanil | Fentanyl | Alfentanil |
| Molecular Weight (Da) | 387.5 | 336.5 | 416.2 |
| Solubility in water | 97 µg/mL | 200 µg/mL | 130 mg/mL |
| logP $_{(O/W)}$ | 3.382 | 2.928 | 0.006 |
| $T_m$ (° C.) | 97 | 87 | 140.8 |
| pKa | 8.01 | 8.43 | 6.5 |
| Therapeutic Index | 25,000 | 300 | 1000 |

One study was carried out to compare a sublingual 5 µg sufentanil NanoTab® formulation to IV sufentanil as described more fully in Example 9 (Table 16). A total of three Beagle dogs were studied and the results of the pharmacokinetic analysis are presented in FIG. 12 and tabulated in Table 17. All tablets disintegrated in <20 min following administration in dogs. The bioavailability sufentanil from the sublingual NanoTab® formulation was 74.8±110.7 compared to IV, thus confirming the superior attributes of the formulation over other dosage forms or formulation types (effervescent, etc). The coefficient of variation for the bioavailability was low (CV=14.4%) compared to that of other commercial transmucosal dosage forms, indicating unexpectedly very reproducible and efficient delivery. Absorption from the sublingual NanoTab® formulations is fast with an average $T_{max}$ of approximately 12 minutes, while the onset of delivery occurs within 7 minutes from administration. However, in contrast to IV administration, the formulation blunts the absorption maximum by 2-3-fold compared to IV. In addition, the absorption half-life is extended significantly (3.3-fold over IV) indicating a more sustained absorption profile.

An important mathematical ratio that demonstrates the prolonged plateau phase of the measured blood plasma levels of sufentanil following administration of the transmucosal bioadhesive formulations is the Therapeutic Time Ratio, which is defined as the time spent above 50% of $C_{max}$ normalized by the known IV terminal elimination half-life of the drug.

The Therapeutic Time Ratio of the sublingual sufentanil formulation of this example is 0.28 whereas the ratio for IV sufentanil is 0.05 (using the published IV elimination half-life of sufentanil in dogs of 139 minutes). Therefore, the transmucosal formulation (#44) resulted in a 5.6-fold increased therapeutic time ratio compared to IV sufentanil, indicating that after delivery from a sublingual bioadhesive formulation of this invention, sufentanil achieves and remains within efficacious therapeutic levels for longer time compared to IV. This example highlights some of the advantages of the sublingual sufentanil formulations of this invention, which include (i) efficient and reproducible delivery (ii) fast onset of action (iii) blunted $C_{max}$ of absorption and (iv) prolonged absorption profile. These attributes suggest that the transmucosal formulations of the present invention can lead to improved drug therapeutic benefit while minimizing side effects and improving the safety of drug administration.

Figure 13:
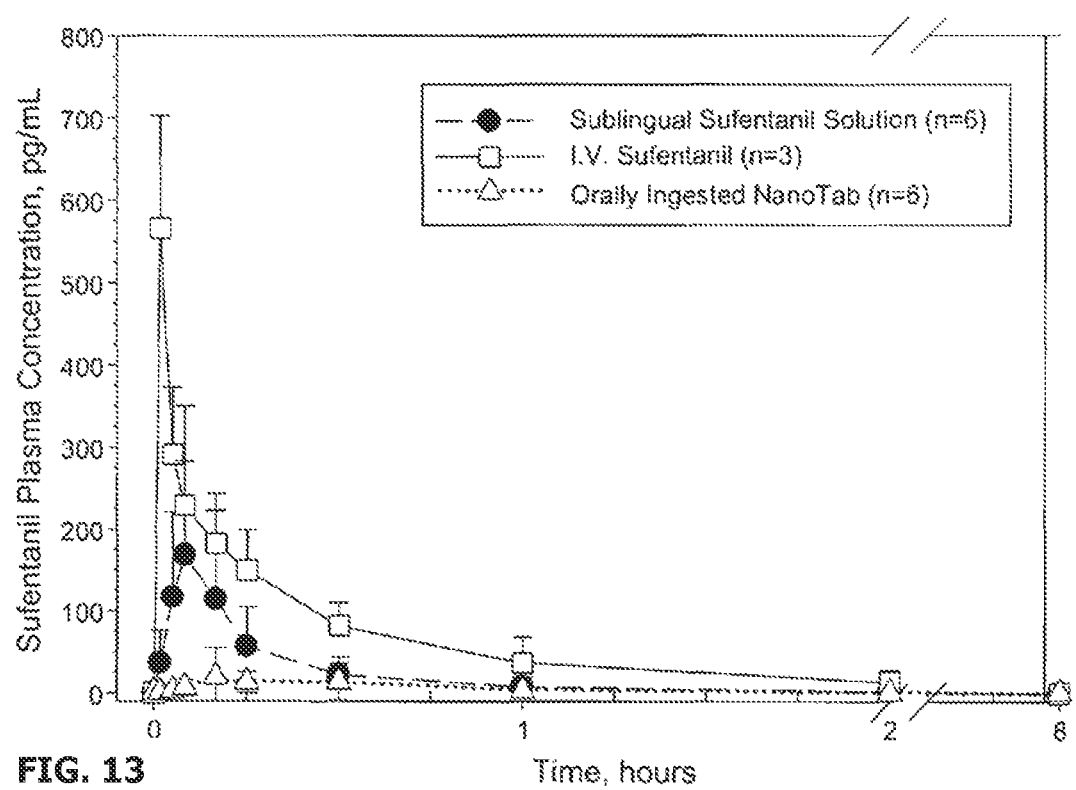
FIG. 13 is a graphic depiction of the pharmacokinetics of sufentanil following sublingual instillation (n=6) of a sufentanil solution and following oral ingestion of NanoTab® comprising formulation #44 (n=6) as compared to intravenous administration of sufentanil (n=3) in a healthy, conscious Beagle dog model. Error bars represent standard errors around the mean.

Another study in Beagle dogs was performed to evaluate the advantages of the sublingual formulations over liquid administration sublingually. This study is described in detail in Example 10 (Table 18). The results (presented in Table 19 and FIG. 13) indicate that although sublingual delivery of sufentanil (5 µg) via instillation from a liquid dosage form results in rapid $T_{max}$, this method of drug administration results in very low absorption (F=40.0±32.5%) and very high variability of absorption (83.1% CV) compared to the sublingual sufentanil formulation of Example 11. This is probably due to partial oral absorption of the drug following partial swallowing of the instilled liquid. The $C_{max}$ is also highly variable with this method of drug administration, exhibiting a high coefficient of variation of 72%. The Therapeutic Time Ratio for the instilled liquid sufentanil was calculated as 0.04±0.02, which is very similar to the IV sufentanil arm. Therefore, sublingual instillation from a liquid does not provide the advantageous therapeutic plateau observed with the sublingual formulation. These findings demonstrate that the high sublingual bioavailability observed from the bioadhesive formulations claimed in this application is not intrinsic to the molecule but rather it is a direct result of the unique design of the dosage form and its formulation. The transmucosal formulation's strong adhesion to the sublingual cavity minimizes the variability in the surface area available for absorption, as is the case of a liquid solution, thus improving delivery of the molecule to the systemic circulation. In addition, owing to its unique design and small dimensions, the NanoTab® does not elicit significant saliva production, thus reducing the potential for ingestion of the released drug. Both factors contribute to the higher and more uniform drug absorption from the sublingual cavity.

In another part of the same study (presented in Example 11), the bioavailability of sufentanil following swallowing of the NanoTab® was determined in the same animal model. Since there is little to no literature data on the GI sufentanil bioavailability, it was important to evaluate the bioavailability of this route of administration to further support the observation that drug from the sublingual administration of formulations could not be swallowed and maintain a high bioavailability. As indicated by the PK analysis data in Table 19, oral absorption of sufentanil from the bioadhesive tablets results in very low drug bioavailability (F=12.2±16.3%). The low absorption leads to substantial differences in PK, e.g., in the amount of drug absorbed and the pharmacokinetics of absorption ($C_{max}$, $T_{max}$) as shown in Table 19 (134.2% CV). The data further demonstrate that absorption from the bioadhesive formulation of Example #9 occurred almost exclusively via sublingual rather than GI absorption in contrast to commercially available opioid transmucosal dosage forms, in which a considerable amount of the drug is delivered to the GI tract (Actiq®—75%; Fentora®—50% oral absorption). These findings support the conclusion that the bioadhesive sublingual formulations of the current invention strongly adhere in the sublingual cavity in such a manner that they don't dislodge, thus avoiding oral ingestion and avoiding the high variability of plasma levels which is typical when drug is absorbed via the GI route.

In certain embodiments, the bioadhesive transmucosal formulations of the present invention can be modified in order to manipulate and control the pharmacokinetic profile. As an example the formulations can be adjusted to achieve fast disintegration and drug release and thus enable fast pharmacokinetic profiles that enable fast onset of action, while maintaining the other performance attributes of the tablet such as bioadhesion, reproducibility of action, blunted $C_{max}$, etc. Such fast-disintegrating tablets may be engineered to disintegrate from within 30 seconds up to 20 minutes and enable pharmacokinetic profiles that can vary accordingly with duration of action that can vary from 10 minutes to 1-2 hours. Alternatively, the formulations of the present invention can be adjusted to achieve 'intermediate' erosion times (and erosion kinetic profiles) and drug release and thus enable 'intermediate' pharmacokinetic profiles that provide a more sustained action. Although such formulations may still provide a fast onset of action, they are mostly designed to enable the longer sustained effect while maintaining the other performance attributes of the tablet such as bioadhesion, reproducibility of action, blunted $C_{max}$, etc. Such 'intermediate'-disintegrating tablets may be engineered to disintegrate from within 30 seconds up to 30 minutes and enable pharmacokinetic profiles that can vary accordingly. Finally, the formulations of the present invention can be adjusted to achieve 'slow' disintegration times (and erosion kinetic profiles) and slow drug release and thus enable very prolonged pharmacokinetic profiles that provide sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$, etc. Such slowly-disintegrating tablets may be engineered to disintegrate from within 15 minutes to up to 8 hours and enable pharmacokinetic profiles that can vary accordingly.

In addition, the pharmacokinetic profiles obtained from such bioadhesive sublingual formulations may vary depending on the dosage form design, geometry, compositions, etc. Examples of such PK profiles include ascending plasma profiles, which resemble bell-shaped curves, profiles that exhibit more than a single peak, prolonged seemingly flat PK profiles over the entire duration of action or intermediate profiles. Of particular interest are bi-phasic absorption profiles that exhibit a fast release component followed by a slow, extended release phase.

It should be noted that the bioadhesive transmucosal formulation described herein (whether the fast-, intermediate- or slow-disintegrating type) are neither effervescent nor do they disintegrate to the individual carrier particles comprising the dosage form To demonstrate the ability of the bioadhesive transmucosal formulations of the present invention to enable such distinct pharmacokinetic profiles, a number of formulations (#54-#58) were prepared in Example 12 representing both hydrogel- and eroding-type formulations. They were prepared with sufentanil citrate and designed to provide fast, intermediate and slow release of the drug from the dosage form. The formulations, which are described in Table 20, were prepared by direct compression, as described in Example 3, except for formulation #56, which was prepared by wet granulation, as described in Example 5 and were evaluated in a healthy conscious Beagle dog model, as described in Example 12 and Table 21.

In Vitro Formulation Characterization
In vitro Bioadhesion Force

As illustrated in Example 7, the transmucosal formulations of the present invention can be engineered to demonstrate varying degrees of bioadhesion. In the exemplary formulations of that example, the transmucosal formulations exhibited attachment forces to the porcine mucosa substrate that varied between 0.03 to 0.18 N/cm$^2$. The determined forces of attachment correlate directly to the magnitude of the force of adhesion in vivo. It is important to note that the specific experimental conditions (such as contact time, rinsing, etc) are expected to significantly influence the recorded detachment force; for example increased contact time will lead to increased interaction and thereby increased force of adhesion. For the determinations the 2 minutes of contact time were selected to reflect the contact time of a fast-disintegrating formulation.

The results summarized in Table 15 indicate that the strength of adhesion of the selected transmucosal formulations of Example 7 varied over a 6-fold range. However, the formulations of this invention are expected to exhibit strengths of adhesion that can extend well beyond this experimentally determined range. It is anticipated that the strength of bioadhesion of the formulations presented in this invention can be modified over the range of 0.005-1.0 N/cm$^2$ (500-10$^5$ dyn/cm$^2$).

In Vitro Drug Dissolution Kinetics

Sufentanil citrate dissolution from formulations #46-#48 (FIG. 11) follows diffusion-type kinetics according to Higuchi's law. This type of release is the signature of hydrogel-type systems, In addition, the data is described well by the Korsmeyer & Peppas equation (Korsmeyer, R. W., Gurney, R., Doecker, E., Burl, P., Peppas, N. A., Mechanisms of solute release from hydrophilic polymers, J. Pharm. Sci. 15: 25-35, 1983), with R$^2$ values between 0.96-0.98. Fitting of the dissolution curve indicated that drug release from all three systems was independent of the amount of drug loaded and that the exponent n returned fitted values of 0.566±0.109 (0.068% w/w sufentanil citrate tablet), 0.673±0.123 (0.163% w/w sufentanil citrate tablet) and 0.446±0.116 (0.273% w/w sufentanil citrate tablet). It is noted that all values of n approach 0.5, which indicates Fickian diffusion-controlled release which is somewhat influenced by the swelling of the tablet, further corroborating the hydrogel-type release from these formulations.

As also demonstrated in vivo (Examples 9-14), it is expected that the formulations of this invention can exhibit a range of dissolution profiles that may extend from a few minutes (2-4 min) to over several hours (6-8). In addition, depending on the drug physicochemical properties, the formulation composition and tablet design (such as physical dimensions, presence of coatings, number of coating layers, etc), the obtained in vitro drug dissolution profiles may exhibit a number of dissolution kinetics, such as first or second order, diffusion or erosion-based or following a mixed erosion-diffusion mechanism.

Dissolution testing of the colored dye (a surrogate for the active drug) from various formulations was performed in distilled water, using USP Apparatus 1 (Distek Technologies) and analyzed by UV-Vis detection at 590 nm for bromocresol blue. Each tablet was placed in 100 m basket which were then placed in 100-mL glass dissolution vessels containing 5 ml of dissolution media, thermostated at 37±0.5° C. Samples were pulled at selected intervals and analyzed using an Agilent 8453 UV-Vis spectrophotometer using a 1 cm-pathlength flow-through cell with Agilent 1FS sipper system. The in-vitro dissolution of the dye for the NanoTabs® was evaluated with selected formulations. The results are presented in FIG. 19.

Effect of pH on Sufentanil Formulation Dissolution In Vitro.

Sufentanil dissolution kinetics from formulation #A34 loaded with 80 µg of sufentanil base was determined in a Type II USP dissolution apparatus suitably modified to accommodate a small volume NanoTab® containing a small amount of sufentanil. Drug release from the bioadhesive transmucosal formulations were monitored by LC/MS. The results are shown in FIG. 19, and denote the similarity of the dissolution kinetics of sufentanil from the dosage form within the pH ranges examined.

Hardness

Dosage form hardness can be determined by any pharmaceutical-grade tablet hardness equipment, such as the Vankel VK-200 Hardness Tester (manufactured by Varian Inc., Cary, N.C.). The hardness of a given dosage form typically correlates with dosage form disintegration and may range from 0.1 to 50 kiloponds (±1% full scale). In general, for hardness testing, the dosage form is placed between the "jaws" of a hardness tester. The moving jaw moves toward the stationary jaw until the dosage form is crushed and the dosage form crushing force is measured by the apparatus. Exemplary hardness measurements for a dosage form of the invention, range from about 4 to about 25 Newtons, as illustrated by the hardness values for a number of formulations shown in Table 1B.

TABLE 1B

Hardness values for a number of bioadhesive drug formulations.

| Formulation # | Hardness (N) | Weight (mg) | Bioadhesion (Mean Detachment force) (N/cm2) |
|---|---|---|---|
| A13 | 10.7 | 5.7 | |
| A14 | 5.3 | 5.1 | |
| A15 | 8.9 | 5.6 | |
| A16 | 8.9 | 5.6 | 0.139 ± 0.061 |
| A17 | 12.2 | 6 | 0.066 ± 0.007 |
| A18 | 9.6 | 6.2 | 0.158 ± 0.009 |
| A19 | 11.6 | 6.1 | 0.126 ± 0.042 |

TABLE 1B-continued

Hardness values for a number of bioadhesive drug formulations.

| Formulation # | Hardness (N) | Weight (mg) | Bioadhesion (Mean Detachment force) (N/cm2) |
|---|---|---|---|
| A20 | 12.6 | 6.2 | |
| A21 | 14 | 6.1 | |
| A22 | 14 | 6.4 | 0.086 ± 0.041 |
| A23 | 11.6 | 5.8 | |
| A24 | 9.5 | 5.61 | |
| A25 | 10.2 | 5.62 | |
| A26 | 11 | 569 | |
| A27 | 7.5 | 5.5 | |
| A28 | 10.8 | 5.5 | |
| A29 | 8.5 | 5.63 | |
| A30 | 5 | 5.4 | |
| A31 | 8.1 | 5.9 | |
| A32 | 11.6 | 5.8 | |
| A33 | 10.7 | 5.8 | 0.097 ± 0.041 |
| A34 | 13.2 | 5.61 | 0.092 ± 0.039 |
| A35 | 10-13 | 5.85 | |
| A54 | 6.9 ± 0.7 | | |
| A55 | 9.8 ± 1.3 | | |
| A56 | 12.2 ± 3.2 | | |
| A57 | 6.9 ± 2.8 | | |
| A58 | 10.5 ± 1.8 | | |
| A59 | 7.7 ± 1.7 | | |
| A60 | 13.2 ± 1.0 | | |
| A61 | 11.3 ± 1.3 | | |
| A62 | 12.2 ± 0.9 | | |
| A63 | 15.3 ± 0.9 | | |
| A64 | 14.9 ± 1.1 | | |
| A65 | 10.6 ± 1.0 | | |
| A66 | 14.7 ± 1.2 | | |
| A67 | 12.4 ± 1.0 | | |
| A68 | 12.4 ± 1.0 | | |
| A69 | 13.3 ± 1.6 | | |

X. Dispensing Devices

One specific embodiment of the invention may include administering the dosage forms of the present invention to a patient thereof using a device. Single and multi-dose dispensing devices and systems for oral transmucosal administration of small volume drug dosage forms are provided. The dispensing devices are handheld and portable and comprise a housing having a dispensing end which typically has a proboscis with a shroud that provide a means for blocking or retarding saliva ingress and/or moisture control. The dispensing devices further provide safety features such as a means for lock-out and a means for patient identification.

The claimed dispensing devices, methods and systems comprise delivery of small volume dosage forms to the oral mucosa. The invention is not limited to administering the dosage forms, such as tablets, to specific devices, systems, and methodology detailed herein, as these may, of course, vary. It is also to be understood that the terminology used herein is for the purpose of describing particular embodiments only, and is not intended to limit the scope of the present invention.

EXAMPLES

The following examples are provided to illustrate the invention and are not intended to limit any aspect of the invention as set forth above or in the claims below.

Two different sublingual sufentanil formulations were evaluated including a slower-eroding form (erosion time of approximately 15-25 minutes; Examples 1A and 1B), and a faster-eroding form (approximate erosion time of 6-12 minutes; Examples 2A and 2B). Patients were blocked with a mu-opioid receptor antagonist, naltrexone (50 mg orally twice per day).

Sufentanil plasma concentrations with respect to time were analyzed and tabulated. The maximum sufentanil concentration in plasma ($C_{max}$), time to $C_{max}$ ($T_{max}$) and terminal $t_{1/2}$ were summarized for each dose group. After the final dosing of the repeat-dose studies, the sufentanil $t_{1/2}$ was determined. Comparisons were made between the area under the curve (AUC) for each single administration of sublingual sufentanil dose vs. IV. $C_{max}$ $T_{max}$ and $t_{1/2}$ data were compared for each sublingual sufentanil dosage vs. IV and sublingual administration of sufentanil liquid.

Example 1

Evaluation of the Bioavailability and Pharmacokinetics Following Sublingual Administration of a Small Volume Sufentanil Dosage Form

Example 1A

All subjects received a 10-minute IV infusion of 5 mcg sufentanil. After a 1-day washout period, each subject then received a single sublingual administration of a dosage form (comprising a slow-eroding formulation) containing 2.5 mcg of sufentanil. On the two subsequent study days, the dose was escalated, and each subject received a dosage form (comprising a slow-eroding formulation) containing 5 and 10 mcg of sufentanil.

Example 1B

All subjects received four repeated sublingual doses of a dosage form (comprising a slow-eroding formulation) containing 5 mcg of sufentanil administered at 10-minute intervals.

The slow-eroding sublingual sufentanil formulation containing 10 mcg sufentanil is provided below:

| Ingredient | Amount |
| --- | --- |
| Sufentanil Citrate | 0.27% |
| Mannitol (Pearlitol 200SD) | 73.77% |
| PEG 8000 | 14.98% |
| Polyox 303 | 3.00% |
| Lutrol F68 | 2.00% |
| Stearic Acid | 5.00% |
| Mg Stearate | 1.00% |
| Total | 100.00% |

The sufentanil plasma concentration at various time points following a single sublingual administration of a 2.5, 5, or 10 mcg sufentanil dosage form (slow-eroding) or 4 administrations of a 5 mcg sufentanil dosage form (slow-eroding) 10 minutes apart are shown in FIG. 1.

The mean sufentanil $t_{1/2}$ was similar for all of the sufentanil doses and varied from 1.56 hours (5 mcg sublingual dosage form) to 1.97 hours (10 mcg sublingual dosage form) with no obvious differences based on dose or route of administration (Table 1). The mean sufentanil $C_{max}$ and $AUC_{inf}$ increased with dose and were proportional to dose. The $T_{max}$ following a single sublingual administration of sufentanil ranged from 0.68 to 0.77 hours. The bioavailability following sublingual administration varied from 74.5% in subjects who were administered 5 mcg sufentanil dosage forms to 95.5% in subjects who were administered 10 mcg sufentanil dosage forms.

Table 2 provides a summary of pharmacokinetic parameters including $C_{max}$, $T_{max}$, $AUC_{inf}$, F and $t_{1/2}$. The $C_{max}$ after multiple sublingual dosing was 46.36 μg/mL. The mean $AUC_{inf}$ increased with multiple sublingual dosing of sufentanil and was generally proportional to dose when compared to single sublingual administration. The bioavailability of sufentanil following multiple sublingual dosing (97.2%) was greater than that following single administration at the same dose level (74.5%).

TABLE 2

Summary of Sufentanil Pharmacokinetic Parameters

| Parameter | | 5 mcg IV | 2.5 mcg | 5 mcg | 10 mcg | 4×5 mcg |
| --- | --- | --- | --- | --- | --- | --- |
| $C_{max}$ | (pg/mL) | 81.3 ± 28.1 | 6.8 ± 2.1 | 10.9 ± 3.5 | 27.5 ± 7.7 | 46.4 ± 12.4 |
| $T_{max}$ | (hr) | 0.16 ± 0.03 | 0.73 ± 0.13 | 0.77 ± 0.29 | 0.68 ± 0.22 | 1.16 ± 0.23** |
| $AUC_{inf}$ | (hr*pg/mL) | 38.4 ± 8.5 | 18.0 ± 4.5 | 27.4 ± 9.1 | 71.2 ± 20.7 | 146.5 ± 39.1 |
| $t_{1/2}$ | (hr) | 1.66 ± 0.72 | 1.71 ± 0.51 | 1.56 ± 0.57 | 1.97 ± 0.85 | 3.29 ± 1.10 |
| F | (%) | — | 95.3 ± 19.1* | 74.5 ± 26.3* | 95.5 ± 29.2* | 97.2 ± 21.2* |

*% F calculated using 5 mcg IV AUC
**4 doses administered 20 minutes apart

Figure 2:
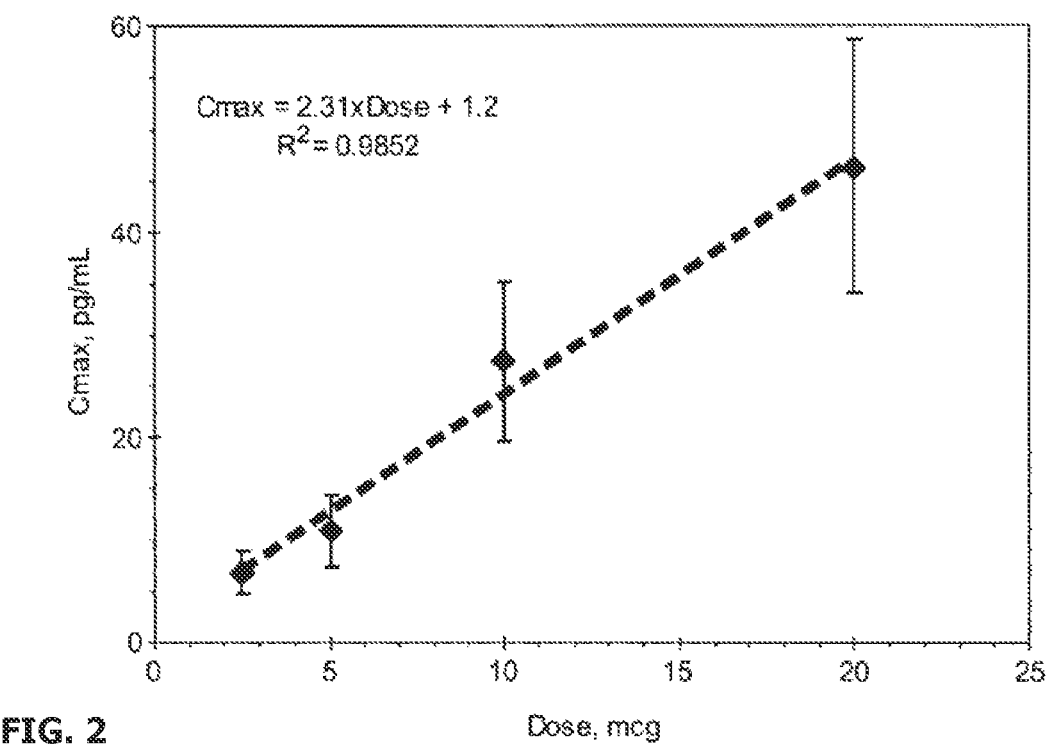
FIG. 2 is a graphic depiction of the linearity of $C_{max}$ (mean±SD) versus sufentanil dose (mcg), following sublingual administration of 2.5, 5, 10 or 4×5 mcg sufentanil dosage forms (slow-eroding) in healthy human volunteers.
Figure 3:
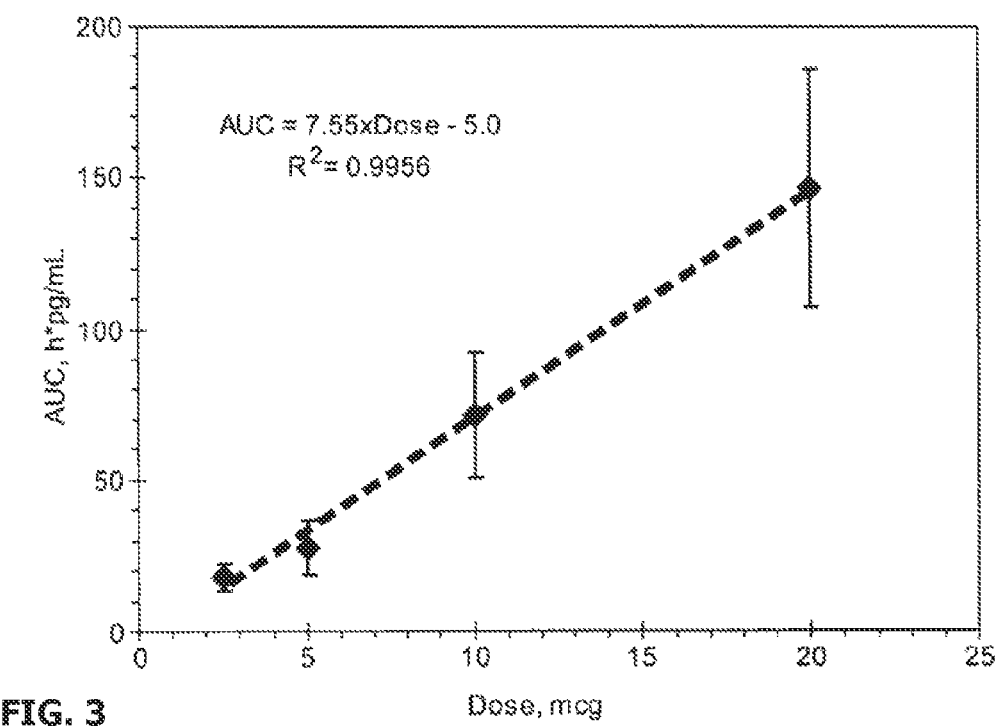
FIG. 3 is a graphic depiction of the linearity of $AUC_{inf}$ (mean±SD) versus sufentanil dose (meg), following sublingual administration of 2.5, 5, 10 or 4×5 mcg sufentanil dosage forms (slow-eroding) in healthy human volunteers.

A paired t-test comparison of the mean sufentanil $C_{max}$ and $AUC_{inf}$ parameters was conducted after normalizing to the 10 mcg sublingual dose. The results are shown in Tables 3A and 3B. Results show that the $C_{max}$ and $AUC_{inf}$ were dose proportional from 2.5 to 10 mcg. Supporting data for dose-proportionality of the $C_{max}$, and $AUC_{inf}$ is shown in FIGS. 2 and 3, respectively.

TABLE 3A

Comparison of Sufentanil Pharmacokinetic Parameters Dose-Normalized to 10 mcg (2.5 mcg slow-eroding dosage forms)

| n = 12 | 2.5 mcg | 10 mcg | Difference | Standard deviation | t value | p value |
| --- | --- | --- | --- | --- | --- | --- |
| $C_{max}$ (pg/mL) | 27.24 | 27.45 | −0.21 | 10.24 | −0.07 | 0.946 |
| $AUC_{inf}$ (hr*pg/mL) | 71.85 | 71.18 | −0.67 | 16.31 | 0.14 | 0.89 |

TABLE 3B

Comparison of Sufentanil Pharmacokinetic Parameters Dose-Normalized to 10 mcg 5 mcg slow-eroding dosage forms)

| n = 12 | 5 mcg | 10 mcg | Difference | Standard deviation | t value | p value |
| --- | --- | --- | --- | --- | --- | --- |
| $C_{max}$ (pg/mL) | 21.81 | 27.45 | −5.65 | 10.99 | −1.78 | 0.10 |
| $AUC_{inf}$ (hr*pg/mL) | 54.85 | 71.18 | −16.33 | 17.94 | −3.15 | 0.009** |

**p value <0.05, statistically significant

Figure 4:
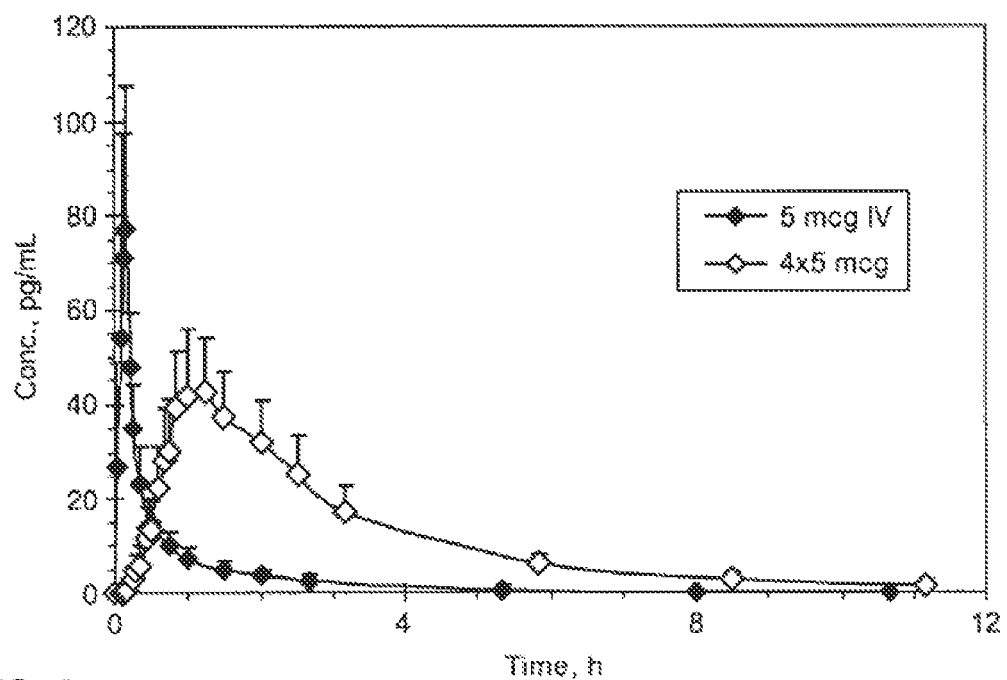
FIG. 4 is a graphic depiction of sufentanil plasma concentration (mean±SD) versus time, following repeated sublingual administration of four 5 mcg sufentanil dosage forms (slow-eroding) at 10 minute intervals in healthy human volunteers as compared to IV Infusion of 5 mcg sufentanil over 10 minutes.

Mean sufentanil plasma concentrations versus time (±SD) following repeated sublingual administration of 4×5 mcg sufentanil dosage forms (slow-eroding) at 10 minute intervals in healthy human volunteers as compared to IV Infusion of 5 mcg sufentanil over 10 minutes are shown in FIG. 4.

Figure 5A:
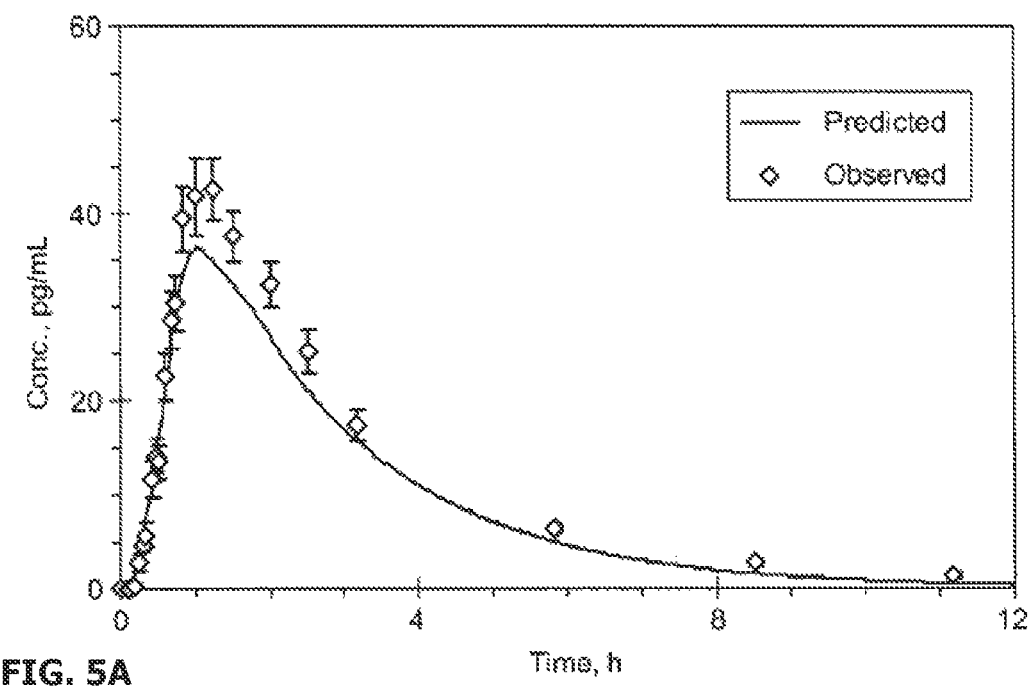
FIGS. 5A and 5B provide a graphic depiction of observed and predicted sufentanil plasma concentration (mean±SD) versus time, following repeated sublingual administration of 4×5 mcg sufentanil dosage forms (slow-eroding) at 10 minute intervals in healthy human volunteers over a period of 12 hours (FIG. 5A) or a period of 2.5 hours (FIG. 5B).
Figure 5B:
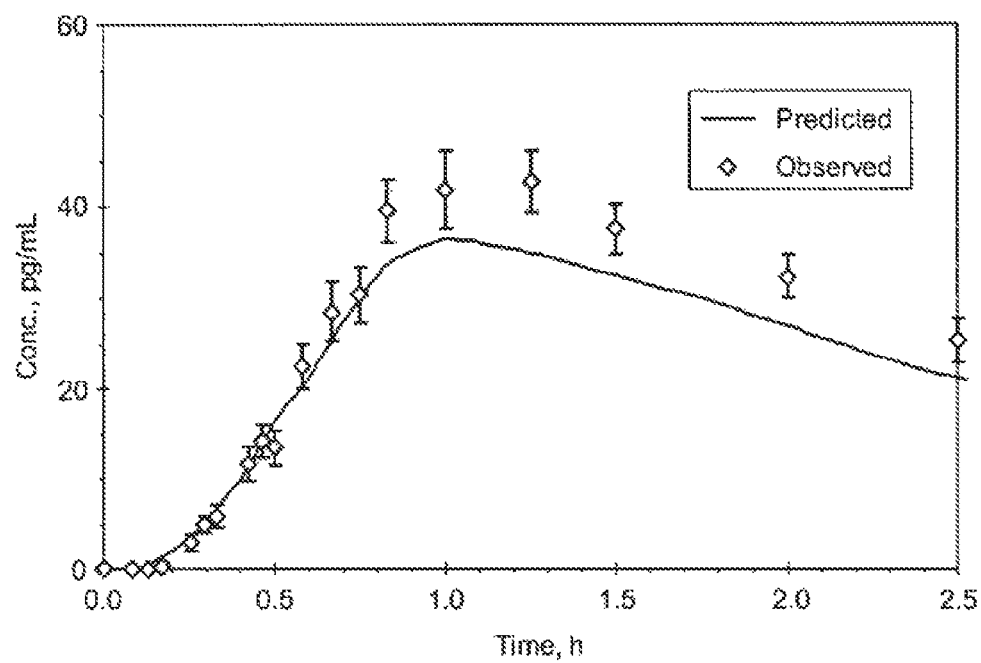

A simulation was used to estimate sufentanil plasma concentration following administration of 4×5 mcg sublingual sufentanil dosage forms (slow-eroding), administered 10 minutes apart. The simulation was conducted by superposition of the mean plasma concentration over time profile of a single administration of the 5 mcg sufentanil dosage form (slow-eroding). The simulation predicted and the observed mean (±SE) sufentanil plasma concentration versus time profiles were compared over a period of 12 hours (FIG. 5A) and a period of 2.5 hours (FIG. 5B). The predicted sufentanil concentrations based on the simulation closely tracks the observed sufentanil plasma concentration over time.

Example 2

Further Evaluation of the Bioavailability and Pharmacokinetics Sufentanil Following Sublingual Administration of a Small Volume Dosage Form Example 2A Subjects were administered 5 mcg of sufentanil solution via the sublingual route (N=2) or a 10-minute IV infusion of 5 mcg sufentanil (N=10), a single sublingual administration of a dosage form containing 10 mcg of sufentanil (faster-eroding formulation) and four repeated sublingual doses of a dosage form containing 10 mcg of sufentanil (faster-eroding formulation) administered at 20-minute intervals.

Example 2B

All subjects were administered a 20-minute IV infusion of 50 mcg sufentanil and a single sublingual administration of a dosage form containing 80 mcg of sufentanil (faster-eroding formulation).

The fast-eroding sublingual sufentanil formulation containing 10 mcg sufentanil is provided below:

| Component | Amount |
| --- | --- |
| Sufentanil Citrate | 0.26% |
| Mannitol SD100 | 70.64% |
| Di-Calcium Phosphate di-hydrate | 20.00% |
| HPMC K4M Premium CR | 3.00% |
| Stearic Acid | 5.00% |
| Mg Stearate | 1.00% |
| BHT | 0.10% |
| Total | 100.00% |

Figure 6:
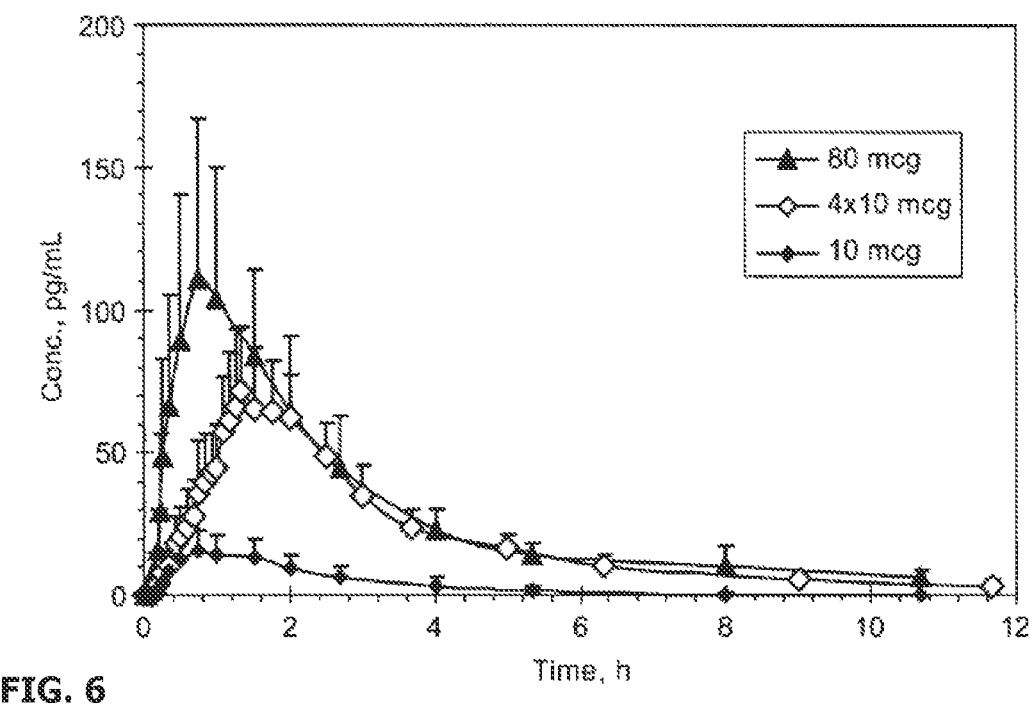
FIG. 6 is a graphic depiction of sufentanil plasma concentrations (mean±SD) versus time, following sublingual administration of 10, 40 (10 mcg every 20 minutes×4 doses) and 80 mcg sufentanil dosage forms (faster-eroding) in healthy human volunteers.

The sufentanil plasma concentration (mean±SD) at various time points following a single sublingual administration of 10 mcg and 80 mcg sufentanil dosage forms (faster-eroding) and 4 administrations of the 10 mcg sufentanil dosage form (faster-eroding) 20 minutes apart are shown in FIG. 6.

The mean $t_{1/2}$ was similar for the single sufentanil administrations and varied from 1.72 hours (5 mcg IV) to 1.67 hours (10 mcg sublingual). The mean sufentanil $AUC_{inf}$ increased with dose following single and multiple sublingual sufentanil administrations. The bioavailability was 60.9% in subjects treated with a single 10 mcg sublingual sufentanil dosage form (fast-eroding) and 87.8% following multiple (4×10 mcg) sublingual sufentanil administrations.

Figure 7A:
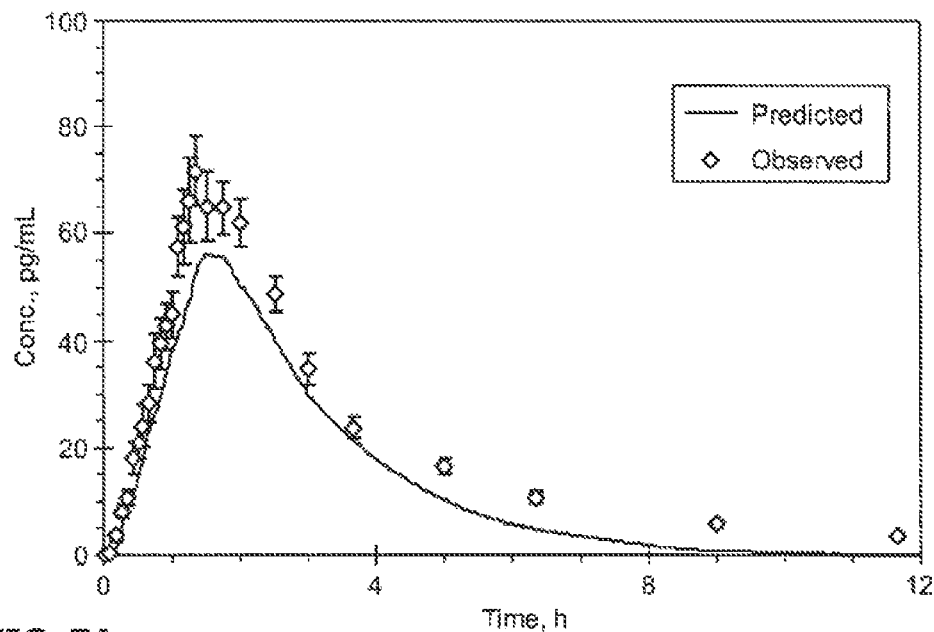
FIGS. 7A and 7B are a graphic depiction of observed and predicted sufentanil plasma concentration (mean±SD) versus time, following repeated sublingual administration of 4×10 meg sufentanil dosage forms (faster-eroding) at 20 minute intervals in healthy human volunteers over a period of 12 hours (FIG. 7A) or a period of 2.5 hours (FIG. 7B).
Figure 7B:
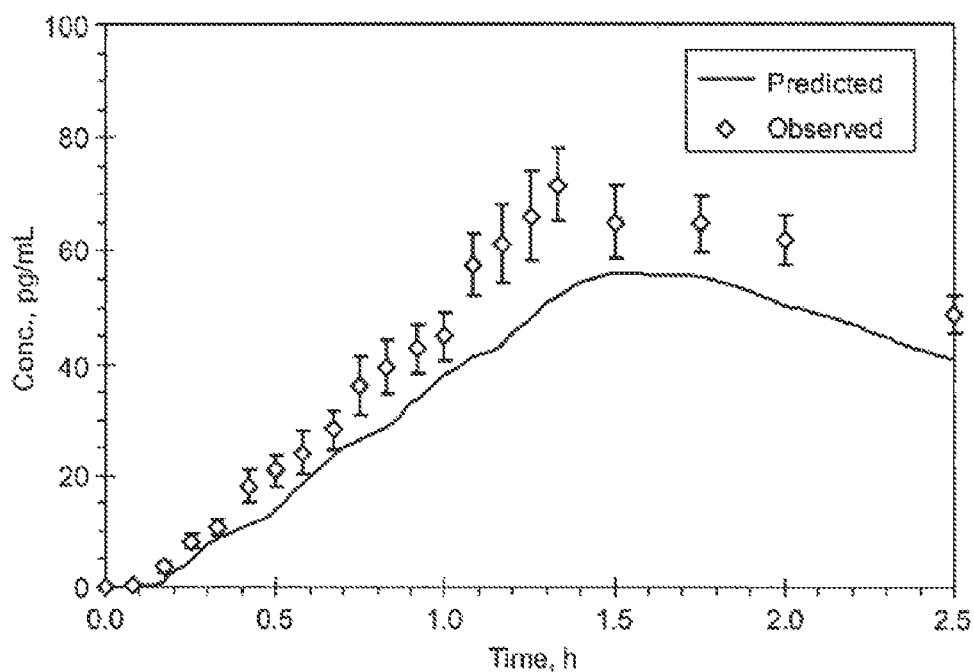

A simulation was used to estimate sufentanil plasma concentration following administration of 4×10 mcg sublingual sufentanil dosage forms (faster-eroding), administered 20 minutes apart. The simulation was conducted by superposition of the mean plasma concentration over time profile of a single administration of the 10 mcg sufentanil dosage form (faster-eroding). The simulation-predicted and the observed mean (±SE) sufentanil plasma concentration versus time profiles were compared over a period of 12 hours (FIG. 7A) and a period of 2.5 hours (FIG. 7B). The observed sufentanil plasma concentrations were greater than the predicted sufentanil plasma concentrations (based on the simulation) over time.

TABLE 4

Summary of Sufentanil Pharmacokinetic Parameters

| Parameter | | 5 mcg IV | 10 mcg | 4×10 mcg | 80 mcg | 50 mcg IV |
| --- | --- | --- | --- | --- | --- | --- |
| $C_{max}$ | (pg/mL) | 63.9 ± 28.2 | 16.5 ± 6.8 | 78.7 ± 20.1 | 127.2 ± 42.3 | 561.1 ± 277.7 |
| $T_{max}$ | (hr) | 0.17 ± 0.0 | 0.84 ± 0.35 | 1.41 ± 0.25** | 0.89 ± 0.35 | 0.34 ± 0.11 |
| $AUC_{inf}$ | (hr*pg/mL) | 39.4 ± 9.6 | 44.9 ± 24.6 | 253.4 ± 70.1 | 382.1 ± 88.2 | 528.0 ± 134.4 |
| $t_{1/2}$ | (hr) | 1.72 ± 0.47 | 1.67 ± 0.67 | 3.54 ± 1.02 | 4.23 ± 0.90 | 3.69 ± 0.78 |
| F | (%) | — | 60.9 ± 27.7* | 87.8 ± 22.2* | 70.1 ± 20.1* | — |

*% F calculated using 5 mcg IV AUC
**4 doses administered 20 minutes apart

The bioavailability following sublingual administration of the 80 mcg sufentanil dosage form (faster-eroding) was 70.1%.

Figure 8:
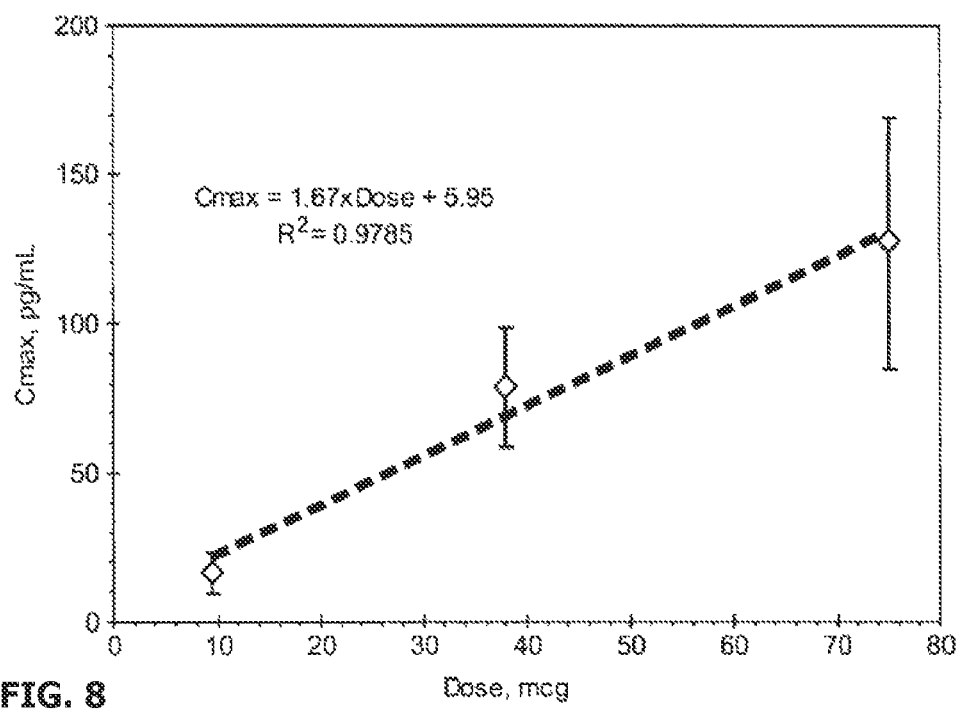
FIG. 8 is a graphic depiction of the linearity of $C_{max}$ (mean±SD) versus sufentanil dose (mcg), following sublingual administration of 10, 4×10 or 80 mcg sufentanil dosage forms (faster-eroding) in healthy human volunteers.
Figure 9:
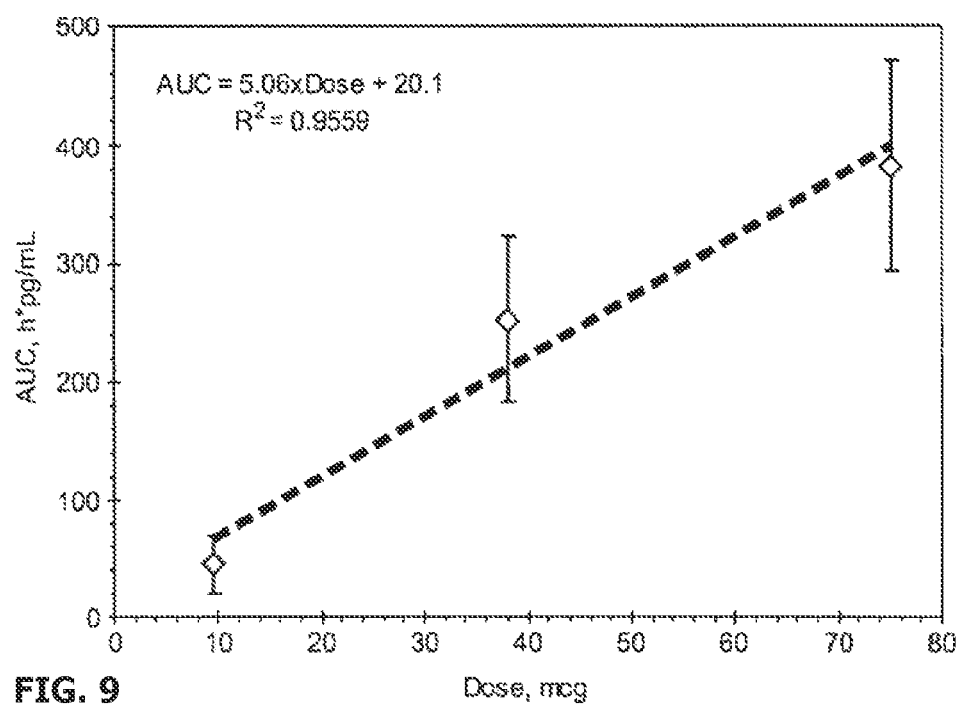
FIG. 9 is a graphic depiction of the linearity of $AUC_{inf}$ (mean±SD) versus sufentanil dose (meg), following sublingual administration of 10, 4×10 or 80 mcg sufentanil dosage forms (faster-eroding) in healthy human volunteers.

A paired t-test comparison of the mean sufentanil $C_{max}$ and $AUC_{inf}$ parameters was conducted after normalizing to the 10 mcg sublingual dose. The results presented in Table 4 show that the $C_{max}$ and $AUC_{inf}$ were dose proportional from 10 to 80 mcg. Supporting data for dose-proportionality of the $C_{max}$ and $AUC_{inf}$ is shown in FIGS. 8 and 9, respectively.

TABLE 5

Comparison of Sufentanil Pharmacokinetic Parameters Dose-Normalized to 10 mcg (80 mcg faster-eroding dosage forms)

| n = 11 | 10 mcg | 80 mcg | Difference | Standard deviation | t value | p value |
| --- | --- | --- | --- | --- | --- | --- |
| $C_{max}$ (pg/mL) | 16.59 | 16.93 | −0.34 | 8.04 | −0.14 | 0.89 |
| $AUC_{inf}$ (hr*pg/mL) | 45.02 | 50.88 | −5.86 | 23.85 | −0.81 | 0.43 |

Figure 10A:
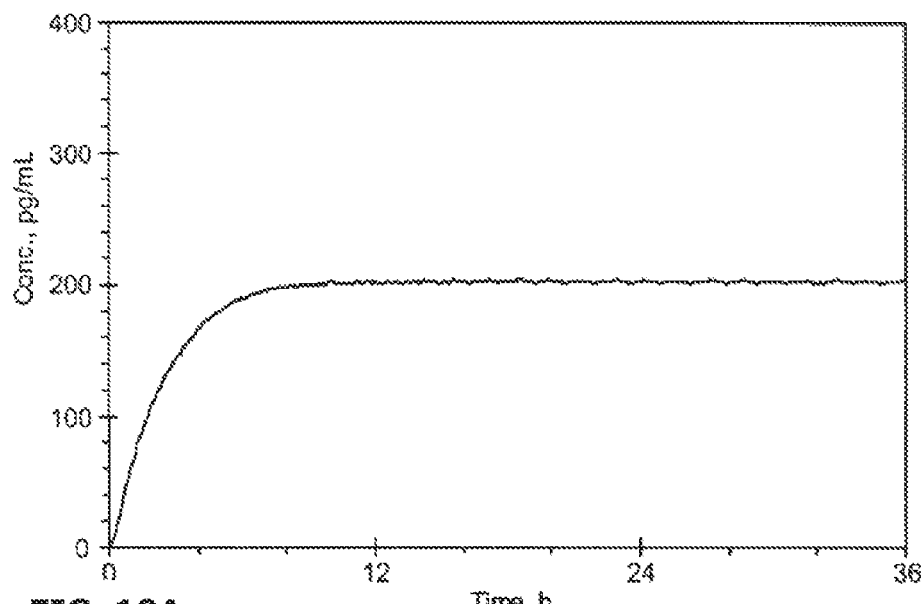
FIGS. 10A and 10B provide a graphic depiction of steady-state sufentanil plasma concentration versus time predicted by superposition following repeated sublingual administration of 10 mcg doses of sufentanil at 20 minute intervals (FIG. 10A) or 15 mcg doses of sufentanil at 20 minute intervals (FIG. 10B).
Figure 10B:
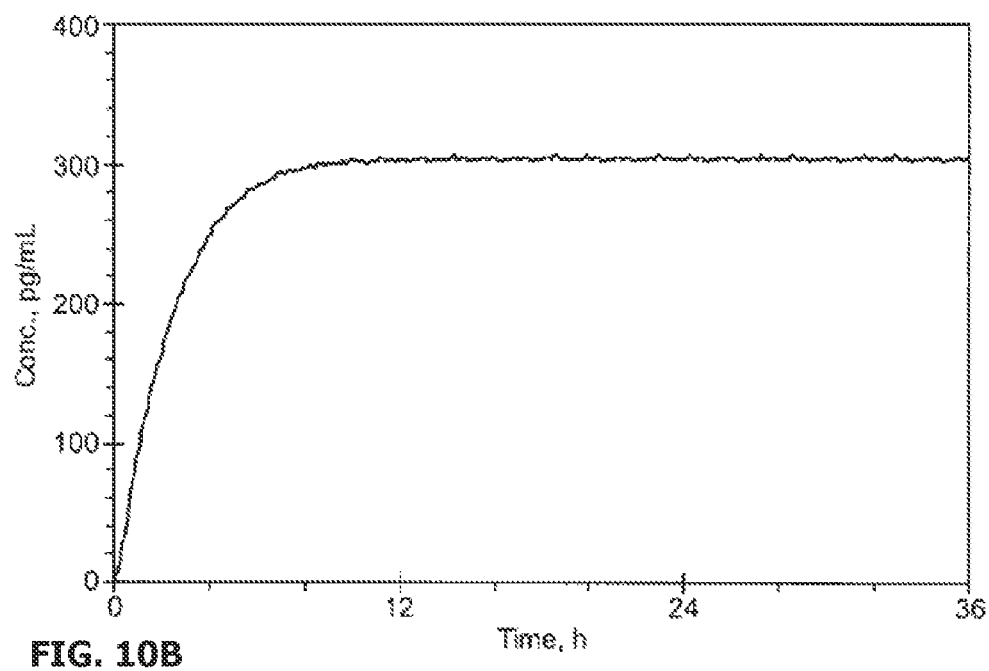

A simulation of sufentanil concentrations following multiple administrations of 10 or 15 mcg sublingual sufentanil dosage forms (slow-eroding), administered every 20 minutes was carried out. Dosage forms comprising the slow-eroding formulation resulted in a bioavailability of greater than 95%, and therefore serve as a basis for an estimate of the highest predicted steady-state sufentanil concentration following multiple administrations of 10 or 15 mcg sublingual sufentanil dosage forms. Steady-state sufentanil concentrations can be reached in about 12 hours after repeated sublingual doses at 20 minute intervals. The simulation predicted steady-state sufentanil concentrations of 200 pg/mL for administration of 10 mcg of sufentanil at 20 minute intervals and 300 pg mL for administration of 15 mcg of sufentanil at 20 minute intervals as shown in FIGS. 10A and B, respectively. The simulations suggest that a minimal re-dosing interval of 20 minutes is safe. The following examples are offered to illustrate, but not to limit the claimed invention. Unless noted, the total mass of all tablets made below is 5.5 mg. Further, all tablets prepared with active drug substances whether by direct compression or by wet granulation exhibited high content uniformity, as defined by the USP Pharmacopoeia with % RSD<10%.

Example 3

Exemplary Eroding formulations prepared by Direct Compression

For purposes of illustration, a number of exemplary eroding placebo formulations prepared by the method of direct compression are provided below in Tables 6-9. For each of the formulations, all excipients were weighed, ground with a mortar and pestle for 1-2 minutes manually mixed; the formulation included a small amount of a colorant (aluminum blue lake) as a surrogate for the active drug substance. 5.5-8.0 mg aliquots of the dry blend were weighed, loaded in a specially constructed load cell and were compressed in a Carver press at 5-20K psi. to form a dosage form. Exemplary formulations prepared using this methodology are provided in Tables 6-9 below as % w/w compositions of the excipients, wherein Tables 10 and 11 provide exemplary hydrogel formulations.

TABLE 6

Exemplary Eroding Formulations prepared by Direct Compression

| Ingredient | #1 | #2 | #3 | #4 | #5 | #6 | #7 |
|---|---|---|---|---|---|---|---|
| | Composition, % w/w | | | | | | |
| Aluminum blue lake (dye) | 0.10 | 0.10 | 0.10 | 0.10 | 0.10 | 0.10 | 0.10 |
| Mannitol | 60.00 | 60.00 | 60.00 | 60.00 | 60.00 | 60.00 | 60.00 |
| Carbopol 934 | | | | 10.00 | | | |
| Carbopol 974 | 10.00 | 10.00 | 10.00 | | 10.00 | 10.00 | 10.00 |
| HPMC - 2910 | | 13.90 | | | 5.00 | | |
| PEG 8000 | 28.90 | 15.00 | 15.00 | 15.00 | 23.90 | 23.90 | 23.90 |
| PVP K90 | | | 13.90 | | | 5.00 | |
| CMC | | | | 13.90 | | | 5.00 |
| Mg Stearate | 1.00 | 1.00 | 1.00 | 1.00 | 1.00 | 1.00 | 1.00 |
| Total | 100 | 100 | 100 | 100 | 100 | 100 | 100 |

TABLE 7

Exemplary Eroding Formulations prepared by Direct Compression

| Ingredient | #8 | #9 | #10 | #11 | #12 |
|---|---|---|---|---|---|
| | Composition, % w/w | | | | |
| Aluminum blue lake (dye) | 0.10 | 0.10 | 0.10 | 0.10 | 0.10 |
| Mannitol | 63.90 | 55.00 | 60.00 | 60.00 | 57.50 |
| Dibasic Calcium Phosphate | | | | 28.90 | |
| Carbopol 934 | 20.00 | 15.00 | 10.00 | 10.00 | 12.50 |
| HPMC - 2910 | | | | | |
| PEG 8000 | 15.00 | 28.90 | 28.90 | | 28.90 |
| Mg Stearate | 1.00 | 1.00 | 1.00 | 1.00 | 1.00 |
| Total | 100 | 100 | 100 | 100 | 100 |

TABLE 8

Exemplary Eroding Formulations prepared by Direct Compression

| Ingredient | #13 | #14 | #15 | #16 | #17 | #18 | #19 | #20 | #21 |
|---|---|---|---|---|---|---|---|---|---|
| | | | | Composition, % w/w | | | | | |
| Aluminum blue lake (dye) | 0.10 | 0.10 | 0.10 | 0.10 | 0.10 | 0.10 | 0.10 | 0.10 | 0.10 |
| Mannitol | 50.00 | 50.00 | 30.00 | 20.00 | 30.00 | 30.00 | 30.00 | 30.00 | 30.00 |
| Cholesterol | | | | | | | | | |
| Dibasic Calcium Phosphate | | | 38.90 | 30.00 | 38.90 | 38.90 | 38.90 | 38.90 | 30.00 |
| Stearic Acid | | | | 18.90 | | | | | |
| Carbopol 934 | 30.00 | 40.00 | 30.00 | 30.00 | | | | | |
| Carbopol 971 | | | | | 30.00 | | | | |
| HPMC - 2910 | | | | | | | | | |
| HPMC - K4 | | | | | | 30.00 | | | |
| HPMC - E3 | | | | | | | 30.00 | | |
| NA-CMC | | | | | | | | 30.00 | |
| PEG 8000 | 18.90 | 8.90 | | | | | | | |
| Mg Stearate | 1.00 | 1.00 | 1.00 | 1.00 | 1.00 | 1.00 | 1.00 | 1.00 | 1.00 |
| Total | 100 | 100 | 100 | 100 | 100 | 100 | 100 | 100 | 100 |

TABLE 9

Exemplary Eroding Formulations prepared by Direct Compression

| Ingredient | #22 | #23 | #24 | #25 |
|---|---|---|---|---|
| | Composition, % w/w | | | |
| Aluminum blue lake (dye) | 0.10 | 0.10 | 0.10 | 0.10 |
| Mannitol | 50.00 | | 50.00 | 50.00 |
| Dibasic Calcium Phosphate | | 28.90 | 23.90 | |
| Stearic Acid | | | | 23.90 |
| Carbopol 934 | 25.00 | 20.00 | 25.00 | 25.00 |
| PEG 8000 | 23.90 | | | |
| Mg Stearate | 1.00 | 1.00 | 1.00 | 1.00 |
| Total | 100 | 100 | 100 | 100 |

Example 4

Exemplary Hydrogel Formulations Prepared by Direct Compression

For purposes of illustration a number of exemplary hydrogel placebo formulations prepared by the method of direct compression are provided below in Tables 10-11. For each of the formulations, all excipients were weighed, ground with a mortar and pestle for 1-2 minutes and manually mixed; the formulations included a small amount of a colorant (aluminum blue lake) as a surrogate for the active drug substance. 5.5-8.0 mg aliquots of the dry blend were weighed, loaded in a specially constructed load cell and were compressed in a Carver press at 5-20K psi to form a dosage form. Exemplary formulations prepared by this methodology are provided in Tables 10-11 below as % w/w compositions of the excipients. For purposes of illustration a number of exemplary eroding placebo formulations prepared by the method of wet granulation are provided in Table 12. In a typical preparation, a full wet granulation was employed. In such a process, the aluminum lake dye (acting as the drug surrogate) was dissolved in the appropriate diluent (water, EtOH or hydroalcoholic mixtures of a number of ratios) and was added either via direct pouring or by spraying onto the dry blend of the remaining excipients. The wet mix was then mixed in a high-shear mixer and processed to form granules of the desired size, in a high shear granulator (such as the KG-5). The formed granules were then dried in a tray oven and mixed. The final mix was fed to a Piccola rotary press (or a beta press) equipped with the specially designed load cell to enable the preparation of dosage forms. To achieve that approximately 5.5-8.0 mg of the dried granules were compressed at 1-20 KN. For some of the examples below additional excipients, such as the binder or the bioadhesive, were included in the solution that was poured over the dry blend of excipients.

TABLE 10

Exemplary Hydrogel Formulations Prepared by Direct Compression

| Ingredient | #26 | #27 | #28 | #29 | #30 | #31 |
|---|---|---|---|---|---|---|
| | Composition, % w/w | | | | | |
| Aluminum blue lake (dye) | 0.10 | 0.10 | 0.10 | 0.10 | 0.10 | 0.10 |
| Mannitol | 58.00 | 53.00 | 63.00 | 30.00 | 40.00 | 40.00 |
| Dibasic calcium phosphate | | | | 29 | 34 | 34 |
| Stearic Acid | 5.00 | 10.00 | | | | |
| PEG 8000 | 28.90 | 28.90 | 28.90 | | | |
| Pluronic F68 | 2.00 | 2.00 | 2.00 | | | |
| Polyox 80 | 5.00 | 5.00 | 5.00 | 25 | | |
| Polyox 301 | | | | | 25 | |
| Polyox 303 | | | | | | 25 |
| PVP K90 | | | | 15 | | |
| Mg Stearate | 1.00 | 1.00 | 1.00 | 1.00 | 1.00 | 1.00 |
| Total | 100 | 100 | 100 | 100.10 | 100.10 | 100.10 |

TABLE 11

Exemplary Eroding & Hydrogel Formulations Prepared By Full Wet Granulation

| Formulation # | Eroding #32 | Hydrogel #33 | Hydrogel #34 | Hydrogel #35 | Hydrogel #36 |
|---|---|---|---|---|---|
| | | | Formulation Type | | |
| Pour/spray solution | Dye solution | Dye + binder solution | Water | Water | Water |
| Granulation | Low Shear | Low shear | High Shear | High Shear | High Shear |
| Excipient | | | Composition, % w/w | | |
| FDC Green (dye) | 0.07 | 0.07 | 0.07 | 0.07 | 0.07 |
| Mannitol (Pearlitol 100SD) | 60.10 | 58.00 | | | |
| Mannitol (Pearlitol 200SD) | | | 58.00 | 58.00 | |
| Mannitol (Pearlitol 160C) | | | | | 73.93 |
| PEG 8000 | 28.83 | 28.93 | 23.93 | 23.93 | 15.00 |
| PVP K90 | | | 5.00 | 5.00 | |
| Carbopol 974 | 10.00 | | | | |
| Polyox 303 | | 5.00 | 5.00 | 5.00 | 3.00 |
| Lutrol F68 | | 2.00 | 2.00 | 2.00 | 2.00 |
| Stearic Acid | | 5.00 | 5.00 | 5.00 | 5.00 |
| Mg Stearate | 1.00 | 1.00 | 1.00 | 1.00 | 1.00 |
| Total | 100.00 | 100.00 | 100.00 | 100.00 | 100.00 |

Example 5

Exemplary Eroding & Hydrogel Formulations Prepared by Wet Granulation

Further, a number of different grades and particle sizes of mannitol can be employed to help optimize the granulation process. In the examples provided below, the mannitol grades were varied (Pearlitol 100SD, Pearlitol 200SD or Pearlitol 160C) obtain different quality granules (size, distribution, etc.).

As is well-known to those skilled in the art, there is a number of process alterations that could be used in this process. In one such alteration, a partial wet granulation was employed to prepare dosage forms. In this process only a portion of the excipients was used in the formation of the granules (intra-granular mix). In such process, the remaining excipients were added extra-granularly to the granules and the mix would be blended for a few minutes in order to create a homogeneous matrix. The formulation examples given below (Table 8) also reflect partial granulation process.

TABLE 12

Exemplary Hydrogel Formulations Prepared By Partial Wet Granulation

| Excipient | #37 | #38 | #39 | #40 | #41 | #42 |
|---|---|---|---|---|---|---|
| | | | Composition, % w/w | | | |
| FDC Green (dye) | 0.05 | 0.05 | 0.05 | 0.05 | 0.05 | 0.05 |
| Mannitol (Pearlitol 100SD) | | | | | 73.95 | 68.96 |
| Mannitol (Pearlitol 200SD) | 73.95 | 73.6 | 75.45 | 73.95 | | |
| PEG 8000 | 15 | 14.93 | 15.00 | 15.00 | 15.00 | 20.00 |
| Microcrystalline Cellulose (MCC-Emcel 90M) | | 7.44 | | | | |
| Polyox 303 | 3 | 2.99 | 1.50 | 3.00 | 3.00 | 3.00 |
| Lutrol F68 | 2 | | 2.00 | 2.00 | 2.00 | 2.00 |
| Stearic Acid | 5 | | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |

Example 6

Exemplary Hydrogel Formulations Prepared with Active Substance: Sufentanil Citrate For purposes of illustration, a number of formulations were prepared with active drug substance. The drug substance used in these examples is sufentanil citrate. The formulations, which are described in Table 13, were prepared for the sake of illustration using the same partial wet granulation methodology as described above and as detailed in the Table.

TABLE 13

Exemplary Hydrogel Formulations Prepared With Sufentanil Citrate

| Ingredient | #43 | #44 | #45 | #46 | #47 | #48 |
|---|---|---|---|---|---|---|
| | | | Composition, % w/w | | | |
| Sufentanil Citrate | 0.05 | 0.27 | 0.14 | 0.068 | 0.136 | 0.273 |
| Mannitol (Pearlitol 100SD) | 73.96 | — | — | 73.9 | 73.86 | 73.7 |
| Mannitol (Pearlitol 200SD) | — | 73.77 | 73.87 | — | — | — |
| PEG 8000 | 15 | 14.98 | 15.00 | 15.00 | 15.00 | 15.00 |
| Polyox 303 | 3.00 | 3.00 | 3.00 | 3.00 | 3.00 | 3.00 |
| Lutrol F68 | 2.00 | 2.00 | 2.00 | 2.00 | 2.00 | 2.00 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |

In Vitro Evaluations of Transmucosal Formulations

A number of placebo formulations of both eroding and hydrogel-type were prepared using direct compression and/or wet granulation and their properties were evaluated in vitro for bioadhesion and in vitro drug dissolution kinetics using the procedures outlined above.

TABLE 14

Exemplary Placebo Formulations for Evaluations In Vitro.

| Composition | Formulation # | | | | | |
|---|---|---|---|---|---|---|
| | 49 | 50 | 51 | 47 | 52 | 53 |
| | Composition, % w/w | | | | | |
| Aluminum Lake Dye | 0.14 | 0.14 | 0.14 | 0.14 | 0.14 | 0.14 |
| Mannitol | 83.87 | 68.87 | 56.87 | 73.86 | 51.9 | 40.7 |
| Carbopol 971 | | | 7.00 | | 20.00 | 20.00 |
| PEG 8000 | 5.00 | | 35.00 | 15.00 | 15.00 | 25.60 |
| HPMC | 10.00 | 5.00 | | | | 10.00 |
| Dibasic Calcium Phosphate | | 20.00 | | | | |
| Polyox 303 | | | | 3.00 | | 2.60 |
| Lutrol F68 | | | | 2.00 | 7.00 | |
| Stearic Acid | | 5.00 | | 5.00 | 5.00 | |
| Mg Stearate | 1.00 | 1.00 | 1.00 | 1.00 | 1.00 | 1.00 |
| Total | 100.00 | 100.00 | 100.00 | 100.00 | 100.00 | 100.00 |

Example 7

In Vitro Evaluation of Bioadhesion

The mucoadhesive strength was determined by attaching the tablets to the bottom of a hanging platform and determining the force required to detach the formulations from a porcine buccal mucosa substrate. The mucoadhesive testing system is consisting of a precision load cell (GS-500 Tranducer techniques, Temecula, Calif.) and a hook attachment The load cell generates analogue signals, which are converted into digital signals through a data acquisition system equipped with an A/D converter and a computer; data are analyzed using EasyLx software (Keithley Metrabyte). A hanging platform comprising a glass slide attached with plastic plunger (8 cm) on the top and a circular-steel projection (0.5 cm) with flat surface on the bottom is attached to the load cell. A flat-surfaced tablet die serves as a lower static-platform. The mucosal tissue is mounted onto the lower platform using a screw-clamp. The hanging platform with the film is brought down and placed over the surface of the mucosa with a known applied force for a specified time. The detachment force in N/cm$^2$ is determined and compared. Between each measurement, the mucosal surface is rinsed with 4 mL, of purified water. The excess water is wiped with a soft tissue paper and the mucosa is wetted with a known volume of phosphate buffer pH 6.8. Studies are performed in triplicate at room temperature (23-25° C.). Adhesion and peak detachment force can be used to evaluate the bioadhesive strength of dosage forms comprising various formulations of the invention. A dosage form of the invention expresses bioadhesion forces greater than 100 dynes/cm$^2$, eg 500 dynes/cm$^2$.

The bioadhesive strength of the placebo formulations was evaluated and the results are given in Table 15.

TABLE 15

Bioadhesion force of placebo Formulations.

| Formulation # | Bioadhesion force, N/cm$^2$ |
|---|---|
| 49 | 0.040 ± 0.01 |
| 47 | 0.046 ± −0.01 |
| 52 | 0.162 ± 0.15 |
| 50 | 0.030 ± 0.00 |
| 51 | 0.056 ± 0.01 |
| 53 | 0.180 ± 0.08 |

Example 8

Evaluation of Sufentanil Dissolution In Vitro from Formulations

Figure 11:
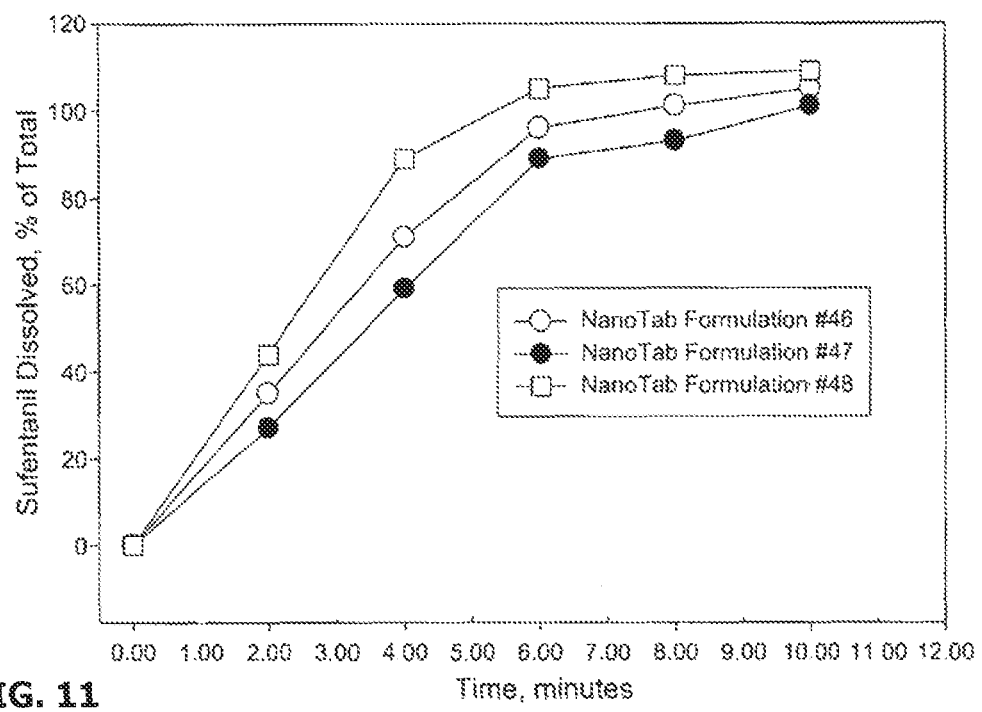
FIG. 11 is a graphic depiction of the in vitro dissolution kinetics of a NanoTab® comprising formulations #46-#48.

Sufentanil dissolution kinetics from formulations #46, #47 and #48 was determined in a Type II LISP dissolution apparatus suitably modified to accommodate a small volume NanoTab® containing a small amount of sufentanil. Drug release from the bioadhesive transmucosal formulations were monitored by LC/MS. The dissolution medium was defined as phosphate buffer pH between 6.5-7.8. A dosage form of the invention has a dissolution time that typically occurs in up to about 60 minutes, however, in some cases dissolution is evident after up to about 120 minutes or 240 minutes. The results are shown in FIG. 11.

Example 9

Bioavailability and Pharmacokinetics of Sufentanil Following Sublingual Administration of Formulations in a Healthy Dog Model The bioavailability of sufentanil following sublingual administration from formulation #44 as compared to intravenous was evaluated in a healthy, conscious Beagle dog animal model, as described in Table 16. Intravenous administrations were performed by single administration (n=3) of Sufenta® 50 μg/mL by bolus injection to the cephalic vein via a sterile needle and syringe of appropriate size at a dose of 5 μg of sufentanil base). For the sublingual administrations (Group 2) the test article (Formulation #44 strength of 5 μg of sufentanil base) was administered sublingually (n=3) by placement under the tongue, on to the frenulum via forceps. Blood samples were collected from a jugular or other suitable vein prior to dosing and approximately 1, 3, 5, 10, 15, 30 min, 1, 2, 4, 8 and 24 hours post-dose. Approximately 2 mL of blood were collected per time point into pre-chilled tubes containing K$_2$ EDTA. The samples were centrifuged at 3,000 g for approximately 10 minutes in a refrigerated centrifuge. Plasma was collected and frozen within 20 minutes of centrifugation at approximately −70° C. and was maintained at that temperature until analysis. Sample analysis was performed using a validated LC/MS/MS method for analysis of sufentanil in dog plasma.

TABLE 16

Dosing Parameters for Administration of Sufentanil (i) by sublingual administration from Sublingual Bioadhesive Formulation #44 and (ii) by an intravenous solution.

| Group | Treatment | Dose Level (μg)[a] | Route of Administration | Number of Animals[b] (Males) |
|---|---|---|---|---|
| 1 | Sufentanil solution | 5.0 | IV | 3 |
| 2 | Sufentanil NanoTab ® | 5.0 | Sublingual | 3 |

[a] = Expressed as a free base.
[b] = Same animals will be used for Groups 1 through 3 with a minimum 2-day washout period between dosing.

Figure 12:
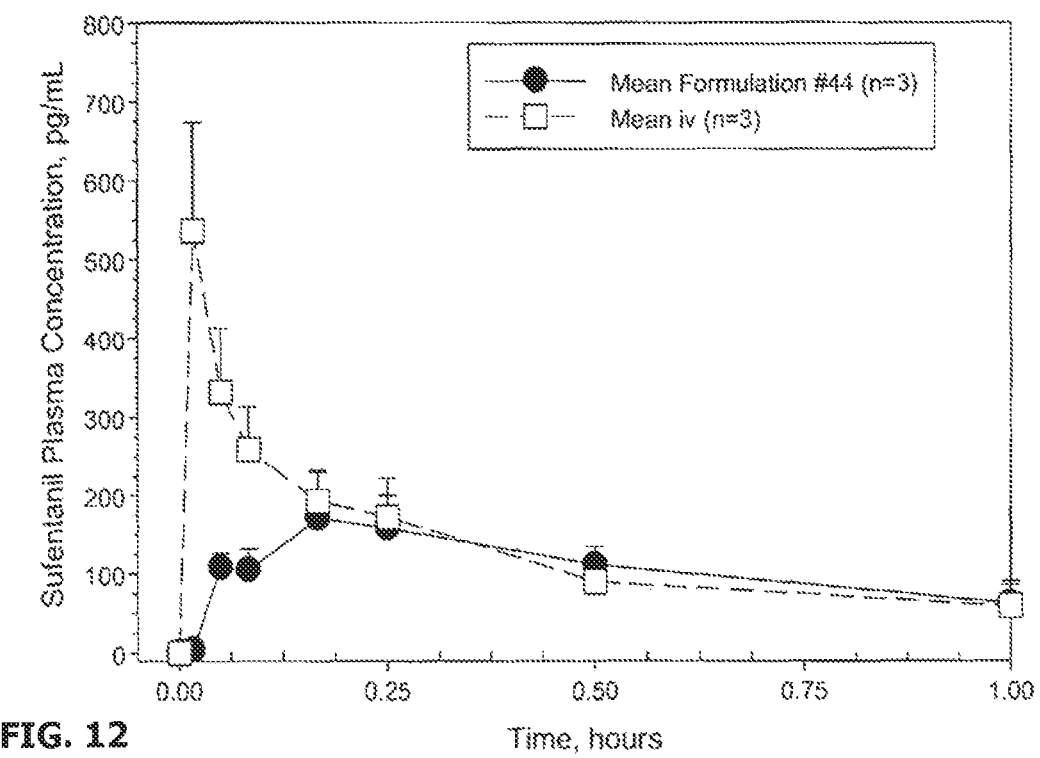
FIG. 12 is a graphic depiction of the pharmacokinetics of sufentanil following sublingual administration (n=3) of a NanoTab® comprising formulation #44, as compared to intravenous administration (n=3) in a healthy, conscious Beagle dog model. Error bars represents standard errors around the mean (SEM).

The plasma PK profiles are shown in FIG. 12. PK analysis results are summarized in Table 17.

TABLE 17

PK Analysis of Sufentanil sublingual formulation (#44) compared to intravenous sufentanil.

| Group | F (%) | Absorption Variability (% CV) | $C_{max}$ (pg/mL) | $T_{onset}$ (min)[1] | $T_{max}$ (min) | Plasma Half-life (min) | Therapeutic Time Ratio[2] |
|---|---|---|---|---|---|---|---|
| Intravenous Sufentanil | — | 22.8 | 536.7 ± 186.1 | 0.05 ± 0.06 | 1.6 ± 0.6 | 10.3 ± 4.5 | 0.05 ± 0.02 |
| Sublingual Sufentanil Formulation #44 | 74.8 ± 10.7 | 14.4 | 222.7 ± 25.9 | 7.1 ± 4.0 | 11.7 ± 2.5 | 33.3 ± 5.8 | 0.28 ± 0.16 |

[1] Time to reach 50% of $C_{max}$
[2] Represents the relative time that the drug achieves therapeutic levels (above 50% $C_{max}$), defined as time within which the drag plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 10

Bioavailability and Pharmacokinetics of Sufentanil Following Sublingual Solution Instillation in a Healthy Dog Model For purposes of comparison to the sufentanil dosage forms, the bioavailability and pharmacokinetics of sufentanil citrate after sublingual administration via instillation of a sufentanil solution (n=6) was evaluated and compared to IV (n=6). The bioavailability of sufentanil following sublingual administration from a solution as compared to that intravenously was evaluated in a healthy, conscious Beagle dog animal model, as described in Table 18. In both arms of the study the commercially available formulation of sufentanil citrate (Sufenta® 50 μg/mL) was used and was dosed at the same total dose of 5 μg of sufentanil base. Intravenous administrations were performed by single administration (n=3) of Sufenta® 50 μg/mL by bolus injection to the cephalic vein via a sterile needle and syringe of appropriate size. Doses were slowly applied under the tongue, adjacent to the frenulum via a sterile syringe. Blood sampling and storage mirrored the conditions described in Example #9 sample analysis was performed using a validated LC/MS/MS method for analysis of sufentanil in dog plasma.

TABLE 18

Dosing Parameters for Administration of Sufentanil (i) by sublingual administration via instillation of a sufentanil solution, (ii) by oral ingestion of a NanoTab ® formulation and (ii) by an intravenous solution.

| Group | Treatment | Dose Level (μg)[a] | Route of Administration | Total Number of Animals, n |
|---|---|---|---|---|
| 1 | Sufentanil solution | 5.0 | IV | 3 |
| 2 | Sufentanil solution[c] | 5.0 | Sublingual | 6[b] |

TABLE 18-continued

Dosing Parameters for Administration of Sufentanil (i) by sublingual administration via instillation of a sufentanil solution, (ii) by oral ingestion of a NanoTab ® formulation and (ii) by an intravenous solution.

| Group | Treatment | Dose Level (μg)[a] | Route of Administration | Total Number of Animals, n |
|---|---|---|---|---|
| 3 | Ingested Formulation #44 | 5.0 | Oral | 6[b] |

[a] = Expressed as a tree base.
[b] = Group 2 & 3 animals were dosed twice with a minimum 2-day washout period for a total of n = 6
[c] = Normal saline was used to dilute the test article (Sufenta ® 50 μg/mL) to the desired concentration.

The analytical results are shown in FIG. 3. PK analysis results are summarized in Table 19.

TABLE 19

PK Analysis of intravenously administered sufentanil compared to (i) a sublingually instilled solution and (ii) an ingested NanoTab ®

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Sufentanil | — | 39.9 | 0.5 ± 0.03 | 1.0 ± 0.0 | 594.7 ± 98.1 | 2.8 ± 0.4 | 0.02 ± 0.0 |
| Sublingual Sufentanil solution | 40.0 ± 32.5 | 81.3 | 2.7 ± 1.3 | 4.3 ± 1.0 | 209.3 ± 165.5 | 8.3 ± 4.5 | 0.04 ± 0.02 |
| Ingested NanoTab ® | 12.2 ± 16.3 | 134.2 | — | 14.6 ± 9.9 | 33.8 ± 33.2 | 22.5 ± 16.8 | 0.13 ± 0.08 |

[1]Time to reach 50% of $C_{max}$
[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 11

Evaluation of the Bioavailability and Pharmacokinetics of Sufentanil Following Oral Ingestion of a Sufentanil Transmucosal Formulation The bioavailability of sufentanil following ingestion of a bioadhesive tablet described in this invention (formulation #44) as compared to that intravenously was evaluated in a healthy, conscious Beagle dog animal model, as described in the previous example. A single bioadhesive formulation prepared at a total strength of 5.0 μg of sufentanil (base units) was administered twice orally, with each dose separated by a minimum of a 2-day washout for a total of n=6 (Table 18). The bioadhesive tablets were placed manually as far back as possible in the throat and flushed with water to promote the swallow response in the animal.

Example 12

Exemplary Sufentanil Formulations to Control Drug Release and In Vivo Pharmacokinetics For purposes of illustration, a number of formulations were prepared with sufentanil citrate in order to evaluate the rate of drug release and in vivo pharmacokinetics of various dosage forms. Both eroding and hydrogel-based formulations, as described in Table 20, were prepared by direct compression, as described in Example 3, except for formulation #56, which was prepared by wet granulation, as described in Example 5.

TABLE 20

Exemplary Sufentanil Dosage Forms for Evaluation of In Vivo Drug Pharmacokinetics.

| | Formulation # | | | | |
|---|---|---|---|---|---|
| | 54 | 55 | 56 | 57 | 58 |
| Composition | Composition, % w/w | | | | |
| Sufentanil citrate | 0.2728 | 0.2728 | 0.1364 | 0.5456 | 0.5456 |
| Mannitol | 83.73 | 68.73 | 56.87 | 51.45 | 40.3 |
| Carbopol 971 | | | 7.00 | 20.00 | 20.00 |
| PEG 8000 | 5.00 | | 35.00 | 15.00 | 25.60 |
| HPMC K4M | 10.00 | 5.00 | | | 10.00 |
| Dibasic Calcium Phosphate | | 20.00 | | | |
| Polyox 303 | | | | | 2.60 |
| Lutrol F68 | | | | 7.00 | |
| Stearic Acid | | 5.00 | | 5.00 | |
| Mg Stearate | 1.00 | 1.00 | 1.00 | 1.00 | 1.00 |
| Total | 100.00 | 100.00 | 100.00 | 100.00 | 100.00 |

The pharmacokinetics of sufentanil following sublingual administration of formulations #54-58 were evaluated in a healthy, conscious Beagle dog animal model, as described in Table 21. Intravenous administrations were performed by single administration (n=3) of Sufenta® 50 μg/mL (total dose of 5 μg of sufentanil base) by bolus injection to the cephalic vein via a sterile needle and syringe of appropriate size. For the sublingual administrations the test articles (n=2 or 3) were placed under the tongue, adjacent to the frenulum via forceps. Blood sampling and storage mirrored the conditions described in Example #9; sample analysis was performed using a validated LC/MS/MS method for analysis of sufentanil in dog plasma.

TABLE 21

Dosing Parameters for Administration of Sufentanil (i) via sublingual administration of fast (#55), intermediate (#54) and slow (#58) formulations and (ii) by an intravenous solution.

| Group | Treatment | Dose Level (μg)[a] | Route of Administration | Dose Concentration (μg/mL) | Number of Animals (Males) |
|---|---|---|---|---|---|
| 1 | Sufenta ® | 5 | IV | 50[a] | 3 |
| 2 | Sufentanil-Formulation #54 | 11.0 ± 0.9 | Sublingual | NA | 3 |
| 3 | Sufentanil Formulation #55 | 10.6 ± 0.6 | Sublingual | NA | 3 |
| 6 | Sufentanil Formulation #58 | 30.9 ± 1.4 | Sublingual | NA | 3 |

[a]Expressed as a free base.

Figure 14:
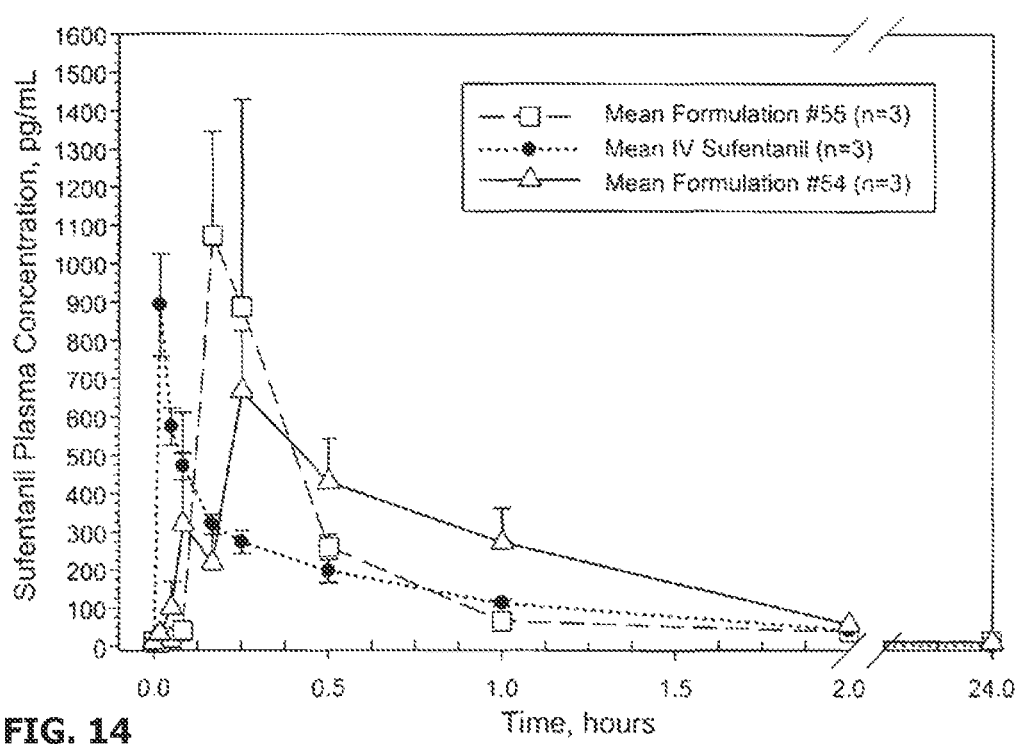
FIG. 14 is a graphic depiction of the pharmacokinetics of sufentanil following sublingual administration of fast-disintegrating NanoTab® formulation #55 (n=3) and intermediate-disintegrating NanoTab® formulation #54 (n=3), as compared to intravenous administration (n=3) in a healthy, conscious Beagle dog model. Error bars represent standard errors around the mean.
Figure 15:
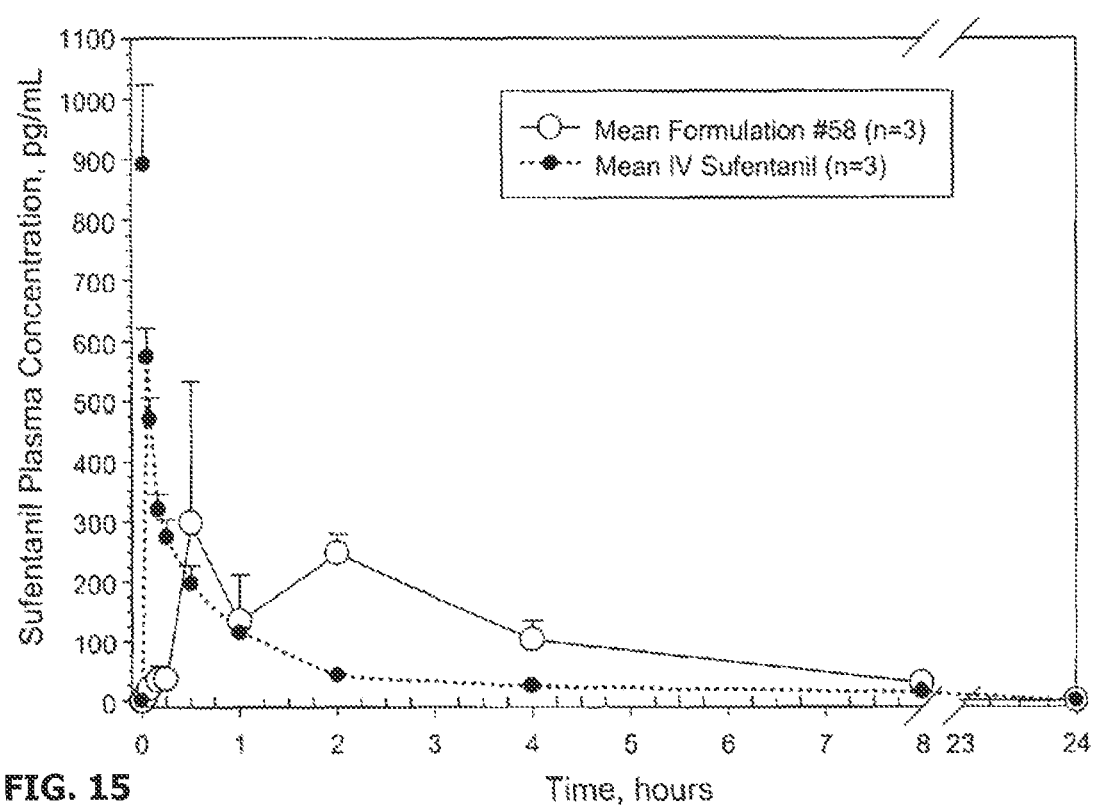
FIG. 15 is a graphic depiction of the pharmacokinetics of sufentanil following sublingual administration of slowly-disintegrating NanoTab® formulation #58 (n=3), as compared to intravenous administration of sufentanil (n=3) in a healthy, conscious Beagle dog model. Error bars represent standard errors around the mean.

The results are shown in FIGS. 14 and 15. PK results are summarized in Tables 22 and 23.

TABLE 22

PK Analysis sublingual fast- and intermediate-disintegrating Sufentanil formulations compared to intravenously administered Sufenta ®.

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Sufentanil | — | 5.4 | 0.6 ± 0.0 | 1.0 ± 0.0 | 1002.1 ± 149.1 | 7.9 ± 2.5 | 0.05 ± 0.02 |
| Sublingual Formulation #54 | 88.2 ± 28.9 | 32.8 | 9.2 ± 4.3 | 25 ± 8.7 | 727.2 ± 256.3 | 49.2 ± 22.0 | 0.28 ± 0.13 |
| Sublingual Formulation #55 | 90.4 ± 25.3 | 28 | 7.1 ± 0.5 | 13.3 ± 2.9 | 819.1 ± 100.1 | 26.7 ± 2.2 | 0.14 ± 0.02 |

[1]Time to reach 50% of $C_{max}$
[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

TABLE 23

PK Analysis sublingual slow-disintegrating Sufentanil formulations compared to intravenously administered Sufenta ®.

| Group | $T_{onset}$ (min)[1] | $T_{max}$ (min) | $C_{max}$ (pg/mL) | Plasma Half-life (min) | Therapeutic Time Ratio[2] |
|---|---|---|---|---|---|
| Intravenous Sufentanil | 0.6 ± 0.0 | 1.0 ± 0.0 | 1002.1 ± 149.1 | 7.9 ± 2.5 | 0.05 ± 0.02 |
| Sublingual Formulation #58 | 48 ± 34.1 | 70 ± 45.8 | 420.9 ± 298.4 | 205 ± 93.1 | 1.13 ± 0.69 |

[1]Time to reach 50% of $C_{max}$
[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 13

In vivo Evaluation of Sublingual Fentanyl Formulations in a Dog Model

For purposes of illustration, a number of transmucosal formulations were prepared with fentanyl citrate in order to evaluate the rate of drug release and in vivo pharmacokinetics various dosage forms. Both eroding and hydrogel-based formulations, as described in Table 24, were evaluated; all dosage forms were prepared by direct compression, as described in Example 3.

TABLE 24

Exemplary Fentanyl Formulations for Evaluation In Vivo.

| | Formulation # | | |
|---|---|---|---|
| | 59 | 60 | 62 |
| Composition | Composition, % w/w | | |
| Fentanyl citrate | 2.00 | 2.00 | 2.00 |
| Mannitol | 72.00 | 55.00 | 38.80 |
| Carbopol 974 | | 7.00 | 20.00 |
| PEG 8000 | 15.00 | 35.00 | 25.60 |
| HPMC K4M | | | 10.00 |
| Polyox 303 | 3.00 | | 2.60 |
| Lutrol F68 | 2.00 | | |
| Stearic Acid | 5.00 | | |
| Mg Stearate | 1.00 | 1.00 | 1.00 |
| Total | 100.00 | 100.00 | 100.00 |

The pharmacokinetics of fentanyl following sublingual administration from a number of formulations intended to provide distinct PK profiles as compared to that intravenously was evaluated in a healthy, conscious Beagle dog animal model, as described in Table 25. The commercially available formulation of fentanyl citrate (Sublimaze® 50 µg/mL) was used and was dosed at the same total dose of 70 µg of fentanyl base. Intravenous administrations were performed by single administration (n=3) of Sublimaze® 50 µg/mL by bolus injection to the cephalic vein via a sterile needle and syringe of appropriate size. Both hydrogel and eroding formulations were developed to provide intermediate and slow release of the drug from the dosage form. For the sublingual administrations the test articles were administered sublingually (n=2 or 3) by placement under the tongue, adjacent to the frenulum via forceps. Blood sampling and storage mirrored the conditions described in Example 9; sample analysis was performed using a validated LC/MS/MS method for analysis of fentanyl in dog plasma.

TABLE 25

Dosing Parameters for Administration of Fentanyl (i) via sublingual administration of intermediate (#59, 60) and slow-acting (#62) formulations and (ii) by an intravenous solution.

| Group | Treatment | Dose Level (µg)[a] | Route of Administration | Dose Volume (mL) | Dose Concentration (µg/mL) | Number of Animals (Males) |
|---|---|---|---|---|---|---|
| 1 | Sublimaze ® | 70 | IV | 14 | 50[a] | 3 |
| 2 | Fentanyl-Formulation #59 | 74.1 ± 3.6 | Sublingual | NA | NA | 2 |
| 3 | Fentanyl Formulation #60 | 74.7 ± 3.8 | Sublingual | NA | NA | 2 |
| 5 | Fentanyl Formulation #62 | 69.3 ± 5.6 | Sublingual | NA | NA | 3 |

[a]Expressed as a free base.

Figure 16:
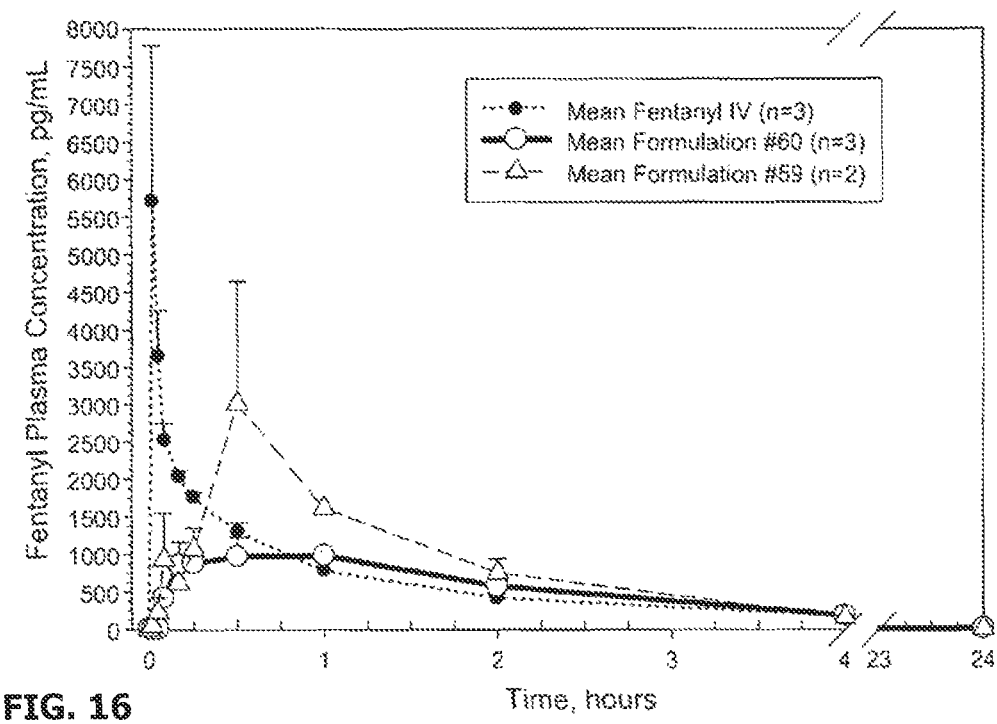
FIG. 16 is a graphic depiction of the pharmacokinetics of fentanyl following sublingual administration from medium-disintegrating NanoTab® formulations #59 (n=2) and formulation #60 (n=3), as compared to fentanyl intravenous administration (n=3) in a healthy, conscious Beagle dog model. Error bars represent standard errors around the mean.
Figure 17:
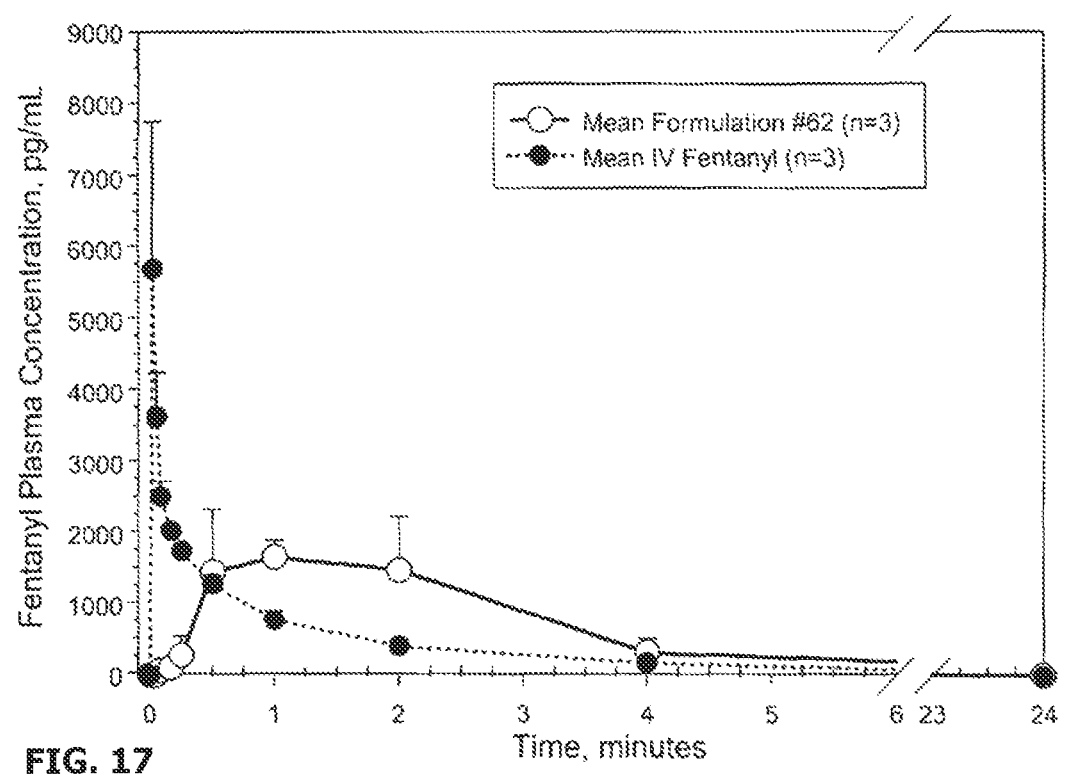
FIG. 17 is a graphic depiction of the pharmacokinetics of fentanyl following sublingual administration from slow-disintegrating NanoTab® formulation #62 (n=3) as compared to intravenous fentanyl administration (n=3) in a healthy, conscious Beagle dog model. Error bars represent standard errors around the mean.

The results are shown in FIGS. 16 and 17. Pharmacokinetic analysis results are summarized in Table 26.

TABLE 26

PK Analysis of sublingually administered Fentanyl formulations as compared to intravenous Sublimaze ®.

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Fentanyl | — | 13.7 | 0.6 ± 0.0 | 1.0 ± 0.0 | 7895.9 ± 6096 | 10.5 ± 9.6 | 0.04 ± 0.04 |
| Sublingual Formulation #59 | 96.9 ± 8.2 | 8.4 | 16.2 ± 6.8 | 45 ± 21.2 | 3304.5 ± 2398 | 75.5 ± 32.5 | 0.24 ± 0.16 |
| Sublingual Formulation #60 | 95.4 ± 10 | 10.5 | 9.0 ± 2.6 | 22.5 ± 10.6 | 1188.2 ± 42.4 | 121.5 ± 19.1 | 0.46 ± 0.07 |
| Sublingual Formulation #62 | 99.0 ± 4.4 | 4.5 | 43.6 ± 20.7 | 50 ± 17.3 | 2226.9 ± 811.5 | 154.4 ± 52.6 | 0.46 ± 0.12 |

[1]Time to reach 50% of $C_{max}$
[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature intravenous studies of fentanyl to be 244 min in beagle dogs.

The pharmacokinetics of sublingual fentanyl from medium-disintegrating NanoTabs® are illustrated in FIG. 16. The pharmacokinetics of sublingual fentanyl from slow-disintegrating NanoTabs® are illustrated in FIG. 17.

Example 14

In vivo Evaluation of Sublingual Alfentanil HCl Formulations in a Dog Model

For purposes of illustration, an eroding dosage form was prepared with alfentanil HCl in order to demonstrate the ability of the dosage forms described in this application to modulate and control the rate of drug release and ultimately in vivo pharmacokinetics. The formulation composition is described in Table 27; all tablets were prepared by direct compression, as described in Example 3.

TABLE 27

Exemplary Alfentanil Formulations for Evaluation of In Vivo Drug Pharmacokinietics.

| Composition | Formulation # 63 Composition, % w/w |
|---|---|
| Alfentanil HCl | 5.00 |
| Mannitol | 52.00 |
| Carbopol 974 | 7.00 |
| PEG 8000 | 35.00 |
| Mg Stearate | 1.00 |
| Total | 100.00 |

The bioavailability and pharmacokinetics of alfentanil following sublingual administration from a formulation as compared to that intravenously was evaluated in a healthy, conscious Beagle dog animal model, as described in Table 28. Intravenous administrations were performed by single administration (n=3) of Alfentanil HCl (Alfenta® 500 µg/mL by bolus injection to the cephalic vein via a sterile needle and syringe of appropriate size at a dose of 253 µg of alfentanil base). For the sublingual administrations the test article (Formulation #63, strength of 239±16.2 µg of alfentanil base) was administered sublingually (n=2) by placement under the tongue, adjacent to the frenulum via forceps. Blood sampling and storage mirrored the conditions described in Example 9; sample analysis was performed using a validated LC/MS/MS method for analysis of alfentanil in dog plasma.

TABLE 28

Dosing Parameters for Administration of Alfentanil (i) sublingually from a formulation and (ii) by an intravenous solution.

| Group | Treatment | Dose Level (μg)[a] | Route of Administration | Number of Animals (Males) |
|---|---|---|---|---|
| 1 | Alfentanil solution | 253 | IV | 3 |
| 2 | Alfentanil Formulation | 239.0 ± 16.2 | Sublingual | 2 |

[a]= Expressed as a free base.
[b]= Same animals will be used for Groups 1 through 3 with a minimum 2-day washout period between dosing.

Figure 18:
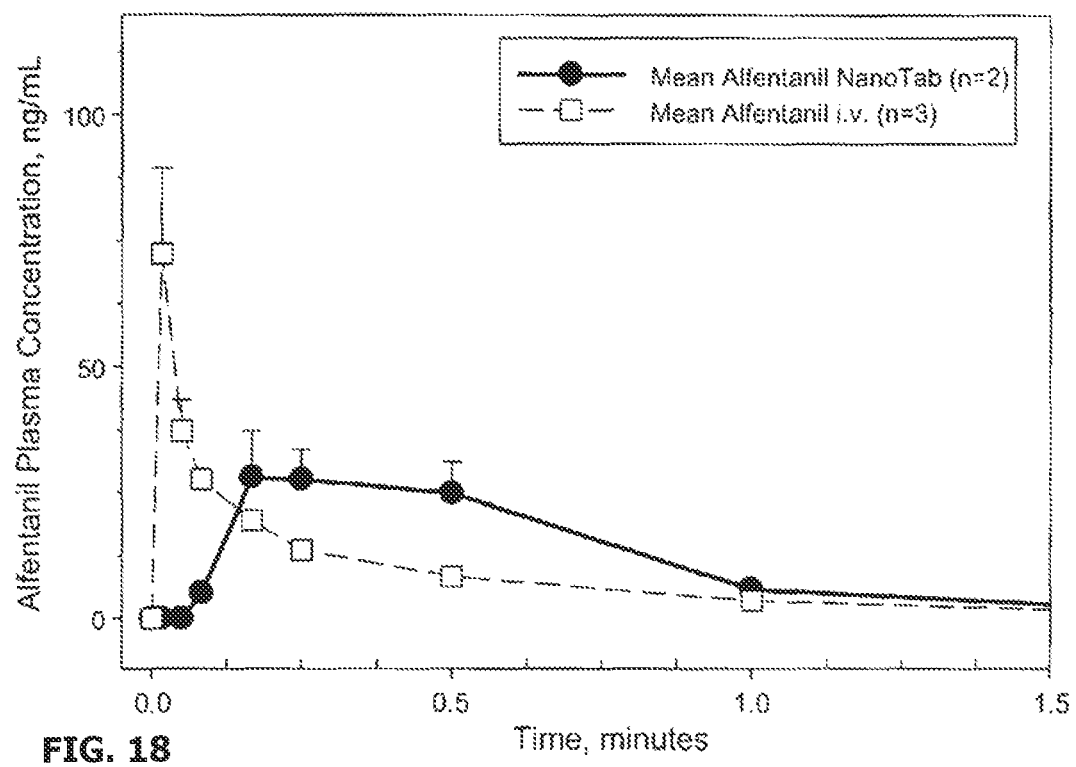
FIG. 18 is a graphic depiction of the pharmacokinetics of alfentanil following sublingual administration from Nano-Tab® formulation #63 (a=2), as compared to intravenous alfentanil administration (n=3) in a healthy, conscious Beagle dog model. Error bars represent standard errors around the mean.

The results are shown in FIG. 18. PK analysis results are summarized in Table 29.

TABLE 29

PK Analysis of Alfentanil sublingual formulations compared to intravenous alfentanil

| Group | F (%) | Absorption Variability (% CV) | $T_{onset}$ (min)[1] | $T_{max}$ (min) | $C_{max}$ (ng/mL) | Plasma Half-life (min) | Therapeutic Time Ratio[2] |
|---|---|---|---|---|---|---|---|
| Intravenous Alfentanil | — | 10.5 | 0.5 ± 0.05 | 1 ± 0 | 139.1 ± 76.4 | 4.4 ± 2.4 | 0.04 ± 0.02 |
| Sublingual Alfentanil Formulation | 94.1 ± 4.6 | 4.9 | 11.7 ± 1.3 | 15.0 ± 4.2 | 35.5 ± 2.6 | 40.8 ± 8.5 | 0.33 ± 0.07 |

[1]Time to reach 50% of $C_{max}$
[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of alfentanil to be 104 min in beagle dogs.

Example 15

Additional Exemplary Formulations Prepared By Direct Compression

For purposes of illustration a number of exemplary eroding placebo formulations prepared by the method of direct compression are provided below in Tables 30-31 which show the % w/w compositions of the excipients.

TABLE 30

Formulations prepared by direct compression

| Ingredients | A1 6HF | A2 6HF-1 | A3 6HF-2 | A4 5EF | A5 5EF-1 | A6 5EF-2 |
|---|---|---|---|---|---|---|
| Aluminum blue lake (dye) | 0.13 | 0.13 | 0.13 | 0.13 | 0.13 | 0.13 |
| Mannitol | 83.87 | 88.87 | 83.87 | 68.87 | 73.87 | 68.87 |
| Stearic Acid | | | | 5.00 | | |
| Pluronic F68 | | | | | | |
| Dibasic Calcium Phosphate | | | | 20.00 | 20.00 | 20.00 |
| HPMC - E4 | 10.00 | 10.00 | 15.00 | 5.00 | 5.00 | 10.00 |
| PEG 8000 | 5.00 | | | | | |
| Mg Stearate | 1.00 | 1.00 | 1.00 | 1.00 | 1.00 | 1.00 |
| Total | 100 | 100 | 100 | 100 | 100 | 100 |

TABLE 31

Formulations prepared by direct compression

| Ingredients | 5EF A7 | 5EF-3 A8 | 5EF-4 A9 | 5EF-5 A10 | 5EF-6 A11 | 5EF-7 A12 |
|---|---|---|---|---|---|---|
| Aluminum blue lake (dye) | 0.13 | 0.13 | 0.13 | 0.13 | 0.13 | 0.13 |
| Mannitol | 68.87 | 63.87 | 53.87 | 63.87 | 63.87 | 63.87 |
| Stearic Acid | 5.00 | 5.00 | 5.00 | 5.00 | 5.00 | 5.00 |
| Pluronic F68 | | | | | | |
| Polyox 303 | | | | | | |
| Dibasic Calcium Phosphate | 20.00 | 20.00 | 20.00 | 20.00 | 20.00 | 20.00 |
| HPMC - E4 - (HPMC- 2910, 3000-5600 cps) | 5.00 | 10.00 | 20.00 | | | |
| HPMC - E10 - (HPMC- 2910, 7500- 14000 cps) | | | | 10.00 | | |
| HPMC - K4 - (HPMC- 2208, 3000-5600 cps) | | | | | 10.00 | |
| HPMC - K100 - (HPMC- 2208, 80000- 120000 cps) | | | | | | 10.00 |
| PEG 8000 | | | | | | |
| Mg Stearate | 1.00 | 1.00 | 1.00 | 1.00 | 1.00 | 1.00 |
| Total | 100 | 100 | 100 | 100 | 100 | 100 |

Example 16

Exemplary Formulations Prepared By Wet Granulation

For purposes of illustration a number of exemplary eroding placebo formulations prepared by the method of wet granulation are provided below in Tables 32-35 which show the % w/w compositions of the excipients.

TABLE 32

Formulations prepared by wet granulation

| Ingredients | 5EF A13 | 5EF-4 A14 | 5EF-6 A15 |
|---|---|---|---|
| Ferric Oxide - Red Dye | 0.13 | 0.13 | 0.13 |
| Mannitol | 68.87 | 53.87 | 63.87 |
| Dibasic Calcium Phosphate | 20.00 | 20.00 | 20.00 |
| HPMC - E4- (HPMC- 2910, 3000-5600 cps) | 5.00 | 20.00 | |
| HPMC - K4 - (HPMC- 2208, 3000-5600 cps) | | | 10.00 |
| Stearic Acid | 5.00 | 5.00 | 5.00 |
| Mg Stearate | 1.00 | 1.00 | 1.00 |
| Total | 100 | 100 | 100 |

TABLE 33

Formulations prepared by wet granulation

| Ingredients | 5EF-6 A16 | 5EF-6A A17 | 5EF-6A1 A18 | 5EF-6A1a A19 | 5EF-6A2 A20 | 5EF-6B A21 | 5EF-6C A22 |
|---|---|---|---|---|---|---|---|
| Ferric Oxide - Red Dye | 0.13 | 0.13 | 0.13 | 0.13 | 0.13 | 0.13 | 0.13 |
| Mannitol | 63.87 | 63.87 | 59.87 | 55.87 | 59.87 | 68.87 | 55.87 |
| Dibasic Calcium Phosphate | 20.00 | 12.00 | 16.00 | 12.00 | 16.00 | 20.00 | 20.00 |
| HPMC - K4M - (HPMC- 2208, 3000-5600 cps) | 10.00 | 10.00 | 10.00 | 10.00 | 9.00 | 5.00 | 10.00 |
| HPMC in granulating fluid (HPMC E5) | | | | | 1.00 | | |
| PVP XL | | 8.00 | 8.00 | 16.00 | 8.00 | | |
| Ac-Di-Sol | | | | | | | 8.00 |
| Stearic Acid | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 |
| Total | 100 | 100 | 100 | 100 | 100 | 100 | 100 |

TABLE 34

Formulations prepared by wet granulation

| | Lot # | | | | | | | | |
|---|---|---|---|---|---|---|---|---|---|
| Ingredients | A23 5EF-6 | A24 5EF-6"" | A25 5EF-6D | A26 5EF-6E | A27 5EF-6F | A28 5EF-6G | A29 5EF-6H | A30 5EF-6I | A31 5EF-6J |
| Ferric Oxide - Red Dye | 0.13 | 0.13 | 0.13 | 0.13 | 0.13 | 0.13 | 0.13 | 0.33 | 0.13 |
| Mannitol | 63.87 | 63.87 | 72.87 | 70.87 | 63.87 | | | | |
| Sorbitol | | | | | | 63.87 | 83.87 | | |
| Microcrystalline Cellulose | | | | | | | | 43.87 | 43.87 |
| Dibasic Calcium Phosphate | 20.00 | 20.00 | 20.00 | 20.00 | 20.00 | 20.00 | | 20.00 | 20.00 |
| HPMC - K4M - (HPMC- 2208, 3000-5600 cps) | 10.00 | 10.00 | 1.00 | 3.00 | | 10.00 | 10.00 | 10.00 | |
| HPC | | | | | 10.00 | | | | |
| HPMC - E5 | | | | | | | | | 10.00 |
| PVP XL | | | | | | | | 20.00 | 20.00 |
| Stearic Acid | 5.00 | 5.00 | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 | 1.00 | 1.00 |
| Total | 100 | 100 | 100 | 100 | 100 | 100 | 100 | 100 | 100 |

TABLE 35

Formulations prepared by wet granulation

| | Lot # | | |
|---|---|---|---|
| | A32 | A33 | A34 |
| | Formulation Code | | |
| Ingredients | 5EF - 6 | 5EF - 6B | 5EF - 6E |
| Bromocresol Purple (dye) | 0.13 | 0.13 | 0.13 |
| Mannitol | 63.77 | 68.77 | 70.77 |
| Dibasic Calcium Phosphate | 20.00 | 20.00 | 20.00 |
| BHT | 0.05 | 0.05 | 0.05 |
| HPMC - K4M - (HPMC- 2208, 3000-5600 cps) | 10.00 | 5.00 | 3.00 |
| Stearic Acid | 5.00 | 5.00 | 5.00 |
| Mg Stearate | 1.00 | 1.00 | 1.00 |

TABLE 35-continued

Formulations prepared by wet granulation

| Ingredients | Lot # A32 | A33 | A34 |
|---|---|---|---|
| | Formulation Code | | |
| | 5EF - 6 | 5EF - 6B | 5EF - 6E |
| BHT | 5.00 | 0.05 | 0.05 |
| Total | 104.95 | 100.00 | 100.00 |

Example 17

Exemplary Formulations Prepared by Granulation

For purposes of illustration a number of exemplary eroding placebo formulations prepared by granulation are provided below in Tables 36-40 which show the % w/w compositions of the excipients.

TABLE 36

Formulations prepared by granulation

| Ingredients | Lot# A36 | A37 | A38 | A39 |
|---|---|---|---|---|
| BromoCresol Purple (dye) | 0.28 | 0.28 | 0.28 | 0.28 |
| Mannitol | 70.62 | 65.62 | 67.62 | 67.62 |
| Dibasic Calcium Phosphate | 20.00 | 20.00 | 20.00 | 20.00 |
| Sodium Starch Glycolate | | 5.00 | | |
| HPMC - K4M - (HPMC- 2208, 3000-5600 cps) | | 3.00 | 3.00 | 3.00 |
| HPMC - K100 LV | 3.00 | | | |
| Ac-Di-Sol | | | 3.00 | |
| PVP XL | | | | 3.00 |
| BHT | 0.05 | 0.05 | 0.05 | 0.05 |

TABLE 36-continued

Formulations prepared by granulation

| Ingredients | Lot# A36 | A37 | A38 | A39 |
|---|---|---|---|---|
| BHT | 0.05 | 0.05 | 0.05 | 0.05 |
| Stearic Acid | 5.00 | 5.00 | 5.00 | 5.00 |
| Mg Stearate | 1.00 | 1.00 | 1.00 | 1.00 |
| Total | 100.00 | 100.00 | 100.00 | 100.00 |
| Granulating Fluid (Ethanol:water) | (95:5) | (95:5) | (95:5) | (95:5) |

TABLE 37

Formulations prepared by granulation

| Ingredients | Lot# A40 | A41 | A42 | A43 | A44 | A45 |
|---|---|---|---|---|---|---|
| BromoCresol Purple (dye) | 0.28 | 0.28 | 0.28 | 0.28 | 0.28 | 69.62 |
| Mannitol | 65.62 | 62.62 | 65.62 | 62.62 | 70.52 | 20.00 |
| Dibasic Calcium Phosphate | 20.00 | 20.00 | 20.00 | 20.00 | 20.00 | 3.00 |
| HPMC - K4 - (HPMC-2208, 3000-5600 cps) | 3.00 | 3.00 | 3.00 | 3.00 | 3.00 | |
| PVP XL | | 3.00 | | 3.00 | | |
| Lutrol F68 | 5.00 | 5.00 | | | | |
| Lutrol F127 | | | 5.00 | 5.00 | | |
| Tween 80 | | | | | 0.10 | 1.00 |
| BHT | 0.05 | 0.05 | 0.05 | 0.05 | 0.05 | 0.05 |
| BHT | 0.05 | 0.05 | 0.05 | 0.05 | 0.05 | 0.05 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) |

TABLE 38

Formulations prepared by granulation

| Ingredients | Lot# A46 | A47 | A48 | A49 | A50 | A51 | A52 | A53 |
|---|---|---|---|---|---|---|---|---|
| BromoCresol Purple | 0.28 | 0.28 | 0.28 | 0.28 | 0.28 | 0.28 | 0.28 | 0.28 |
| Mannitol | 75.62 | 82.62 | 49.62 | 78.12 | 48.62 | 45.12 | 52.12 | 79.12 |
| Dibasic Calcium Phosphate | 10.0 | 10.0 | 40.0 | 10.0 | 40.0 | 40.0 | 40.0 | 10.0 |
| HPMC - K100LV | 3.0 | 0.0 | 3.0 | 0.0 | 0.0 | 3.0 | 0.0 | 3.0 |
| Ac-di-sol | 5.0 | 1.0 | 1.0 | 5.0 | 5.0 | 5.0 | 1.0 | 1.0 |
| Tween 80 | 0.0 | 0.0 | 0.0 | 0.5 | 0.0 | 0.5 | 0.5 | 0.5 |
| BHT | 0.05 | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 | 0.05 |
| Stearic Acid | 5.00 | 5.00 | 5.00 | 5.00 | 5.00 | 5.00 | 5.00 | 5.00 |
| Ms Stearate | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) | (95:5) | (95:5) |

TABLE 39

Formulations prepared by granulation

| Ingredients | Lot# A54 | A55 | A56 | A57 | A58 | A59 | A60 | A61 | A62 | A63 |
|---|---|---|---|---|---|---|---|---|---|---|
| Core ID | 85 | 86 | 87 | 88 | 89 | 90 | 91 | 92 | 93 | 94 |
| BromoCresol Purple | 0.28 | 0.28 | 0.28 | 0.28 | 0.28 | 0.28 | 0.28 | 0.28 | 0.28 | 0.28 |
| Mannitol | 72.62 | 70.62 | 80.62 | 67.62 | 69.62 | 62.62 | 70.62 | 67.62 | 67.62 | 60.62 |
| Dibasic Calcium Phosphate | 20.0 | | | | | 20.0 | | | 20.0 | 20.0 |
| MCC (Avicel 102) | | 20.0 | 10.0 | 20.0 | 20.0 | | | | | |
| HPMC - K4M | | 3.0 | 3.0 | 3.0 | | 3.0 | 3.0 | 3.0 | | |
| PEO 303 | 1.0 | | | | 1.0 | | | | | |
| Maltodextrin | | | | | | | | | 3.0 | 10.0 |
| Ac-di-sol | | | 3.0 | 3.0 | 3.0 | | | 3.0 | 3.0 | 3.0 |
| Na starch glycolate | | | | | 5.0 | | | | | |
| NaHCO3 | | | | | | | 20.0 | 20.0 | | |
| BHT | 0.05 | 0.05 | 0.05 | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 | 0.05 | 0.05 | 0.05 |
| Stearic Acid | 5.00 | 5.00 | 5.00 | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) | (95:5) | (95:5) | (95:5) | (95:5) |

TABLE 40

Formulations prepared by granulation

| Ingredients | Lot# A64 | A65 | A66 | A67 | A68 | A69 |
|---|---|---|---|---|---|---|
| Core ID | 96 | 97 | 98 | 99 | 100 | 101 |
| BromoCresol Purple | 0.28 | 0.28 | 0.28 | 0.28 | 0.28 | 0.28 |
| Mannitol | 80.62 | 77.62 | 74.62 | 77.62 | 77.62 | 80.62 |
| Dibasic Calcium Phosphate | | | | | | |
| MCC (Avicel 102) | 10.0 | 10.0 | 15.0 | | 10.0 | 10.0 |
| HPMC - K4M | 3.0 | 3.0 | | 3.0 | | |
| PEO 303 | | | 1.0 | | | |
| Maltodextrin | | | | | 3.0 | 3.0 |
| Ac-di-sol | | 3.0 | 3.0 | 3.0 | 3.0 | |
| NaHCO3 | | | | 10.0 | | |
| BHT | 0.05 | 0.05 | 0.05 | 0.05 | 0.05 | 0.05 |
| BHT | 0.05 | 0.05 | 0.05 | 0.05 | 0.05 | 0.05 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) |

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. A tablet comprising:
   about 5 to about 200 μg sufentanil or pharmaceutically acceptable salts thereof (expressed as the free base of sufentanil),
   60-95 wt % of one or more bulking agents,
   1-5 wt % of one or more hydrogel forming excipients, and
   1-10 wt % of one or more lubricants,
   wherein: said tablet has a volume less than about 30 μL, and when said tablet is adhered to the oral mucosa of a patient during the period of drug delivery:
   a) at least 55% of the total amount of sufentanil in the tablet is delivered via the oral transmucosal route;
   b) at least 90% of the total amount of sufentanil delivered to the patient, as measured by plasma concentration, is delivered via the oral transmucosal route;
   c) said tablet provides a mean $T_{max}$ of about 15 minutes to about 80 minutes;
   d) said tablet provides a mean $T_{max}$ with a coefficient of variation of less than 40%; and
   e) said tablet provides a dose-normalized mean $C_{max}$ of about 1.59-2.75 pg/mL per mcg dosed.

2. The tablet of claim 1, wherein said tablet has a volume of less than about 10 μL.

3. The tablet of claim 1 wherein said one or more bulking agents are selected from the group consisting of mannitol, di-calcium phosphate, and combinations thereof.

4. The tablet of claim 1, wherein said one or more hydrogel forming excipients is hydroxypropylmethylcellulose.

5. The tablet of claim 1, wherein said lubricant is selected from the group consisting of stearic acid, magnesium stearate, and combinations thereof.

6. The tablet of claim 1, wherein:
wherein said one or more bulking agents are selected from the group consisting of mannitol, di-calcium phosphate, and combinations thereof,
said one or more hydrogel forming excipients is hydroxypropylmethylcellulose,
and said lubricant is selected from the group consisting of stearic acid, magnesium stearate, and combinations thereof.

7. The tablet of claim 1, wherein the amount of sufentanil or pharmaceutically acceptable salts thereof is about 5 μg, 10 μg, 15 μg, 20 μg, 30 μg, 40 μg, 50 μg, 60 μg, 70 μg, 80 μg, 100 μg or 120 μg (expressed as the free base of sufentanil).

8. The tablet of claim 7, wherein the amount of sufentanil or pharmaceutically acceptable salts thereof is about 15 μg (expressed as the free base of sufentanil).

9. The tablet of claim 7, wherein the amount of sufentanil or pharmaceutically acceptable salts thereof is about 20 μg (expressed as the free base of sufentanil).

10. The tablet of claim 7, wherein the amount of sufentanil or pharmaceutically acceptable salts thereof is about 30 μg (expressed as the free base of sufentanil).

11. The tablet of claim 1, wherein after administration of said tablet to said subject, said tablet provides a mean $T_{max}$ range of from about 30 minutes to about 70 minutes.

12. The tablet of claim 1, wherein after administration of said tablet to said subject, said tablet provides a mean $T_{max}$ range of from about 40 minutes to about 55 minutes.

13. The tablet of claim 1, wherein after administration of said tablet to said subject, said tablet provides a mean $T_{max}$ range of from about 35 minutes to about 60 minutes.

14. The tablet of claim 1, wherein after administration of said tablet to said subject, said tablet provides a mean $T_{max}$ with a coefficient of variation of less than 30%.

15. The tablet of claim 1, wherein after administration of said tablet to said subject, at least 60% of the total amount of drug in said tablet is absorbed via the oral transmucosal route.

16. The tablet of claim 1, wherein after administration of said tablet to said subject, at least 70% of the total amount of drug in said tablet is absorbed via the oral transmucosal route.

17. The tablet of claim 1, wherein after administration of said tablet to said subject, at least 95% of the sufentanil delivered to the patient, as measured by plasma concentration, is delivered via the oral transmucosal route.

18. A method of treating pain, comprising administering the tablet of claim 1 to a patient in need thereof.

19. The method of claim 18, wherein said administering is by adhering said tablet to the sublingual membrane of said patient.

20. The method of claim 18, wherein said tablet has a volume of less than about 10 μL.

21. The method of claim 18, wherein said tablet is administered using a device.

22. A method of treating pain, comprising administering the tablet of claim 6 to a patient in need thereof.

23. A method of treating pain, comprising administering the tablet of claim 8 to a patient in need thereof.

24. The method of claim 23, wherein said tablet has a volume of less than about 10 μL.

25. The method of claim 23, wherein said tablet is administered using a device.

* * * * *